(12) United States Patent
Mühlebach et al.

(10) Patent No.: US 6,410,480 B1
(45) Date of Patent: Jun. 25, 2002

(54) HERBICIDALLY ACTIVE 3-HYDROXY-4-ARYL-5-OXOPYRAZOLINE DERIVATIVES

(75) Inventors: Michel Mühlebach, Binningen; Jutta Glock, Mumpf; Thomas Maetzke, Münchenstein, all of (CH); André Stoller, Blotzheim (FR)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/646,142

(22) PCT Filed: Mar. 11, 1999

(86) PCT No.: PCT/EP99/01593

§ 371 (c)(1), (2), (4) Date: Sep. 13, 2000

(87) PCT Pub. No.: WO99/47525

PCT Pub. Date: Sep. 23, 1991

(30) Foreign Application Priority Data

| Mar. 13, 1998 | (CH) | 616/98 |
| Dec. 8, 1998 | (CH) | 2431/98 |

(51) Int. Cl.$^7$ .................. A01N 43/90; C07D 498/04
(52) U.S. Cl. .............. 504/105; 504/106; 504/107; 504/110; 504/112; 504/218; 504/219; 504/220; 504/545
(58) Field of Search .......... 540/545; 504/218, 504/220, 105

(56) References Cited

U.S. PATENT DOCUMENTS

| 5,332,720 A | 7/1994 | Kruger et al. |
| 5,358,924 A | 10/1994 | Kruger et al. |
| 5,474,974 A | 12/1995 | Kruger et al. |
| 5,661,110 A | * 8/1997 | Krüger et al. ............ 504/281 |
| 5,683,965 A | 11/1997 | Bachmann et al. |
| 5,739,389 A | 4/1998 | Kruger et al. |
| 5,780,394 A | 7/1998 | Kruger et al. |

FOREIGN PATENT DOCUMENTS

| EP | 0 508 126 | 10/1992 |
| WO | 95/01971 | 1/1995 |
| WO | 96/11574 | 4/1996 |
| WO | 96/21652 | 7/1996 |

* cited by examiner

*Primary Examiner*—Robert W. Ramsuer
(74) *Attorney, Agent, or Firm*—William A. Teoli, Jr.

(57) ABSTRACT

The present invention relates to novel herbicidally active 3-hydroxy-4-aryl-5-oxopyrazoline derivatives, to processes for their preparation, to compositions which comprise these compounds and may additionally comprise safeners, and to the use of these compounds as herbicides for controlling weeds and grasses, in particular in crops of useful plants.

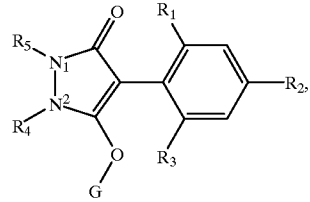

(I)

18 Claims, No Drawings

HERBICIDALLY ACTIVE 3-HYDROXY-4-ARYL-5-OXOPYRAZOLINE DERIVATIVES

This application is a 371 of PCT/EP 99/01593 filed Mar. 11, 1999.

The present invention relates to novel herbicidally active 3-hydroxy-4-aryl-5-oxopyrazoline derivatives, to processes for their preparation, to compositions which comprise these compounds and may additionally comprise safeners, and to the use of these compounds as herbicides for controlling weeds and grasses, in particular in crops of useful plants.

3-Hydroxy-4-aryl-5-oxopyrazoline derivates having herbicidal action are described, for example, in EP-A-0 508 126, WO 96/25395 and WO 96/21652. We have now found novel 3-hydroxy-4-aryl-5-oxopyrazoline derivatives having herbicidal properties.

The present invention thus provides compounds of the formula I

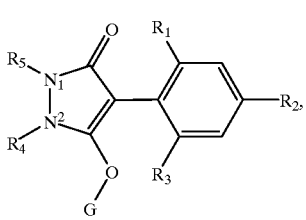

(I)

in which $R_1$, $R_2$ and $R_3$ independently of one another are halogen, nitro, cyano, $C_1$–$C_4$alkyl, $C_2$–$C_4$alkenyl, $C_2$–$C_4$alkynyl, $C_1$–$C_4$haloalkyl, $C_2$–$C_6$haloalkenyl, $C_3$–$C_6$cycloalkyl, halogen-substituted $C_3$–$C_6$cycloalkyl, $C_1$–$C_6$alkoxyalkyl, $C_1$–$C_6$alkylthioalkyl, hydroxyl, mercapto, $C_1$–$C_6$alkoxy, $C_3$–$C_6$alkenyloxy, $C_3$–$C_6$alkynyloxy, $C_1$–$C_4$alkylcarbonyl, $C_1$–$C_4$alkoxycarbonyl, $C_1$–$C_4$alkylthio, $C_1$–$C_4$alkylsulfinyl, $C_1$–$C_4$alkylsulfonyl, amino, $C_1$–$C_4$alkylamino or di($C_1$–$C_4$-alkyl)amino;

$R_4$ and $R_5$ together are a group

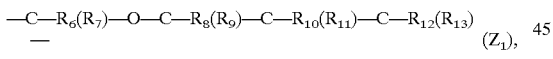

($Z_1$),

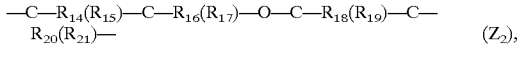

($Z_2$), or

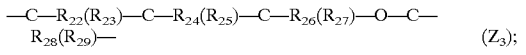

($Z_3$);

in which $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{29}$ independently of one another are hydrogen, halogen, $C_1$–$C_4$alkyl or $C_1$–$C_4$haloalkyl where an alkylene ring, which together with the carbon atoms of the groups $Z_1$, $Z_2$ or $Z_3$ contains 2 to 6 carbon atoms and may be interrupted by oxygen, may either be fused or spiro-linked to the carbon atoms of the groups $Z_1$, $Z_2$ or $Z_3$, or where this alkylene ring bridges at least one ring atom of the groups $Z_1$, $Z_2$ or $Z_3$;

G is hydrogen, —C($X_1$)—$R_{30}$, —C($X_2$)—$X_3$—$R_{31}$, —C($X_4$)—N($R_{32}$)—$R_{33}$, —SO$_2$—$R_{34}$, an alkali metal, alkaline earth metal, sulfonium or ammonium cation or —P($X_5$)($R_{35}$)—$R_{36}$;

$X_1$, $X_2$, $X_3$, $X_4$ and $X_5$ independently of one another are oxygen or sulfur; and $R_{30}$, $R_{31}$, $R_{32}$, $R_{33}$, $R_{34}$, $R_{35}$ and $R_{36}$ independently of one another are hydrogen, $C_1$–$C_5$alkyl, $C_1$–$C_5$haloalkyl, $C_2$–$C_5$alkenyl, $C_1$–$C_5$alkoxyalkyl, $C_3$–$C_6$cycloalkyl or phenyl, and $R_{34}$ is additionally $C_2$–$C_{20}$alkenyl, $C_2$–$C_{20}$alkenyl substituted by halogen, alkylcarbonyl, alkoxycarbonyl, alkylcarbonyloxy, alkoxy, thioalkyl, alkylthiocarbonyl, alkylcarbonylthio, alkylsulfonyl, alkylsulfoxyl, alkylaminosulfonyl, dialkylaminosultonyl, alkylsultonyloxy, alkylsulfonylamino, alkylamino, dialkylamino, alkylcarbonylamino, dialkylcarbonylamino, alkyl-alkylcarbonylamino, cyano, ($C_3$–$C_7$)cycloalkyl, ($C_3$–$C_7$)heterocyclyl, trialkylsilyl, trialkylsilyloxy, phenyl, substituted phenyl, heteroaryl or substituted heteroaryl, $C_2$–$C_{20}$alkynyl, $C_2$–$C_{20}$alkynyl substituted by halogen, alkylcarbonyl, alkoxycarbonyl, alkylcarbonyloxy, alkoxy, thioalkyl, alkylthiocarbonyl, alkylcarbonylthio, alkylsulfonyl, alkylsulfoxyl, alkylaminosulfonyl, dialkylaminosulfonyl, alkylsulfonyloxy, alkylsulfonylamino, alkyiamino, dialkylamino, alkylcarbonylamino, dialkylcarbonylamino, alkyl-alkylcarbonylamino, cyano, ($C_3$–$C_7$)cycloalkyl, ($C_3$–$C_7$)heterocyclyl, trialkylsilyl, trialkylsilyloxy, phenyl, substituted phenyl, heteroaryl or substituted heteroaryl, ($C_1$–$C_7$) cycloalkyl, ($C_1$–$C_7$)cycloalkyl substituted by halogen, haloalkyl, ($C_1$–$C_6$)alkyl, alkoxy, alkylcarbonyloxy, thioalkyl, alkylcarbonylthio, alkylamino, alkylcarbonylamino, trialkylsilyl or trialkylsilyloxy, heteroaryl, heteroaryl substituted by halogen, haloalkyt, nitro, cyano, ($C_1$–$C_6$)alkyl, alkoxy, alkylcarbonyloxy, thioalkyl, alkylcarbonylthio, alkylamino, alkylcarbonylamino, trialkylsilyl or trialkylsilyloxy, heteroaryloxy, substituted heteroaryloxy, heteroarylthio, substituted heteroarylthio, heteroarylamino, substituted heteroarylamino, diheteroarylamino, phenylamino, substituted phenylamino, diphenylamino, substituted diphenylamino, cycloalkylamino, substituted cycloalkylamino, dicycloalkylamino, substituted dicycloalkylamino, cycloalkoxy or substituted cycloalkoxy, and salts and diastereomers of the compounds of the formula I.

In the above definitions, halogen is to be understood as meaning fluorine, chlorine, bromine and iodine, preferably fluorine, chlorine and bromine. The alkyl groups in the definitions of the substituents are, for example, methyl, ethyl, n-propyl, isopropyl, n-butyl, sec-butyl, isobutyl or tert-butyl, and the isomeric pentyls and hexyls. Suitable cycloalkyl substituents contain 3 to 6 carbon atoms and are, for example, cyclopropyl, cyclobutyl, cyclopentyl or cyclohexyl. These may be mono- or polysubstituted by halogen, preferably by fluorine, chlorine or bromine. Alkenyl is to be understood as meaning, for example, vinyl, allyl, methallyl, 1-methylvinyl or but-2-en-1-yl. Alkynyl is, for example, ethinyl, propargyl, but-2-in-1-yl, 2-methylbutin-2-yl or but-3-in-2-yl. Haloalkyl groups preferably have a chain length of 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Suitable haloalkenyls are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_2$–$C_6$alkenyl groups which are mono-, di- or trisubstituted by halogen, preference is given to those having a chain length of 3 to 5 carbon atoms. Alkoxy groups preferably have a chain length of 1 to 6 carbon atoms. Alkoxy is, for example, methoxy, ethoxy, propoxy, isopropoxy, n-butoxy, isobutoxy, sec-butoxy and tert-butoxy, and the isomeric pentyloxy and hexyloxy radicals; preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Alkylthio groups preferably have a chain length of 1 to 4 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl. Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl. Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Alkoxyalkyl groups preferably have 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

Phenyl may be substituted. In this case, the substituents may be in the ortho, meta and/or para position. The substituents are preferably located in the positions ortho and para to the site where the ring is attached.

The halogen, alkyl, cycloalkyl, alkoxy, alkylthio, alkylcarbonyl, alkylsulfonyl and (di)alkylamino radicals which may be present in the radicals $R_{34}$, in particular —$SO_2R_{34}$ (G), are derived from the corresponding radicals mentioned above. Preferred heterocyclyl radicals are those containing 1 or 2 heteroatoms, for example N, S or O. They are usually saturated. Heteroaryl radicals are customarily aromatic heterocycles which preferably contain 1 to 3 heteroatoms, such as N, S and O. Examples of suitable heterocycles and heteroaromatics are: pyrrolidine, piperidine, pyran, dioxane, azetidine, oxetan, pyridine, pyrimidine, triazine, thiazole, thiadiazole, imidazole, oxazole, isoxazole and pyrazine, furan, morpholine, piperazine, pyrazole, benzoxazole, benzothiazole, quinoxaline and quinoline. These heterocycles and heteroaromatics may also be substituted, for example by halogen, alkyl, alkoxy, haloalkyl, haloalkoxy, nitro, cyano, thioalkyl, alkylamino or phenyl. The $C_2$–$C_{20}$alkenyl and alkynyl groups $R_{34}$ may be mono- or polyunsaturated They preferably contain 2 to 12, in particular 2 to 6, carbon atoms. For illustration, suitable groups —$SO_2R_{34}$ are given in the example below:

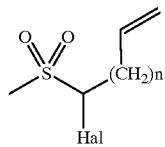 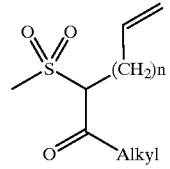

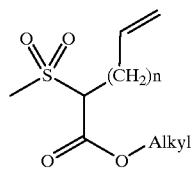 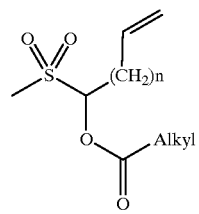

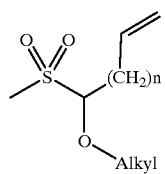 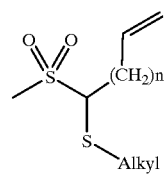

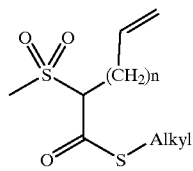 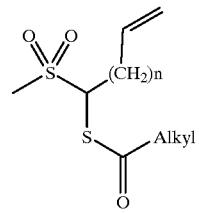

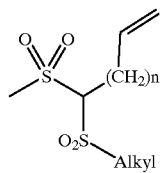 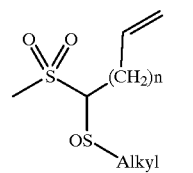

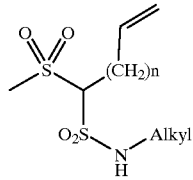 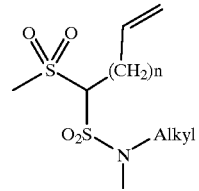

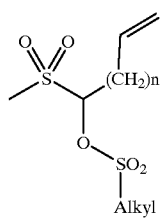 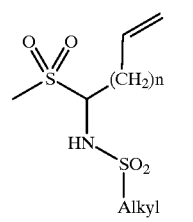

-continued

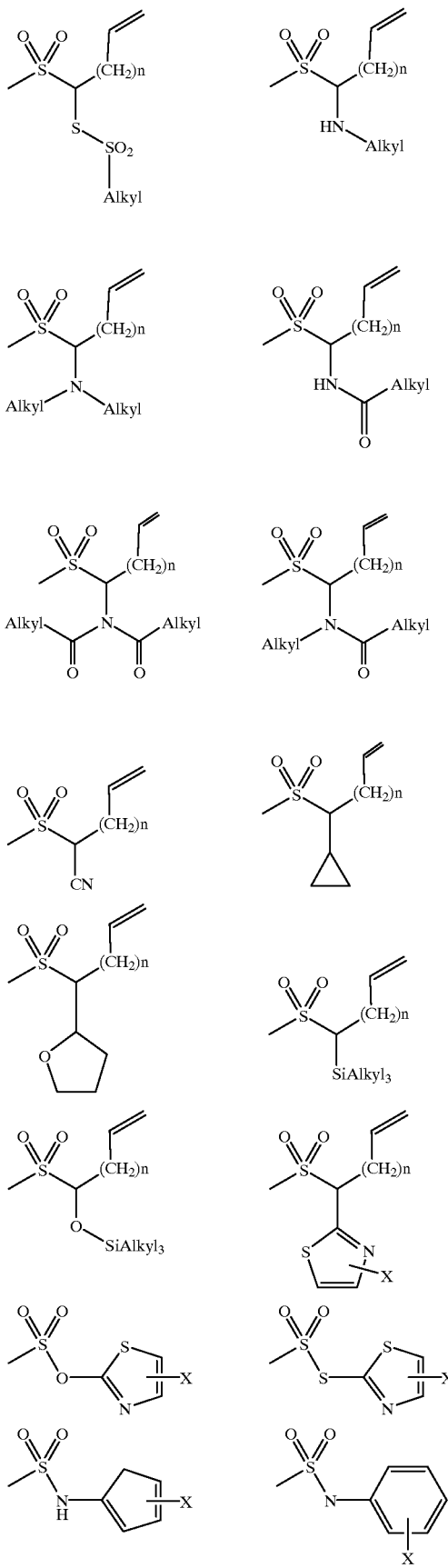

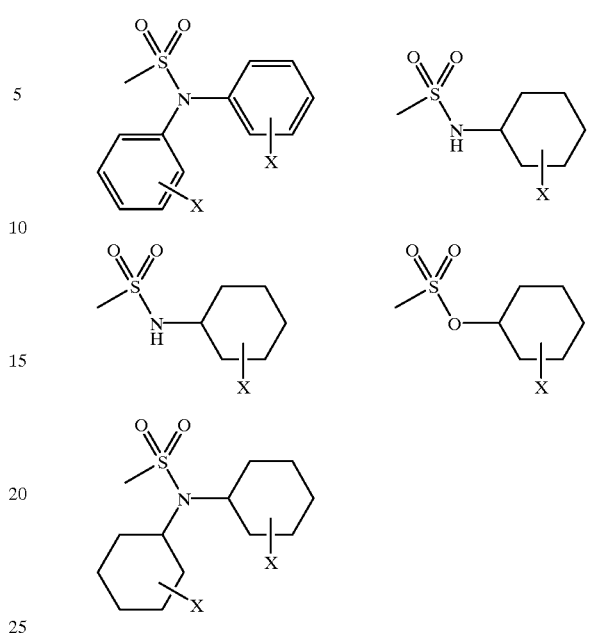

Alkali metal cations, alkaline earth metal cations or ammonium cations for the substituent G are, for example, the cations of sodium, potassium, magnesium, calcium and ammonium. Preferred sulfonium cations are, in particular, trialkylsulfonium cations, where the alkyl radicals each preferably contain 1 to 4 carbon atoms.

The free valency on the left hand of the groups $Z_1$, $Z_2$ and $Z_3$ is linked to the 1-position and the free valency on the right hand is linked to the 2-position of the pyrazoline ring.

Compounds of the formula I, in which an alkylene ring which, together with the carbon atoms of the groups $Z_1$, $Z_2$ and $Z_3$ contains 2 to 6 carbon atoms may be fused or spiro-linked to the groups $Z_1$, $Z_2$ and $Z_3$, have, for example, the following structure:

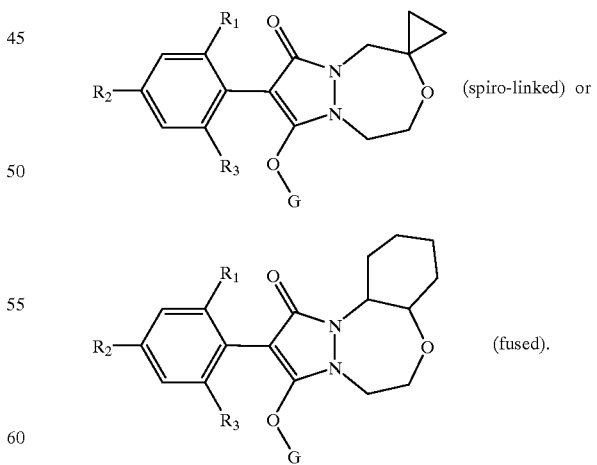

Compounds of the formula I, in which in the groups $Z_1$, $Z_2$ or $Z_3$ an alkylene ring bridges at least one ring atom of the groups $Z_1$, $Z_2$ or $Z_3$, have, for example, the following structure:

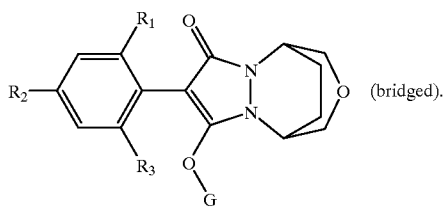

(bridged).

$R_4$ and $R_5$ together are in particular a group

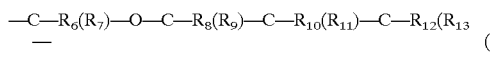

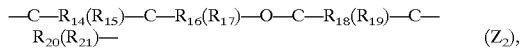

or

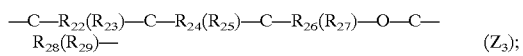

in which $R_6, R_7, R_8, R_9, R_{10}, R_{11}, R_{12}, R_{13}, R_{14}, R_{15}, R_{16}, R_{17}, R_{18}, R_{19}, R_{20}, R_{21}, R_{22}, R_{23}, R_{24}, R_{25}, R_{26}, R_{27}, R_{28}$ and $R_{29}$ independently of one another are hydrogen, halogen, $C_1$–$C_4$alkyl or $C_1$–$C_4$haloalkyl, where an alkylene ring which, together with the carbon atoms of the groups $Z_1$, $Z_2$ and $Z_3$, contains 3 to 6 carbon atoms may be fused or spiro-linked to the groups $Z_1$, $Z_2$ and $Z_3$.

Among the compounds of the formula I, preference is given to those in which G is hydrogen. In a particularly preferred group of compounds of the formula I, $R_4$ and $R_5$ together form a group $Z_2$. Also of particular interest are compounds of the formula I in which $R_1$, $R_2$ and $R_3$ independently of one another are halogen, $C_1$–$C_4$alkyl, $C_2$–$C_4$alkenyl, $C_2$–$C_4$alkynyl or $C_1$–$C_6$-alkoxy. Particular preference is given to compounds of the formula I in which $R_2$ is halogen, methyl, ethyl or ethinyl, and to compounds of the formula I in which $R_1$ and $R_3$ independently of one another are methyl, ethyl, isopropyl, vinyl, allyl, ethinyl, methoxy, ethoxy, bromine or chlorine. Very particular preference is given to compounds of the formula I in which G is the group —C($X_1$)—$R_{30}$ or C($X_2$)—($X_3$)—$R_{31}$ in which $X_1$, $X_2$ and $X_3$ are, in particular, oxygen, and $R_{30}$ and $R_{31}$ independently of one another are preferably $C_1$–$C_5$alkyl. Preference is furthermore given to compounds of the formula I in which $R_{30}$, $R_{31}$, $R_{32}$, $R_{33}$, $R_{34}$, $R_{35}$ and $R_{36}$ independently of one another are hydrogen, $C_1$–$C_5$alkyl or $C_1$–$C_5$haloalkyl.

Another preferred group of compounds of the formula I is is that where at least one ring atom of the groups $Z_1$, $Z_2$ or $Z_3$ is bridged by an alkylene ring which, together with the carbon atoms of the groups $Z_1$, $Z_2$ or $Z_3$, contains 2 to 6 carbon atoms and may be interrupted by oxygen.

The invention also includes the salts which the compounds of the formula I can form with acids. Suitable acids for forming the acid addition salts are both organic and inorganic acids. Examples of such acids are hydrochloric acid, hydrobromic acid, nitric acid, phosphoric acids, sulfuric acid, acetic acid, propionic acid, butyric acid, valeric acid, oxalic acid, malonic acid, fumaric acid, organic sulfonic acids, lactic acid, tartaric acid, citric acid and salicylic acid. The salts of the compounds of the formula I with acidic hydrogen also include alkali metal salts, for example sodium salts and potassium salts; alkaline earth metal salts, for example calcium salts and magnesium salts; ammonium salts, i.e. unsubstituted ammonium salts and mono- or polysubstituted ammonium salts, and salts with other organic nitrogen bases. Correspondingly, suitable salt formers are alkali metal and alkaline earth metal hydroxides, in particular the hydroxides of lithium, sodium, potassium, magnesium or calcium, where those of sodium or potassium are particularly important.

Examples of amines which are suitable for forming ammonium salts are both ammonia and primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methyinonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, N-methylmorpholine, thiomorpholine, piperidine, pyrrolidine, indoline, quinuclidine and azepine; primary arylamines, for example anilines, methoxyanilines, ethoxyanilines, o, m, p-toluidines, phenylenediamines, benzidines, naphthylamines and o, m, p-chloroanilines; but in particular triethylamine, isopropylamine and diisopropylamine.

In the processes described in this application, unless chiral starting materials are employed, the unsymmetrically substituted compounds of the formula I are generally obtained as racemates. The stereoisomers can then be separated by known methods, such as fractional crystallization after salt formation with optically pure bases, acids or metal complexes, or else by chromatographic processes such as high pressure liquid chromatography (HPLC) on acetylcellulose, owing to their physicochemical properties. In the present invention, the active compounds of the formula I are to be understood as meaning both the enriched and optically pure forms of the stereoisomers in question, and the racemates or diastereomers. Unless specific reference is made to the individual optical isomers, the given formula is to be understood as meaning those racemic mixtures which are formed in the preparation process mentioned. If an aliphatic C=C double bond is present, geometrical isomerism may additionally occur.

Also depending on the type of the substituents, the compounds of the formula I may be present as geometrical and/or optical isomers and isomer mixtures, and also as tautomers and mixtures of tautomers. These compounds of the formula I likewise form part of the subject-matter of the present invention. The compounds of the formula I in which the group G is hydrogen may, for example, be present in the following tautomer equilibriums:

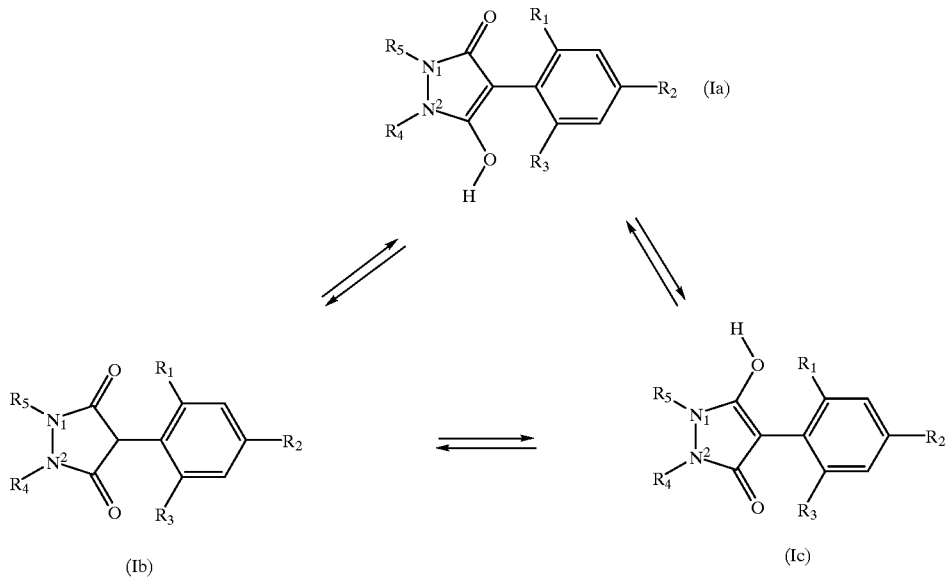

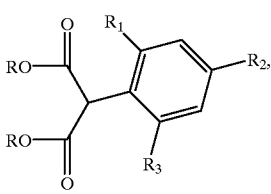

If G is different from hydrogen and Z is the group $Z_1$ or $Z_3$, or if G is different from hydrogen and $Z_2$ is unsymmetrically substituted, fused or spiro-linked, the compound of the formula I may be present as an isomer of the formula Id

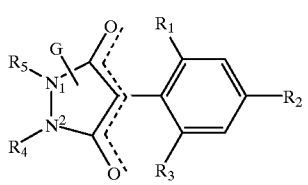

in which R is $C_1$–$C_6$alkyl, $C_1$–$C_6$haloalkyl, preferably methyl, ethyl or trichloroethyl, and $R_1$, $R_2$ and $R_3$ are as defined under formula I in an inert organic solvent, if appropriate in the presence of a base, with a compound of the formula IV or IVa Processes for preparing compounds which, with respect to the meaning of the substituents $R_4$ and $R_5$, are different from the compounds of the formula I according to the present invention are, for example, described in WO 96/21652. The compounds of the formula I according to the present invention can be prepared by methods similar to the processes described in WO 96/21652. The compounds of the formula II

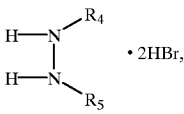

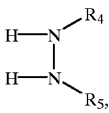

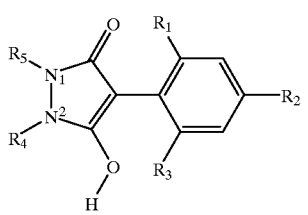

in which $R_1$, $R_2$, $R_3$, $R_4$ and $R_5$ are as defined under formula I and which are employed as starting materials for such processes can be prepared, for example, by reacting a compound of the formula III in which $R_4$ and $R_5$ are as defined under formula I. Other preparation processes for compounds of the formula II are described, for example, in WO 92/16510.

The compounds of the formula III are either known, or they can be prepared similarly to known processes. Processes for preparing compounds of the formula III and their reaction with hydrazines are described, for example, in WO 97/02243. Compounds of the formula III in which R is $C_1$–$C_6$alkyl, $C_1$–$C_6$haloalkyl, preferably methyl, ethyl or trichloroethyl, and $R_1$, $R_2$ and $R_3$ are as defined under formula I can be prepared by methods known to the person skilled in the art. For example, compounds of the formula III in which R is $C_1$–$C_6$alkyl, $C_1$–$C_6$haloalkyl, preferably methyl, ethyl or trichloroethyl, and $R_1$, $R_2$ and $R_3$ independently of one another are $C_1$–$C_4$alkyl, $C_2$–$C_4$alkenyl, $C_2$–$C_4$alkynyl can be prepared by the process of cross-coupling according to Stille (J. K. Stifle, Angew. Chem. 1986, 98, 504–519), Sonogashira (K. Sonogashira et al., Tetrahedron Lett. 1975, 4467–4470), Suzuki (N. Miyaura, A. Suzuki, Chem. Rev. 1995, 95, 2457–2483) or Heck (R. F. Heck, Org. React. 1982, 27, 345–390), with or without subsequent hydrogenation. This procedure is illustrated by the following reaction scheme:

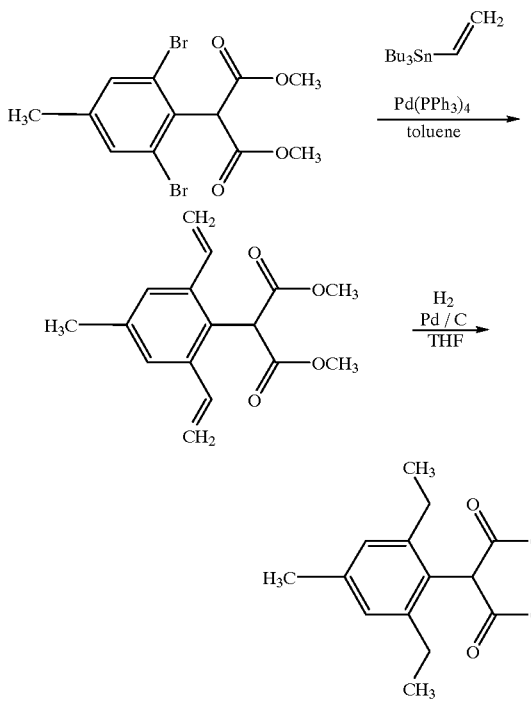

The compounds of the formulae IV and IVa are either known, or they can be prepared by known processes. Processes for preparing compounds of the formula IV are described, for example, in WO 95/00521. These compounds can be prepared, for example, by heating a compound of the formula V

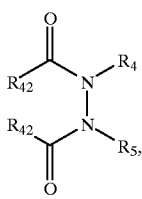

(V)

in which $R_{42}$ is hydrogen, $C_1$–$C_4$alkyl, $C_1$–$C_6$alkoxy, $C_1$–$C_6$haloalkoxy, benzyloxy, preferably hydrogen, methyl, methoxy, ethoxy, trichloroethoxy, tert-butoxy or benzyloxy and $R_4$ and $R_5$ are as defined under formula I in the presence of a base or an acid in an inert solvent. Compounds of the formula V in which $R_{42}$ is hydrogen, $C_1$–$C_4$alkyl, $C_1$–$C_6$alkoxy, $C_1$–$C_6$haloalkoxy, benzyloxy, preferably hydrogen, methyl, methoxy, ethoxy, trichloroethoxy, tert-butoxy or benzyloxy and $R_4$ and $R_5$ are as defined under formula I can be prepared, for example, by reacting a compound of the formula VI

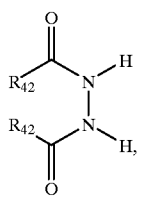

(VI)

in which $R_{42}$ is hydrogen, $C_1$–$C_4$alkyl, $C_1$–$C_6$alkoxy, $C_1$–$C_6$haloalkoxy, benzyloxy, preferably hydrogen, methyl, methoxy, ethoxy, trichforoethoxy, tert-butoxy or benzyloxy in the presence of a base and an inert solvent with a compound of the formula VII

Y–[$Z_1$, $Z_2$, or $Z_3$]–Y    (VII), in which Y is halogen, alkyllaryl sulfonates —$OSO_2R_{43}$, preferably bromine, chlorine, iodine, mesylate ($R_{43}$=$CH_3$), triflate ($R_{43}$=$CF_3$) or tosylate ($R_{43}$=p-tolyl) and $Z_1$, $Z_2$, and $Z_3$ are defined under formula I. In the formula VII, the free valencies of the groups $Z_1$, $Z_2$ and $Z_3$ are in each case attached to the group Y. Compounds of the formula VI and VII are known, or they can be prepared by methods known to the person skilled in the art.

Compounds of the formula IV in which $R_4$ and $R_5$ together are a group $Z_2$ —C—$R_{14}$($R_{15}$)—C—$R_{16}$($R_{17}$)—O—C—$R_{18}$($R_{19}$)—C—$R_{20}$($R_{21}$)— ($Z_2$), in which $R_{14}$, $R_{15}$, $R_{16}$, $R_{17}$, $R_{18}$, $R_{19}$, $R_{20}$ and $R_{21}$ are hydrogen can be prepared, for example, according to the following reaction scheme:

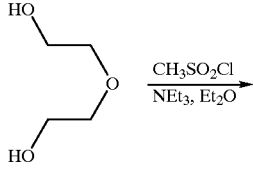

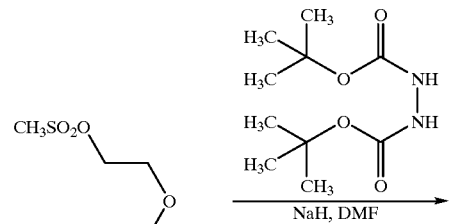

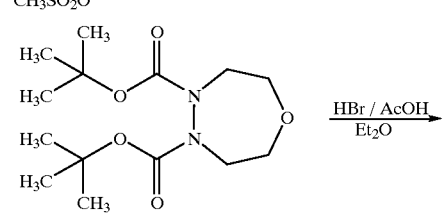

Compounds of the formula I in which $R_4$ and $R_5$ are a group $Z_1$ or $Z_3$ can be prepared using the methods of the synthesis examples given above. Thus, the compounds of the formula III can, for example, be reacted with a hydrazine alkanol of the formula IV(b)

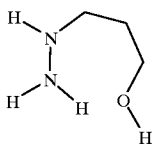
(IVb)

(here, $R_6$–$R_{13}$ and $R_{22}$–$R_{29}$ are hydrogen) to give the compounds of the formula IVc

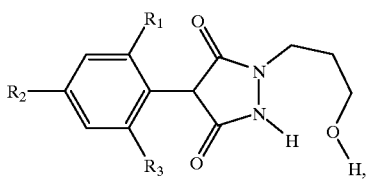
(IVc)

followed by a cyclization, for example with formaldehyde, to give the end products of the formula Ie

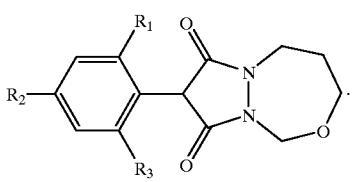
(Ie)

The compound of the formula Ie in which $R_1$ and $R_3$ are ethyl and $R_2$ is methyl has a melting point of 186–191° C. (decomp.). Similarly, it is also possible to prepare compounds of the formula I in which the substituents $R_6$–$R_{13}$ and $R_2$–$R_{29}$ are different from hydrogen and, independently of one another, have one of the meanings mentioned for them above.

The end products of the formula I can be isolated in a customary manner by concentration and/or evaporation of the solvent and be purified by recrystallization or trituration of the solid residue in solvents in which they are not readily soluble, such as ethers, alkanes, aromatic hydrocarbons or chlorinated hydrocarbons, or by chromatography. Salts of compounds of the formula I can be prepared in a manner known per se. Such preparation methods are described, for example, in WO 96/21652.

The compounds of the formula I or compositions comprising them can be used according to the invention by all the application methods customary in agriculture, for example pre-emergence application, postemergence application and seed dressing, and various methods and techniques, for example controlled release of active compounds. To this end, the active compound is absorbed in solution onto mineral granule carriers or polymerized granules (urea/formaldehyde) and dried. If appropriate, a coating which allows the active compound to be released in metered form over a certain period of time can additionally be applied (coated granules).

The compounds of the formula I can be employed as herbicides in unchanged form, i.e. as they are obtained in the synthesis, but they are preferably processed in a customary manner with the auxiliaries conventionally used in the art of formulation, for example to give emulsifiable concentrates, directly sprayable or dilutable solutions, dilute emulsions, wettable powders, soluble powders, dusts, granules or microcapsules. Such formulations are described, for example, in WO 97/34485 on pages 9 to 13. The methods of application, such as spraying, atomizing, dusting, wetting, scattering or watering, in the same way as the nature of the compositions, are chosen according to the required aims and the given circumstances.

The formulations, i.e. the compositions, formulations or preparations comprising the active compound of the formula I or at least one active compound of the formula I and as a rule one or more solid or liquid formulation auxiliaries, are prepared in a known manner, for example by intimate mixing and/or grinding of the active compounds with the formulation auxiliaries, for example solvents or solid carriers. Surface-active compounds (surfactants) can furthermore additionally be used during the preparation of the formulations. Examples of solvents and solid carriers are given, for example, in WO 97/34485 on page 6. Depending on the nature of the active compound of the formula I to be formulated, suitable surface-active compounds are nonionic, cationic and/or anionic surfactants and surfactant mixtures having good emulsifying, dispersing and wetting properties.

Examples of suitable anionic, nonionic and cationic surfactants are listed, for example, in WO 97/34485 on pages 7 and 8.

The surfactants conventionally used in the art of formulation and which can also be used to prepare the herbicidal compositions according to the invention are described, inter alia, in "Mc Cutcheon's Detergents and Emulsifiers Annual", MC Publishing Corp., Ridgewood N.J., 1981, Stache, H., "Tensid-Taschenbuch" [Surfactant handbook], Carl Hanser Verlag, Munich/Vienna, 1981 and M. and J. Ash, "Encyclopedia of Surfactants", Vol I-III, Chemical Publishing Co., New York, 1980–81.

The efficacy of herbicidal and plant-growth-inhibiting compositions according to the invention containing a herbicidally effective amount of a compound of the formula I can be enhanced by addition of spray tank adjuvants.

These adjuvants may be, for example: nonionic surfactants, mixtures of nonionic surfactants, mixtures of anionic surfactants with nonionic surfactants, cationic surfactants, organosilicon surfactants, mineral oil derivatives with and without surfactants, vegetable oil derivatives with and without addition of surfactants, alkylated derivatives of oils of vegetable or mineral origin with and without surfactants, fish oils and other oils of animal nature and their alkyl derivatives with and without surfactants, natural higher fatty acids, preferably having 8 to 28 carbon atoms, and their alkyl ester derivatives, organic acids which contain an aromatic ring system and one or more carboxylic esters, and their alkyl derivatives, furthermore suspensions of polymers of vinyl acetate or copolymers of vinyl acetate/acrylic esters. Mixtures of individual adjuvants with one another and in combination with organic solvents may further increase the effect.

Suitable nonionic surfactants are, for example, polyglycol ether derivatives of aliphatic or cycloaliphatic alcohols, saturated or unsaturated fatty acids and alkylphenols, preferably those which may contain 3 to 30 glycol ether groups and 8 to 20 carbon atoms in the (aliphatic)hydrocarbon radical and 6 to 18 carbon atoms in the alkyl radical of the alkylphenols.

Other suitable nonionic surfactants are the water-soluble polyethylene oxide adducts on polypropylene glycol, ethylenediaminopolypropylene glycol and alkylpolypropylene glycol preferably having 1 to 10 carbon atoms in the alkyl chain which preferably contain 20 to 250 ethylene glycol ether groups and 10 to 100 propylene glycol ether groups. The abovementioned compounds generally contain 1 to 5 ethylene glycol units per propylene glycol unit.

Other examples of nonionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Also suitable are fatty esters of polyoxyethylene sorbitan, for example polyoxyethylene sorbitan trioleate.

Preferred anionic surfactants are, in particular, alkyl sulfates, alkyl sulfonates, alkylaryl sulfonates, alkylated phosphoric acids and their ethoxylated derivatives. The alkyl radicals usually contain 8 to 24 carbon atoms.

Preferred nonionic surfactants are known under the following trade names:

Polyoxyethylene cocoalkylamine (for example AMIET® 105 (Kao Co.)), polyoxyethylene oleylamine (for example AMIET® 415 (Kao Co.)), nonylphenolpolyethoxyethanols, polyoxyethylene stearylamine (for example AMIET® 320 (Kao Co.)), N-polyethoxyethylamines (for example GENAMIN® (Hoechst AG)), N,N,N',N'-tetra (polyethoxypolypropoxyethyl)ethylene diamines (for example TERRONIL® and TETRONIC® (BASF Wyandotte Corp.)), BRIJ® (Atlas Chemicals), ETHYLAN® CD and ETHYLAN® D (Diamond Shamrock), GENAPOL® C, GENAPOL® O, GENAPOL® S and GENAPOL® X080 (Hoechst AG), EMULGEN® 104P, EMULGEN® 109P and EMULGEN® 408 (Kao Co.); DISTY® 125 (Geronazzo), SOPROPHOR® CY 18 (Rhône Poulenc S.A.); NONISOL® (Ciba-Geigy), MRYJ® (ICI); TWEEN® (ICI); EMULSOGEN® (Hoechst AG); AMIDOX® (Stephan Chemical Co.), ETHOMID® (Armak Co.); PLURONIC® (BASF Wyandotte Corp.), SOPROPHOR® 461P (Rhône Poulenc S.A.), SOPROPHOR® 496/P (Rhône Poulenc S.A.), ANTAROX FM-63 (Rhône Poulenc S.A.), SLYGARD 309 (Dow Coming), SILWET 408, SILWET L-7607N (Osi-Specialities).

The cationic surfactants are primarily quaternary ammonium salts which contain, as N-substituents, at least one alkyl radical having 8 to 22 C atoms and, as further substituents, lower nonhalogenated or halogenated alkyl, benzyl or lower hydroxyalkyl radicals. The salts are preferably present as halides, methyl sulfates or ethyl sulfates, for example stearyltrimethylammonium chloride or benzyldi(2-chloroethyl)ethylammonium bromide.

The oils used are either of mineral or natural origin. The natural oils may additionally be of animal or vegetable origin. In the case of animal oils, preference is given, in particular, to derivatives of beef tallow, but fish oils (for example sardine oil) and derivatives thereof are also used. Vegetable oils are mainly seed oils of various origin. Examples of particularly preferred vegetable oils which may be mentioned are coconut, rapeseed or sunflower oils and derivatives thereof.

Surfactants, oils, in particular vegetable oils, derivatives thereof such as alkylated fatty acids and mixtures thereof, for example with preferably anionic surfactants such as alkylated phosphoric acids, alkyl sulfates and alkylaryl sulfonates and higher fatty acids which are customary in formulation and adjuvant technique and which can also be employed in the compositions according to the invention and spray tank solins thereof are described, inter alia, in "Mc Cutcheon's Detergents and Emulsifiers Annual", MC Publishing Corp., Ridgewood N.J., 1998, Stache, H., "Tensid-Taschenbuch" [Surfactant handbook], Carl Hanser Verlag, Munich/Vienna, 1990, M. and J. Ash, "Encyclopedia of Surfactants", Vol. I-IV, Chemical Publishing Co., New York, 1981–89, G. Kapusta, "A Compendium of Herbicide Adjuvants", Southern Illinois Univ., 1998, L. Thomson Harvey, "A Guide to Agricultural Spray Adjuvants Used in the United States", Thomson Pubns., 1992.

The herbicidal formulations as a rule comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant. While concentrated compositions are rather preferred as commercial goods, the end user as a rule uses dilute compositions. The compositions can also comprise further additives, such as stabilizers, for example epoxidized or non-epoxidized vegetable oils (epoxidized coconut oil, rapeseed oil or soya oil), defoamers, for example silicone oil, preservatives, viscosity regulators, binders, tackifiers and fertilizers or other active compounds.

The herbicidally active compounds of the formula I are as a rule applied to the plants or their habitat, at application rates of 0.001 to 4 kg/ha, in particular 0.005 to 2 kg/ha. The dosage required for the desired effect can be determined by tests. It depends on the nature of the effect, the development stage of the crop plant and the weed and on the application (location, time, process) and can, as a function of these parameters, vary within wide ranges.

The compounds of the formula I have herbicidal and growth-inhibiting properties, owing to which they can be used in crops of useful plants, in particular in cereals, cotton, soya, sugar beet, sugar cane, plantings, rapeseed, maize and rice, very particularly in maize and cereals, and for the non-selective control of weeds. Crops include those which have been rendered tolerant towards herbicides or herbicide classes by conventional breeding methods or genetical engineering methods. The weeds to be controlled can be both monocotyledonous and dicotyledonous weeds, for example Stellaria, Agrostis, Digitaria, Avena, Brachiaria, Phalaris, Setaria, Sinapis, Lolium, Solanum, Echinochloa, Scirpus, Monochoria, Sagittaria, Panicum, Bromus, Alopecurus, *Sorghum halepense, Sorghum bicolor,* Rottboellia, Cyperus, Abutilon, Sida, Xanthium, Amaranthus, Chenopodium, Ipomoea, Chrysanthemum, Galium, Viola, Matricharia, Papaver and Veronica. The herbicidal composition according to the invention is particularly suitable for controlling Alopecurus, Avena, Agrostis, Setaria, Phalaris, Lolium, Panicum, Echinochloa, Brachiaria and Digitaria.

Surprisingly, it has been found that specific safeners known from U.S. Pat. Nos. 5,041,157, 5,541,148, 5,006,656, EP-A-0 094 349, EP-A-0 551 650, EP-A-0 268 554, EP-A-0 375 061, EP-A-0 174 562, EP-A-492 366, WO 91/7874, WO 94/987, DE-A-19 612 943, WO 96/29870, WO 98/13361, WO 98/39297, WO 98/27049, EP 716 073, EP 613 618, U.S. Pat. No. 5,597,776 and EP-A430 004 are suitable for mixing with the herbicidal composition according to the invention. Consequently, the present invention also relates to a selective herbicidal composition for controlling grasses and weeds in crops of useful plants, in particular in crops of maize and cereals, said composition comprising a herbicide of the formula I and a safener (antidote) and which protects the useful plants, but not the weeds, against the phytotoxic effect of the herbicide, and to the use of this composition for controlling weeds in crops of useful plants.

According to the invention, a selective-herbicidal composition is therefore proposed which, in addition to customary inert formulation auxiliaries such as carriers, solvents and wetting agents, comprises, as active compound, a mixture of a) a herbicidally effective amount of a compound of the formula I

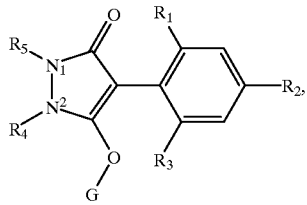

(I)

in which $R_1$, $R_2$, $R_3$, $R_4$, $R_5$ and G are as defined above, and b) a herbicide-antagonistically effective amount of either a compound of the formula X

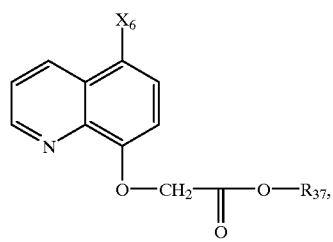

(X)

in which $R_{37}$ is hydrogen, $C_1$–$C_8$alkyl or $C_1$–$C_6$alkoxy- or $C_3$–$C_6$alkenyloxy-substituted $C_1$–$C_8$alkyl; and $X_6$ is hydrogen or chlorine; or a compound of the formula XI

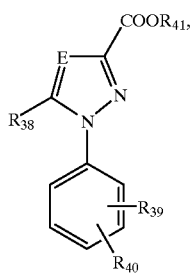

(XI)

in which

E is nitrogen or methine;

$R_{38}$ is —$CCl_3$, phenyl or halogen-substituted phenyl;

$R_{39}$ and $R_{40}$ independently of one another are hydrogen or halogen; and $R_{41}$ is $C_1$–$C_4$alkyl; or a compound of the formula XII

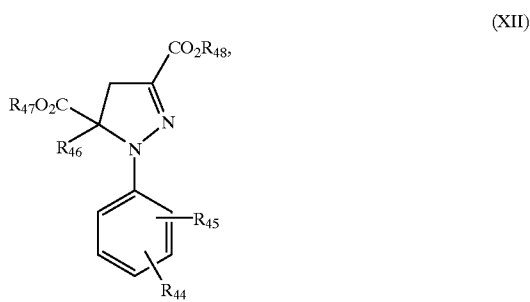

(XII)

in which $R_{44}$ and $R_{45}$ independently of one another are hydrogen or halogen and $R_{46}$, $R_{47}$ and $R_{48}$ independently of one another are $C_1$–$C_4$alkyl, or a compound of the formula XIII

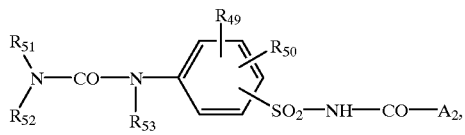

(XIII)

in which $A_2$ is a group

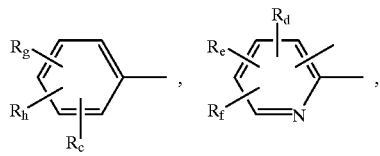

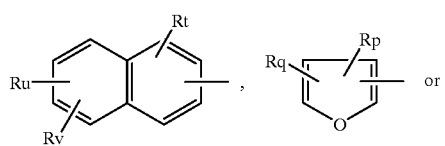

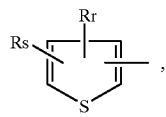

, $R_{51}$ and $R_{52}$ independently of one another are hydrogen, $C_1$–$C_8$alkyl, $C_3$–$C_8$cycloalkyl, $C_3$–$C_6$alkenyl, $C_3$–$C_6$alkynyl,

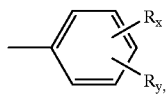

or C$_1$–C$_4$alkoxy— or

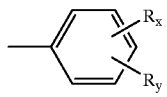

substituted C$_1$–C$_4$alkyl; or R$_{51}$ and R$_{52}$ together form a C$_4$–C$_6$alkylene bridge which may be interrupted by oxygen, sulfur, SO, SO$_2$, NH or —N(C$_1$–C$_4$alkyl)—, R$_{53}$ is hydrogen or C$_1$–C$_4$alkyl;

R$_{49}$ is hydrogen, halogen, cyano, trifluoromethyl, nitro, C$_1$–C$_4$alkyl, C$_1$–C$_4$alkoxy, C$_1$–C$_4$alkylthio, C$_1$–C$_4$alkylsulfinyl, C$_1$–C$_4$alkylsulfonyl, —COOR$_j$, —CONR$_k$R$_m$, —COR$_n$, —SO$_2$NR$_k$R$_m$ or —OSO$_2$—C$_1$–C$_4$alkyl;

R$_g$ is hydrogen, halogen, cyano, nitro, C$_1$–C$_4$alkyl, C$_1$–C$_4$haloalkyl, C$_1$–C$_4$alkylthio, C$_1$–C$_4$alkylsulfinyl, C$_1$–C$_4$alkylsulfonyl, —COOR$_j$, CONR$_k$R$_m$, —COR$_n$, SO$_2$NR$_k$R$_m$, —OSO$_2$—C$_1$–C$_4$alkyl, C$_1$–C$_6$alkoxy, or C$_1$–C$_6$alkoxy which is substituted by C$_1$–C$_4$alkoxy or halogen, C$_3$–C$_6$alkenyloxy, or C$_3$–C$_6$alkenyloxy which is substituted by halogen, or C$_3$–C$_6$alkynyloxy, or R$_{49}$ and R$_{50}$ together form a C$_3$–C$_4$alkylene bridge which may be substituted by halogen or C$_1$–C$_4$alkyl, or they form a C$_3$–C$_4$alkenylene bridge which may be substituted by halogen or C$_1$–C$_4$alkyl, or they form a C$_4$alkadienylene bridge which may be substituted by halogen or C$_1$–C$_4$alkyl;

R$_{50}$ and R$_h$ independently of one another are hydrogen, halogen, C$_1$–C$_4$alkyl, trifluoromethyl, C$_1$–C$_6$alkoxy, C$_1$–C$_6$alkylthio or —COOR$_j$;

R$_c$ is hydrogen, halogen, nitro, C$_1$–C$_4$alkyl or methoxy;

R$_d$ is hydrogen, halogen, nitro, C$_1$–C$_4$alkyl, C$_1$–C$_4$alkoxy, C$_1$–C$_4$alkylthio, C$_1$–C$_4$alkylsulfinyl, C$_1$–C$_4$alkylsulfonyl, —COOR$_j$ or CONR$_k$R$_m$;

R$_e$ is hydrogen, halogen, C$_1$–C$_4$alkyl, —COOR$_j$, trifluoromethyl or methoxy, or R$_d$ and R$_e$ together form a C$_3$–C$_4$alkylene bridge;

R$_p$ is hydrogen, halogen, C$_1$–C$_4$alkyl, —COOR$_j$, trifluoromethyl or methoxy; Rq is hydrogen, halogen, nitro, C$_1$–C$_4$alkyl, C$_1$–C$_4$alkoxy, C$_1$–C$_4$alkylthio, C$_1$–C$_4$alkylsulfinyl, C$_1$–C$_4$alkylsulfonyl, —COOR$_j$ or CONR$_k$R$_m$, or Rp and Rq together form a C$_3$–C$_4$alkylene bridge;

Rr is hydrogen, halogen, C$_1$–C$_4$alkyl, —COOR$_j$, trifluoromethyl or methoxy; R$_s$ is hydrogen, halogen, nitro, C$_1$–C$_4$alkyl, C$_1$–C$_4$alkoxy, C$_1$–C$_4$alkylthio, C$_1$–C$_4$alkylsulfinyl, C$_1$–C$_4$alkylsulfonyl, —COOR$_j$ or CONR$_k$R$_m$, or Rr and Rs together form a C$_3$–C$_4$alkylene bridge;

Rt is hydrogen, halogen, C$_1$–C$_4$alkyl, —COOR$_j$, trifluoromethyl or methoxy; Ru is hydrogen, halogen, nitro, C$_1$–C$_4$alkyl, C$_1$–C$_4$alkoxy, C$_1$–C$_4$alkylthio, C$_1$–C$_4$alkylsulfinyl, C$_1$–C$_4$alkylsulfonyl, —COOR$_j$ or CONR$_k$R$_m$, or Rv and Ru together form a C$_3$–C$_4$alkylene bridge;

R$_f$ and Rv are hydrogen, halogen or C$_1$–C$_4$alkyl; R$_x$ and R$_y$ independently of one another are hydrogen, halogen, C$_1$–C$_4$alkyl, C$_1$–C$_4$alkoxy, C$_1$–C$_4$alkylthio, —COOR$_{54}$, trifluoromethyl, nitro or cyano;

R$_j$, R$_k$ and R$_m$ independently of one another are hydrogen or C$_1$–C$_4$alkyl; or R$_k$ and R$_m$ together form a C$_4$–C$_6$alkylene bridge which may be interrupted by oxygen, NH or —N(C$_1$–C$_4$alkyl)—;

R$_n$ is C$_1$–C$_4$alkyl, phenyl, or halogen-, C$_1$–C$_4$alkyl-, methoxy-, nitro or trifluoromethyl-substituted phenyl;

R$_{54}$ is hydrogen, C$_1$–C$_{10}$alkyl, C$_1$–C$_4$alkoxy-C$_1$–C$_4$alkyl, C$_1$–C$_4$alkylthio-C$_1$–C$_4$alkyl, di-C$_1$–C$_4$alkylamino-C$_1$–C$_4$alkyl, halo-C$_1$–C$_8$alkyl, C$_2$–C$_8$alkenyl, halo-C$_2$–C$_8$alkenyl, C$_3$–C$_8$alkynyl, C$_{C7}$cycloalkyl, halo-C$_3$–C$_7$cycloalkyl, C$_1$–C$_8$alkylcarbonyl, allylcarbonyl, C$_3$–C$_7$cycloalkylcarbonyl, benzoyl which is unsubstituted or substituted up to three times on the phenyl ring by identical or different substituents selected from the group consisting of halogen, C$_1$–C$_4$alkyl, halo-C$_1$–C$_4$alkyl, halo-C$_1$–C$_4$alkoxy or C$_1$–C$_4$alkoxy; or furoyl, thienyl; or C$_1$–C$_4$alkyl which is substitute by phenyl, halophenyl, C$_1$–C$_4$alkylphenyl, C$_1$–C$_4$alkoxyphenyl, halo-C$_1$–C$_4$alkylphenyl, halo-C$_1$–C$_4$alkoxyphenyl, C$_1$–C$_6$alkoxycarbonyl, C$_1$–C$_4$alkoxy-C$_1$–C$_8$alkoxycarbonyl, C$_3$–C$_8$alkenyloxycarbonyl, C$_3$–C$_8$alkynyloxycarbonyl, C$_1$–C$_8$alkylthiocarbonyl, C$_3$–C$_8$alkenylthiocarbonyl, C$_3$–C$_8$alkynylthiocarbonyl, carbamoyl, mono-C$_1$–C$_4$alkylaminocarbonyl, di-C$_1$–C$_4$alkylaminocarbonyl; or phenylaminocarbonyl which is unsubstituted or substituted up to three times on the phenyl by identical or different substituents selected from the group consisting of halogen, C$_1$–C$_4$alkyl, halo-C$_1$–C$_4$alkyl, halo-C$_1$–C$_4$alkoxy and C$_1$–C$_4$alkoxy, or is monosubstituted by cyano or nitro, or dioxoian-2-yl which is unsubstituted or substituted by one or two C$_1$–C$_4$alkyl radicals, or dioxan-2-yl which is unsubstituted or substituted by one or two C$_1$–C$_4$alkyl radicals, or C$_1$–C$_4$alkyl which is substituted by cyano, nitro, carboxyl or C$_1$–C$_8$alkylthio-C$_1$–C$_8$alkoxycarbonyl;

or a compound of the formula XIV (XIV)

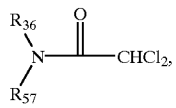

in which

R$_{56}$ and R$_{57}$ independently of one another are C$_1$–C$_6$alkyl or C$_2$–C$_6$alkenyl; or R$_{56}$ and $R_{57}$ together are

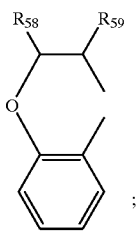

$R_{58}$ and $R_{59}$ independently of one another are hydrogen or $C_1$–$C_6$alkyl; or $R_{56}$ and $R_{57}$ together are

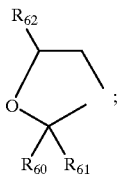

$R_{60}$ and $R_{61}$ independently of one another are $C_1$–$C_4$alkyl, or $R_{60}$ and $R_{61}$ together are —(CH$_2$)$_5$—;
$R_{62}$ is hydrogen, $C_1$–$C_4$alkyl or

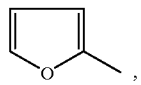

or $R_{56}$ and $R_{57}$ together are

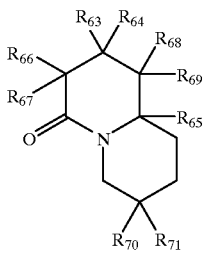 or 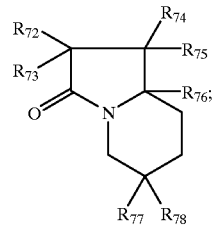

$R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$, $R_{76}$, $R_{77}$ and $R_{78}$ independently of one another are hydrogen or $C_1$–$C_4$alkyl;
or a compound of the formula XV

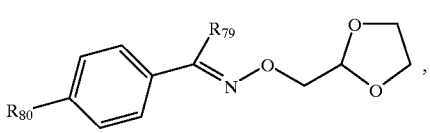

in which
$R_{80}$ is hydrogen or chlorine and $R_{79}$ is cyano or trifluoromethyl, or a compound of the formula XVI

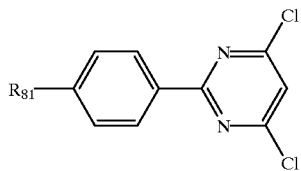

in which
$R_{81}$ is hydrogen or methyl,
or of the formula XVII

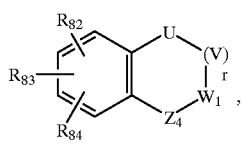

in which
$R_{82}$ is hydrogen, $C_1$–$C_4$alkyl, $C_1$–$C_4$alkyl which is substituted by $C_1$–$C_4$alkyl-$X_2$— or $C_1$–$C_4$haloalkyl-$X_2$—, $C_1$–$C_4$haloalkyl, nitro, cyano, —COOR$_{85}$, —NR$_{86}$R$_{87}$, —SO$_2$NR$_{88}$R$_{89}$ or —CONR$_{90}$R$_{91}$;
$R_{83}$ is hydrogen, halogen, $C_1$–$C_4$alkyl, trifluoromethyl, $C_1$–$C_4$alkoxy or $C_1$–$C_4$haloalkoxy;
$R_{84}$ is hydrogen, halogen or $C_1$–$C_4$alkyl;
U, V, W, and $Z_4$ independently of one another are oxygen, sulfur, C(R$_{92}$)R$_{93}$, carbonyl, NR$_{94}$,

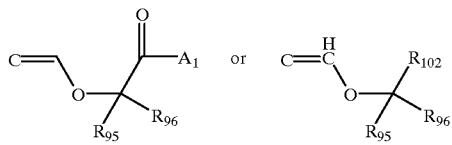

in which $R_{102}$ is $C_2$–$C_4$alkenyl or $C_2$–$C_4$alkynyl;
with the proviso that
a) at least one of the ring members U, V, W, or $Z_4$ is carbonyl, and a ring member which is adjacent to this or these ring members is the group

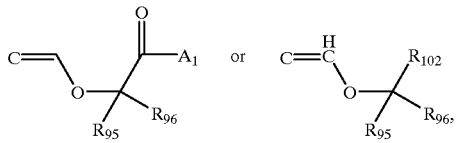

this group being present only once; and
b) two adjacent ring members U and V, V and $W_1$ and $W_1$ and $Z_4$ may not simultaneously be oxygen;
$R_{95}$ and $R_{96}$ independently of one another are hydrogen or $C_1$–$C_8$alkyl; or
$R_{95}$ and $R_{96}$ together form a $C_2$–$C_6$alkylene group;
$A_1$ is $R_{99}$—Y$_1$— or —NR$_{97}$R$_{98}$;
$X_2$ is oxygen or —S(O)$_s$;
$Y_1$ is oxygen or sulfur;
$R_{99}$ is hydrogen, $C_1$–$C_8$alkyl, $C_1$–$C_8$haloalkyl, $C_1$–$C_4$alkoxy-$C_1$–$C_8$alkyl, $C_3$–$C_6$alkenyloxy-$C_1$–$C_8$alkyl or phenyl-$C_1$–$C_8$alkyl, where the phenyl ring may be substituted by halogen, $C_1$–$C_4$alkyl, trifluoromethyl, methoxy or methyl-$S(O)_5$—, $C_3$–$C_6$alkenyl, $C_3$–$C_6$haloalkenyl, phenyl-$C_3$–$C_6$alkenyl, $C_3$–$C_6$alkynyl, phenyl-$C_3$–$C_6$alkynyl, oxetanyl, furyl or tetrahydrofuryl;

$R_{85}$ is hydrogen or $C_1$–$C_4$alkyl;

$R_{86}$ is hydrogen, $C_1$–$C_4$alkyl or $C_1$–$C_4$alkylcarbonyl;

$R_{87}$ is hydrogen or $C_1$–$C_4$alkyl; or $R_{86}$ and $R_{87}$ together form a $C_4$- or $C_5$alkylene group;

$R_{88}$, $R_{89}$, $R_{90}$ and $R_{91}$ independently of one another are hydrogen or $C_1$–$C_4$alkyl; or $R_{88}$ together with $R_{89}$ or $R_{90}$ together with $R_{91}$ independently of one another are $C_4$- or $C_5$-alkylene, where a carbon atom may be replaced by oxygen or sulfur, or one or two carbon atoms may be replaced by —$NR_{100}$—;

$R_{92}$, $R_{100}$ and $R_{93}$ independently of one another are hydrogen or $C_1$–$C_8$alkyl; or $R_{92}$ and $R_{93}$ together are $C_2$–$C_6$alkylene;

$R_{94}$ is hydrogen or $C_1$–$C_8$alkyl;

$R_{97}$ is hydrogen, $C_1$–$C_8$alkyl, phenyl, phenyl-$C_1$–$C_8$alkyl, where the phenyl rings may be substituted by fluorine, chlorine, bromine, nitro, cyano, —$OCH_3$, $C_1$–$C_4$alkyl or $CH_3SO_2$—, $C_1$–$C_4$alkoxy-$C_1$–$C_8$alkyl, $C_3$–$C_6$alkenyl or $C_3$–$C_6$alkynyl;

$R_{98}$ is hydrogen, $C_1$–$C_8$alkyl, $C_3$–$C_6$alkenyl or $C_3$–$C_6$alkynyl; or $R_{97}$ and $R_{98}$ together are $C_4$- or $C_5$-alkylene, where a carbon atom may be replaced by oxygen or sulfur, or one or two carbon atoms may be replaced by —$NR_{101}$—;

$R_{101}$ is hydrogen or $C_1$–$C_4$alkyl;

r is 0 or 1; and s is 0, 1 or 2, or a compound of the formula XVIII

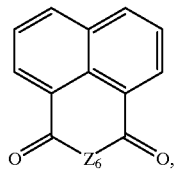

(XVIII)

in which $R_{103}$ is hydrogen, $C_1$–$C_6$alkyl, $C_3$–$C_6$cycloalkyl, $C_3$–$C_6$alkenyl or $C_3$–$C_6$alkynyl; and $R_{104}$, $R_{105}$ and $R_{106}$ independently of one another are hydrogen, $C_1$–$C_6$alkyl, $C_3$–$C_6$cycloalkyl or $C_1$–$C_6$alkoxy, with the proviso that one of the substituents $R_{104}$, $R_{105}$ and $R_{106}$ is different from hydrogen;

a compound of the formula XIX

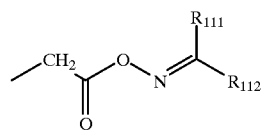

(XIX)

in which $Z_5$ is N or CH, n, in the case where $Z_5$ is N, is 0, 1, 2 or 3 and, in the case where $Z_5$ is CH, is 0, 1, 2, 3 or 4, $R_{107}$ is halogen, $C_1$–$C_4$alkyl, $C_1$–$C_4$haloalkyl, $C_1$–$C_4$alkoxy, $C_1$–$C_4$haloalkoxy, nitro, $C_1$–$C_4$alkylthio, $C_1$–$C_4$alkylsulfonyl, $C_1$–$C_4$alkoxycarbonyl or unsubstituted or substituted phenyl or phenoxy, $R_{108}$ is hydrogen or $C_1$–$C_4$alkyl, $R_{109}$ is hydrogen, $C_1$–$C_4$alkyl, $C_3$–$C_6$cycloalkyl, $C_2$–$C_6$alkenyl, $C_2$–$C_6$alkynyl, $C_1$–$C_4$haloalkyl, $C_2$–$C_6$haloalkenyl, $C_2$–$C_6$haloalkynyl, $C_1$–$C_4$alkylthio-$C_1$–$C_4$alkyl, $C_1$–$C_4$alkylsulfonyl-$C_1$–$C_4$alkyl, $C_1$–$C_4$alkoxy-$C_1$–$C_4$alkyl, $C_1$–$C_4$alkenyloxy-$C_1$–$C_4$alkyl or $C_1$–$C_4$alkynyloxy-$C_1$–$C_4$alkyl;

a compound of the formula XX

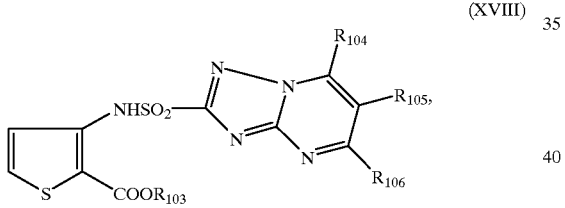

(XX)

in which $Z_6$ is O or N—$R_{110}$ and $R_{110}$ is a group of the formula

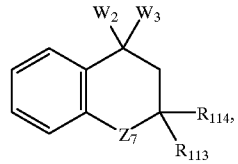

in which $R_{111}$ and $R_{112}$ independently of one another are cyano, hydrogen, $C_1$–$C_4$alkyl, $C_3$–$C_6$cycloalkyl, $C_2$–$C_6$alkenyl, unsubstituted or substituted phenyl or heteroaryl;

compound of the formula XXI

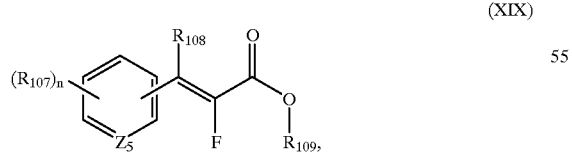

(XXI)

in which $Z_7$ is O, S, S=O, $SO_2$ or $CH_2$, $R_{113}$ and $R_{114}$ independently of one another are hydrogen, halogen or $C_1$–$C_4$alkyl, $W_2$ and $W_3$ independently of one another are $CH_2COOR_{115}$, $COOR_{115}$ or together are a group of the formula —$(CH_2)C(O)$—O—$C(O)$—$(CH_2)$—, and $R_{115}$ is hydrogen, $C_1$–$C_4$alkyl, $C_2$–$C_4$alkenyl, $C_2$–$C_6$alkynyl, $C_3$–$C_6$cycloalkyl, $C_1$–$C_4$haloalkyl, a metal cation or an ammonium cation;

a compound of the formula XXII

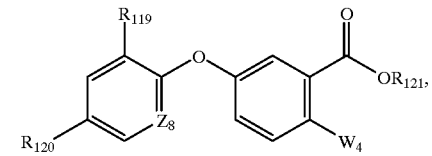

(XXII)

in which $R_{119}$ and $R_{120}$ independently of one another are hydrogen, halogen or $C_1$–$C_4$haloalkyl, $R_{121}$ is hydrogen, $C_1$–$C_4$alkyl, $C_3$–$C_4$alkenyl, $C_3$–$C_4$alkynyl, $C_1$–$C_4$haloalkyl, $C_3$–$C_6$cycloalkyl, a metal cation or an ammonium cation, $Z_8$ is N, CH, C—F or C—Cl and $W_4$ is a group of the formula

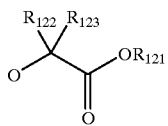 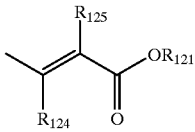

in which $R_{122}$ and $R_{123}$ independently of one another are hydrogen or $C_1$–$C_4$alkyl and $R_{124}$ and $R_{125}$ independently of one another are hydrogen or $C_1$–$C_4$alkyl;

a compound of the formula XXIII

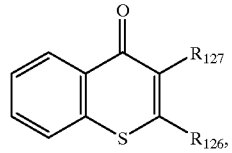

(XXIII)

in which $R_{126}$ is hydrogen, cyano, halogen, $C_1$–$C_4$alkyl, $C_3$–$C_6$cycloalkyl, $C_1$–$C_4$alkoxy, $C_1$–$C_4$alkoxycarbonyl, $C_1$–$C_4$alkylthiocarbonyl, —NH—$R_{128}$, —C(O)NH—$R_{128}$, unsubstituted or substituted aryl or heteroaryl, $R_{127}$ is hydrogen, cyano, nitro, halogen, $C_1$–$C_4$alkyl, $C_1$–$C_4$haloalkyl, $C_1$–$C_4$alkoxy, $C_1$–$C_4$thioalkyl, $C_1$–$C_4$haloalkyl, —NH—$R_{128}$, —C(O)NH—$R_{128}$, unsubstituted or substituted aryl, heteroaryl, and $R_{128}$ is $C_1$–$C_4$alkyl, $C_1$–$C_4$haloalkyl, $C_3$–$C_4$alkenyl, $C_3$–$C_4$alkynyl, $C_3$–$C_4$cycloalkyl, unsubstituted or substituted aryl or heteroaryl, formyl, $C_1$–$C_4$-alkylcarbonyl, $C_1$–$C_4$-alkylsulfonyl;

a compound of the formula XXIV

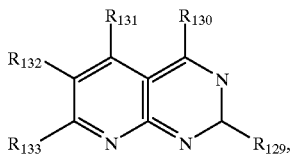

(XXIV)

in which $R_{129}$ and $R_{130}$ independently of one another are hydrogen, $C_1$–$C_4$alkyl, $C_1$–$C_4$haloalkyl, $C_1$–$C_4$alkoxy, mono-$C_1$–$C_8$- or di-$C_1$–$C_8$alkylamino, $C_3$–$C_6$cycloalkyl, $C_1$–$C_4$thioalkyl, phenyl or heteroaryl, $R_{131}$ has the meaning of $R_{129}$ and is additionally OH, $NH_2$, halogen, di-$C_1$–$C_4$aminoalkyl, $C_1$–$C_4$alkylthio, $C_1$–$C_4$alkylsulfonyl or $C_1$–$C_4$alkoxycarbonyl, $R_{132}$ has the meaning of $R_{129}$ and is additionally cyano, nitro, carboxyl, $C_1$–$C_4$alkoxycarbonyl, di-$C_1$–$C_4$aminoalkyl, $C_1$–$C_4$alkylthio, $C_1$–$C_4$alkylsulfonyl, $SO_2$—OH, iso- $C_1$–$C_4$aminoalkylsulfonyl or $C_1$–$C_4$alkoxysulfonyl, $R_{133}$ has the meaning of $R_{129}$ and is additionally OH, $NH_2$, halogen, di-$C_1$–$C_4$aminoalkyl, pyrrolidin-1-yl, piperidin-1-yl, morpholin-1-yl, $C_1$–$C_4$alkylthio, $C_1$–$C_4$alkylsulfonyl, $C_1$–$C_4$alkoxycarbonyl, phenoxy, naphtoxy, phenylamino, benzoyloxy or phenylsulfonyloxy;

or a compound of the formula XXV

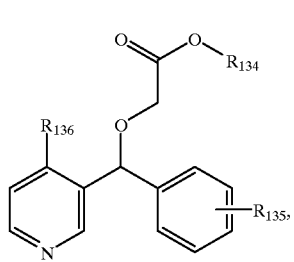

(XXV)

in which $R_{134}$ is hydrogen, $C_4$alkyl, $C_1$–$C_4$haloalkyl, $C_2$–$C_4$alkenyl, $C_2$–$C_4$alkynyl or $C_1$–$C_4$alkoxy-$C_1$–$C_4$alkyl, $R_{135}$ is hydrogen, halogen, $C_1$–$C_4$alkyl, $C_1$–$C_4$haloalkyl or $C_1$–$C_4$alkoxy and $R_{136}$ is hydrogen, halogen, $C_1$–$C_4$alkyl, $C_1$–$C_4$haloalkyl or $C_1$–$C_4$alkoxy, with the proviso that $R_{135}$ and $R_{136}$ are not simultaneously hydrogen.

The selective-herbicidal composition according to the invention preferably comprises, as herbicide-antagonistically effective amount, either a compound of the formula X

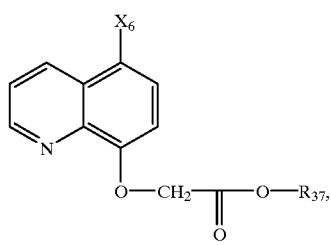

(X)

in which $R_{37}$ is hydrogen, $C_1$–$C_6$alkyl or $C_1$–$C_6$alkoxy- or $C_3$–$C_6$alkenyloxy-substituted $C_1$–$C_8$alkyl; and $X_6$ is hydrogen or chlorine; or a compound of the formula XI

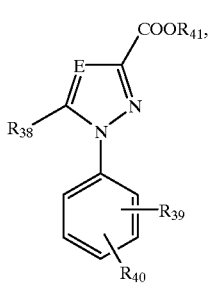

(XI)

in which

E is nitrogen or methine; $R_{38}$ is —$CCl_3$, phenyl or halogen-substituted phenyl;

$R_{39}$ and $R_{40}$ independently of one another are hydrogen or halogen; and $R_{41}$ is $C_1$–$C_4$alkyl; or a compound of the formula XII

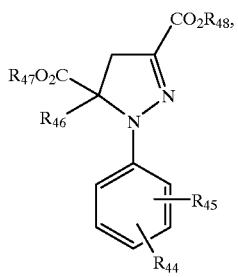

(XII)

in which

R$_{44}$ and R$_{45}$ independently of one another are hydrogen or halogen and R$_{46}$, R$_{47}$ and R$_{48}$ independently of one another are C$_1$–C$_4$alkyl.

The abovementioned preferences for the compounds of the formula I also apply to mixtures of the compounds of the formula I with safeners of the formulae X to XVIII. Preferred compositions according to the invention comprise a safener selected from the group consisting of the formula Xa

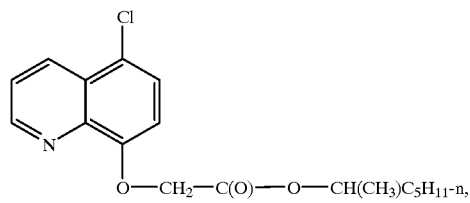

(Xa)

the formula Xb (Xb)

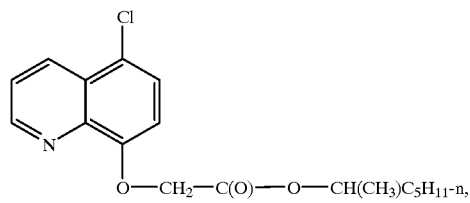

and the formula XIa

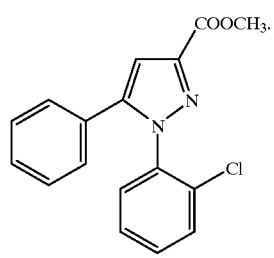

(XIa)

Other preferred compounds of the formulae X, XI and XII are also listed in Tables 9, 10 and 11.

TABLE 9

Compounds of the formula X:

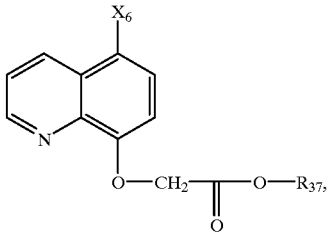

(X)

| Comp. No. | X$_6$ | R$_{37}$ |
|---|---|---|
| 9.01 | Cl | —CH(CH$_3$)—C$_5$H$_{11}$-n |
| 9.02 | Cl | —CH(CH$_3$)—CH$_2$CH$_2$OCH$_2$CH=CH$_2$ |
| 9.03 | Cl | H |
| 9.04 | Cl | C$_4$H$_9$-n |

Preferred compounds of the formula XI are listed in Table 10 below.

TABLE 10

Compounds of the formula XI:

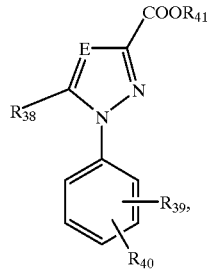

(XI)

| Comp. No. | R$_{41}$ | R$_{38}$ | R$_{39}$ | R$_{40}$ | E |
|---|---|---|---|---|---|
| 10.01 | CH$_3$ | phenyl | 2-Cl | H | CH |
| 10.02 | CH$_3$ | phenyl | 2-Cl | 4-Cl | CH |
| 10.03 | CH$_3$ | phenyl | 2-F | H | CH |
| 10.04 | CH$_3$ | 2-chlorophenyl | 2-F | H | CH |
| 10.05 | C$_2$H$_5$ | CCl$_3$ | 2-Cl | 4-Cl | N |
| 10.06 | CH$_3$ | phenyl | 2-Cl | 4-CF$_3$ | N |
| 10.07 | CH$_3$ | phenyl | 2-Cl | 4-CF$_3$ | N |

Preferred compounds of the formula XII are listed in Table 11 below.

TABLE 11

Compounds of the formula XII:

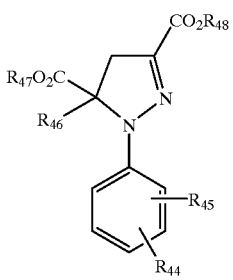

(XII)

| Comp. No. | $R_{46}$ | $R_{47}$ | $R_{48}$ | $R_{44}$ | $R_{45}$ |
|---|---|---|---|---|---|
| 11.01 | $CH_3$ | $CH_3$ | $CH_3$ | 2-Cl | 4-Cl |
| 11.02 | $CH_3$ | $C_2H_5$ | $CH_3$ | 2-Cl | 4-Cl |
| 11.03 | $CH_3$ | $C_2H_5$ | $C_2H_5$ | 4-Cl | 4-Cl |

Preferred compounds of the formula XII are listed in Table 12 below as compounds of the formula XIIIa:

TABLE 12

Compounds of the formula XIIIa:

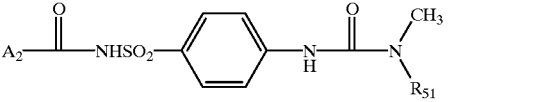

(XIIIa)

| Comp. No. | $A_2$ | $R_{51}$ |
|---|---|---|
| 12.001 | ![2-methoxyphenyl] | H |
| 12.002 | ![2,4-dimethylphenyl] | H |
| 12.003 | ![methylnaphthyl] | $CH_3$ |
| 12.004 | ![2-methoxyphenyl] | $CH_3$ |

Preferred compounds of the formula XIV are listed in Table 13 below:

TABLE 13

Compounds of the formula XIV:

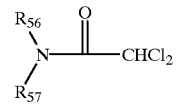

(XIV)

| Comp. No. | $R_{56}$ | $R_{57}$ | $R_{56} + R_{57}$ |
|---|---|---|---|
| 13.001 | $CH_2=CHCH_2$ | $CH_2=CHCH_2$ | — |
| 13.002 | — | — | 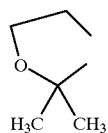 |
| 13.003 | — | — | 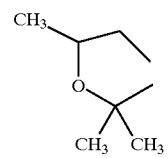 |
| 13.004 | — | — | 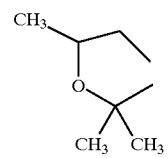 |
| 13.005 | — | — | 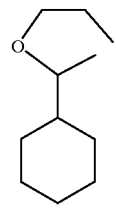 |
| 13.006 | — | — | 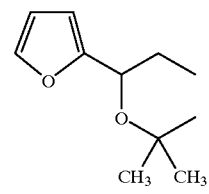 |
| 13.007 | — | — | 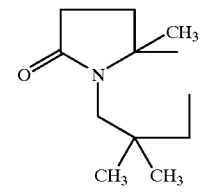 |

TABLE 13-continued

Compounds of the formula XIV:

(XIV)

| Comp. No. | $R_{56}$ | $R_{57}$ | $R_{56} + R_{57}$ |
|---|---|---|---|
| 13.008 | — | — | (spirocyclohexyl-methyldioxolane structure) |

Preferred compounds of the formula XV are listed in Table 14 below:

TABLE 14

Compounds of the formula XV:

(XV)

| Comp. No. | $R_{80}$ | $R_{79}$ |
|---|---|---|
| 14.01 | H | CN |
| 14.02 | Cl | $CF_3$ |

Preferred compounds of the formula XVI are listed in Table 15 below:

TABLE 15

Compounds of the formula XVI:

(XVI)

| Comp. No. | $R_{81}$ |
|---|---|
| 15.01 | H |
| 15.02 | $CH_3$ |

Preferred compounds of the formula XVII are listed in Table 16 below as compounds of the formula XVIIa:

TABLE 16

Compounds of the formula (XVIIa)

(XVIIa)

| Comp. No. | $R_{82}$ | $Z_4$ | V | r |
|---|---|---|---|---|
| 16.001 | H | C=CH—O—CH$_2$—C(H)=CH$_2$ | O | 1 |
| 16.002 | H | C=CH—O—CH$_2$—COOCH$_3$ | O | 1 |
| 16.003 | H | C=CH—O—CH$_2$—C≡CH | O | 1 |
| 16.004 | H | C=CH—O—CH$_2$—COOCH(CH$_3$)(CH$_2$)$_4$CH$_3$ | O | 1 |
| 16.005 | H | C=CH—O—CH$_2$—COOCH$_3$ | $CH_2$ | 1 |
| 16.006 | H | C=CH—O—CH(CH$_3$)—COOCH$_3$ | $CH_2$ | 1 |
| 16.007 | H | C=CH—O—CH$_2$—COOCH$_3$ | S | 1 |
| 16.008 | H | C=CH—O—CH$_2$—C≡CH | S | 1 |
| 16.009 | H | C=CH—O—CH$_2$—C≡CH | $NCH_3$ | 1 |
| 16.010 | H | C=CH—O—CH$_2$—COOCH$_3$ | $NCH_3$ | 1 |
| 16.011 | H | C=CH—O—CH(CH$_3$)—COOCH$_3$ | $NCH_3$ | 1 |
| 16.012 | H | C=CH—O—CH(CH$_3$)—COOCH$_3$ | O | 1 |
| 16.013 | H | C=CH—O—CH(CH$_3$)—COOCH$_3$ | S | 1 |

Preferred compounds of the formula XVII are listed in Table 17 below as compounds of the formula XVIIb:

TABLE 17

Compounds of the formula XVIIb (XVIIb): R₈₂-substituted benzofuran-2(3H)-one-like structure with U at position linking to C=O, and Z₄ group

| Comp. No. | U | R₈₂ | Z₄ |
|---|---|---|---|
| 17.001 | O | H | C=CH–O–CH₂–COOCH₃ |
| 17.002 | O | H | C=CH–O–CH₂–C≡CH |
| 17.003 | O | 5-Cl | C=CH–O–CH₂–COOCH₃ |
| 17.004 | CH₂ | H | C=CH–O–CH₂–COOCH₃ |
| 17.005 | CH₂ | H | C=CH–O–CH₂–COO–CH₂–C₆H₅ |
| 17.006 | CH₂ | H | C=CH–O–CH₂–COOC₂H₅ |
| 17.007 | NH | 5-Cl | C=CH–O–CH(CH₃)–COOCH₃ |
| 17.008 | NH | 5-Cl | C=CH–O–CH₂–COOCH₃ |
| 17.009 | NH | H | C=CH–O–CH₂–COOCH₃ |
| 17.010 | NH | H | C=CH–O–CH(CH₃)–COOCH₃ |
| 17.011 | NCH₃ | H | C=CH–O–CH(CH₃)–COOCH₃ |
| 17.012 | NCH₃ | H | C=CH–O–CH₂–COOCH₃ |

Preferred compounds of the formula XVII are listed in Table 18 below as compounds of the formula XVIIc:

TABLE 18

Compounds of the formula XVIIc (XVIIc)

| Comp. No. | U | V | r | W₁ | Z₄ | R₈₂ |
|---|---|---|---|---|---|---|
| 18.001 | O | C=O | 1 | C=CH–O–CH₂–C≡CH | CH₂ | H |
| 18.002 | O | C=O | 1 | C=CH–O–CH₂–COOCH₃ | CH₂ | H |
| 18.003 | CH₂ | C=O | 1 | C=CH–O–CH(CH₃)–COOCH₃ | CH₂ | H |
| 18.004 | CH₂ | C=O | 1 | C=CH–O–CH₂–COOCH₃ | CH₂ | H |
| 18.005 | CH₂ | CH₂ | 1 | C=CH–O–CH₂–COOCH₃ | C=O | H |
| 18.006 | CH₂ | CH₂ | 1 | C=CH–O–CH(CH₃)–COOCH₃ | C=O | H |
| 18.007 | NCH₃ | C=O | 1 | C=CH–O–CH₂–COOCH₃ | CH₂ | H |

Preferred compounds of the formula XVII are listed in Table 19 below as compounds of the formula XVIId:

TABLE 19

Compounds of the formula XVIId (XVIId)

| Comp. No. | R₈₂ | W₁ |
|---|---|---|
| 19.001 | 6-Cl | C=CH–O–CH₂–COOCH₃ |
| 19.002 | 6-Cl | C=CH–O–CH(CH₃)–COOCH₃ |

TABLE 19-continued

Compounds of the formula XVIId (XVIId)

| Comp. No. | $R_{82}$ | $W_1$ |
|---|---|---|
| 19.003 | H | C=CH–O–C(CH$_3$)–C≡CH |
| 19.004 | H | C=CH–O–CH(CH$_3$)–COOCH$_3$ |
| 19.005 | H | C=CH–O–CH$_2$–COOCH$_3$ |

Preferred compounds of the formula XVIII are listed in Table 20 below:

TABLE 20

Compounds of the formula XVIII (XVIII)

| Comp. No. | $R_{103}$ | $R_{104}$ | $R_{105}$ | $R_{106}$ |
|---|---|---|---|---|
| 20.01 | CH$_3$ | H | cyclopropyl | H |
| 20.02 | CH$_3$ | C$_2$H$_5$ | cyclopropyl | H |
| 20.03 | CH$_3$ | cyclopropyl | C$_2$H$_5$ | H |
| 20.04 | CH$_3$ | CH$_3$ | H | H |
| 20.05 | CH$_3$ | CH$_3$ | cyclopropyl | H |
| 20.06 | CH$_3$ | OCH$_3$ | OCH$_3$ | H |
| 20.07 | CH$_3$ | CH$_3$ | OCH$_3$ | H |
| 20.08 | CH$_3$ | OCH$_3$ | CH$_3$ | H |
| 20.09 | CH$_3$ | CH$_3$ | CH$_3$ | H |
| 20.10 | C$_2$H$_5$ | CH$_3$ | CH$_3$ | H |
| 20.11 | C$_2$H$_5$ | OCH$_3$ | OCH$_3$ | H |
| 20.12 | H | OCH$_3$ | OCH$_3$ | H |
| 20.13 | H | CH$_3$ | CH$_3$ | H |
| 20.14 | C$_2$H$_5$ | H | H | CH$_3$ |
| 20.15 | H | H | H | CH$_3$ |
| 20.16 | CH$_3$ | H | H | CH$_3$ |
| 20.17 | CH$_3$ | CH$_3$ | H | CH$_3$ |

The invention also relates to a method for the selective control of weeds in crops of useful plants which comprises treating the useful plants, their seeds or seedlings or the area on which they are cultivated jointly or separately with a herbicidally effective amount of the herbicide of the formula I and a herbicide-antagonistically effective amount of the safener of the formula X, XI, XII, XIII, XIV, XV, XVI, XVII or XVIII.

Crop plants which can be protected against the damaging effect of the abovementioned herbicides by the safeners of the formula X, XI, XII, XIII, XIV, XV, XVI, XVII or XVIII are, in particular, cereals, cotton, soya, sugarbeet, sugarcane, plantings, rapeseed, maize and rice, very particularly maize and cereals. Crops are to be understood as including those which have been rendered tolerant towards herbicides or classes of herbicides by conventional breeding methods or genetical engineering methods.

The weeds to be controlled can be both monocotyledonous and dicotyledonous weeds, for example the monocotyledonous weeds Avena, Agrostis, Phalaris, Lolium, Bromus, Alopecurus, Setaria, *Digitaria Brachiaria,* Echinochloa, Panicum, *Sorghum hal./bic.,* Rottboellia, Cyperus, Brachiaria, Scirpus, Monochoria, Sagittaria, and Stellaria and the dicotyledonous weeds Sinapis, Chenopodium, Galium, Viola, Veronica, Matricaria, Papaver, Solanum, Abutilon, Sida, Xanthium, Amaranthus, Ipomoea and Chrysanthemum.

Areas under cultivation are the areas on which the crop plants are already growing, or on which the seeds of these crop plants have been sown, and also the soils which are intended to be cultivated with these crop plants.

Depending on the intended use, a safener of the formula X, XI, XII, XIII, XIV, XV, XVI, XVII or XVIII can be employed for pretreating the seeds of the crop plant (dressing of the seeds or the seedlings), or it can be worked into the soil before or after seeding. However, it can also be applied on its own or together with the herbicide after the plants have emerged. Thus, the treatment of the plants or the seeds with the safener can, in principle, be carried out independently of when the herbicide is applied. However, the plant can also be treated by simultaneous application of herbicide and safener (for example as tank mix). The application rate of safener to herbicide to be applied depends essentially on the type of application. In a field treatment which is carried out either by using a tank mix of a combination of safener and herbicide or by separate application of safener and herbicide, the ratio of herbicide to safener is as a rule from 100:1 to 1:10, preferably from 20:1 to 1:1. As a rule, 0.001 to 1.0 kg of safener/ha, preferably 0.001 to 0.25 kg of safener/ha are applied in the field treatment.

The application rates of herbicide are as a rule between 0.001 and 2 kg/ha, but preferably between 0.005 to 0.5 kg/ha.

The compositions according to the invention are suitable for all application methods which are customary in agriculture, for example preemergence application, postemergence application and seed dressing.

For seed dressing, generally 0.001 to 10 g of safener/kg of seed, preferably 0.05 to 2 g of safener/kg of seed, are applied. If the safener is applied in liquid form while swelling the seeds shortly before seeding, it is advantageous to employ safener solutions which comprise the active compound in a concentration of from 1 to 10000, preferably from 100 to 1000, ppm.

For application, the safeners of the formula X, XI, XII, XIII, XIV, XV, XVI, XVII or XVIII or combinations of these safeners with the herbicides of the formula I are advantageously processed together with auxiliaries conventionally used in the art of formulation, for example to give emulsion concentrates, spreadable pastes, directly sprayable or dilutable solutions, dilute emulsions, wettable powders, soluble powders, dusts, granules or microcapsules.

Such formulations are described, for example, in WO 97/34485 on pages 9 to 13. The formulations are prepared in a known manner, for example by intimate mixing and/or grinding of the active compounds with liquid or solid formulation auxiliaries, for example solvents or solid carriers. Surface-active compounds (surfactants) can furthermore additionally be used during preparation of the formulations. Solvents and solid carriers which are suitable for this purpose are mentioned, for example, in WO 97/34485 on page 6.

Suitable surface-active compounds are, depending on the nature of the active compound of the formula I to be formulated, nonionic, cationic and/or anionic surfactants and surfactant mixtures having good emulsifying, dispersing and wetting properties. Examples of suitable anionic, nonionic and cationic surfactants are listed, for example, in WO 97/34485 on pages 7 and 8. The surfactants conventionally used in the art of formulation and which can also be used in the preparation of the herbicidal compositions according to the invention are described, inter alia, in "Mc Cutcheon's Detergents and Emulsifiers Annual", MC Publishing Corp., Ridgewood N.J., 1981, Stache, H., "Tensid-Taschenbuch" [Surfactant handbook], Carl Hanser Verlag, Munich/Vienna, 1981 and M. and J. Ash, "Encyclopedia of Surfactants", Vol I-III, Chemical Publishing Co., New York, 1980–81.

The herbicidal formulations as a rule comprise 0.1 to 99% by weight, in particular 0.1 to 95% by weight, of the active compound mixture of the compound of the formula I with the compounds of the formulae X, XI, XII, XIII, XIV, XV, XVI, XVII or XVIII, 1 to 99.9% by weight of a solid or liquid formulation auxiliary and 0 to 25% by weight, in particular 0.1 to 25% by weight, of a surfactant. While concentrated compositions are usually preferred as commercial goods, the end user as a rule uses dilute compositions.

The compositions can also comprise further additives, such as stabilizers, for example epoxidized or non-epoxidized vegetable oils (epoxidized coconut oil, rapeseed oil or soya oil), defoamers, for example silicone oil, preservatives, viscosity regulators, binders, tackifiers and fertilizers or other active substances. For using safeners of the formula X, XI, XII, XIII, XIV, XV, XVI, XVII or XVIII or compositions comprising them to protect crop plants against damaging effects of herbicides of the formula I, various methods and techniques are suitable, for example the following:

i) Seed Dressing a) Dressing the seeds with an active compound of the formula X, XI, XII, XII, XIV, XV, XVI, XVII or XVIII formulated as a wettable powder by shaking in a vessel until even distribution on the surface of the seeds is achieved (dry dressing). Here, approximately 1 to 500 g of active compound of the formula X, XI, XII, XII, XIV, XV, XVI, XVII or XVIII (4 g to 2 kg of wettable powder) are employed per 100 kg of seed.

b) Dressing the seeds using an emulsion concentrate of the active compound of the formula X, XI, XII, XII, XIV, XV, XVI, XVII or XVIII according to method a) (wet dressing).

c) Dressing by dipping the seeds for 1 to 72 hours into a liquor containing 1–1000 ppm of active compound of the formula X, XI, XII, XIII, XIV, XV, XVI, XVII or XVIII, with or without subsequent drying of the seeds (dip dressing).

Seed dressing or the treatment of the germinated seedling are the naturally preferred application methods, since the treatment with active compound is completely directed at the target culture. As a rule, 1 to 1000 g of antidote, preferably 5 to 250 g of antidote, are employed per 100 kg of seed, but, depending on the method, which also permits the addition of other active compounds or micronutrients, it is possible to deviate above or below the stated limit concentrations (repeat dressing).

ii) Application as Tank Mix

A liquid preparation of a mixture of antidote and herbicide (mutual ratio between 10:1 and 1:100) is employed, the application rate of herbicide being from 0.005 to 5.0 kg per hectare. Such tank mixes are applied before or after seeding.

iii) Application in the Seed Farrow

The active compound of the formula X, XI, XII, XIII, XIV, XV, XVI, XVII or XVIII is applied into the open seeded seed farrow as an emulsion concentrate, a wettable powder or as granules. After the seed farrow has been covered, the herbicide is applied in a customary manner by the pre-emergence method.

iv) Controlled Release of Active Compound

The active compound of the formula X, XI, XII, XIII, XIV, XV, XVI, XVII or XVIII is absorbed in solution onto mineral granule carriers or polymerized granules (urea/formaldehyde) and dried. If appropriate, a coating which allows the active compound to be released in metered form over a certain period of time can be applied (coated granules).

The efficacy of herbicidal and plant-growth-inhibiting compositions according to the invention comprising a herbicidally effective amount of a compound of the formula I and a herbicide-antagonistically effective amount of a compound of the formula X, XI, XII, XIII, XIV, XV, XVI, XVII or XVIII can be increased by addition of spray tank adjuvants. These adjuvants may be, for example, nonionic surfactants, mixtures of nonionic surfactants, mixtures of anionic surfactants with nonionic surfactants, cationic surfactants, organosilicon surfactants, mineral oil derivatives with or without surfactants, vegetable oil derivatives with or without addition of surfactants, alkylated derivatives of oils of vegetable or mineral origin with or without surfactants, fish oils and other oils of animal nature and their alkyl derivatives with or without surfactants, natural higher fatty acids, preferably having 8 to 28 carbon atoms, and their alkyl ester derivatives, organic acids which contain an aromatic ring system and one or more carboxylic esters, and their alkyl derivatives, furthermore suspensions of polymers of vinyl acetate or copolymers of vinyl acetate/acrylic esters. Mixtures of individual adjuvants with one another and in combination with organic solvents may further increase the effect.

Suitable nonionic surfactants are, for example, polyglycol ether derivatives of aliphatic or cycloaliphatic alcohols, saturated or unsaturated fatty acids and alkylphenols, preferably those which may contain 3 to 30 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble polyethylene oxide adducts on polypropylene glycol, ethylenediaminopolypropylene glycol and alkylpolypropylene glycol preferably having 1 to 10 carbon atoms in the alkyl chain which preferably contain 20 to 250 ethylene glycol ether groups and 10 to 100 propylene glycol ether groups. The abovementioned compounds generally contain 1 to 5 ethylene glycol units per propylene glycol unit.

Other examples of nonionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Also suitable are fatty esters of polyoxyethylene sorbitan, for example polyoxyethylene sorbitan trioleate.

Preferred anionic surfactants are, in particular, alkyl sulfates, alkyl sulfonates, alkylaryl sulfonates, alkylated phosphoric acids and their ethoxylated derivatives. The alkyl radicals usually contain 8 to 24 carbon atoms.

Preferred nonionic surfactants are known under the following trade names:

Polyoxyethylene cocoalkylamine (for example AMIET® 105 (Kao Co.)), polyoxyethylene oleylamine (for example AMIET® 415 (Kao Co.)), nonylphenolpolyethoxyethanols, polyoxyethylene stearylamine (for example AMIET® 320 (Kao Co.)), N-polyethoxyethylamines (for example GENAMIN® (Hoechst AG)), N,N,N',N'-tetra (polyethoxypolypropoxyethyl)ethylene diamines (for example TERRONIL® and TETRONIC® (BASF Wyandotte Corp.)), BRIJ® (Atlas Chemicals), ETHYLAN® CD and ETHYLAN® D (Diamond Shamrock), GENAPOL® C, GENAPOL® O, GENAPOL® S and GENAPOL® X080 (Hoechst AG), EMULGEN® 104P, EMULGEN® 109P and EMULGEN® 408 (Kao Co.); DISTY® 125 (Geronazzo), SOPROPHOR® CY 18 (Rhône Poulenc S.A.); NONISOL® (Ciba-Geigy), MRYJ® (ICI); TWEEN® (ICI); EMULSOGEN® (Hoechst AG); AMIDOX® (Stephan Chemical Co.), ETHOMID® (Armak Co.); PLURONIC® (BASF Wyandotte Corp.), SOPROPHOR® 461P (Rhône Poulenc S.A.), SOPROPHOR® 496/P (Rhône Poulenc S.A.), ANTAROX FM-63 (Rhône Poulenc S.A.), SLYGARD 309 (Dow Corning), SILWET 408, SILWET L-7607N (Osi-Specialities).

The cationic surfactants are primarily quaternary ammonium salts which contain, as N-substituents, at least one alkyl radical having 8 to 22 C atoms and, as further substituents, lower nonhalogenated or halogenated alkyl, benzyl or lower hydroxyalkyl radicals. The salts are preferably present as halides, methyl sulfates or ethyl sulfates, for example stearyltrimethylammonium chloride or benzyldi(2-chloroethyl)ethylammonium bromide.

The oils used are either of mineral or natural origin. The natural oils may additionally be of animal or vegetable origin. In the case of animal oils, preference is given, in particular, to derivatives of beef tallow, but fish oils (for example sardine oil) and derivatives thereof are also used. Vegetable oils are mainly seed oils of various origin. Examples of particularly preferred vegetable oils which may be mentioned are coconut, rapeseed or sunflower oils and derivatives thereof.

Surfactants, oils, in particular vegetable oils, derivatives thereof such as alkylated fatty acids and mixtures thereof, for example with preferably anionic surfactants such as alkylated phosphoric acids, alkyl sulfates and alkylaryl sulfonates and higher fatty acids which are customary in formulation and adjuvant technique and which can also be employed in the compositions according to the invention and spray tank solutions thereof are described, inter alia, in "Mc Cutcheon's Detergents and Emulsifiers Annual", MC Publishing Corp., Ridgewood N.J., 1998, Stache, H., "Tensid-Taschenbuch" [Surfactant handbook], Carl Hanser Verlag, Munich/Vienna, 1990, M. and J. Ash, "Encyclopedia of Surfactants", Vol. I-IV, Chemical Publishing Co., New York, 1981–89, G. Kapusta, "A Compendium of Herbicide Adjuvants", Southern Illinois Univ., 1998, L. Thomson Harvey, "A Guide to Agricultural Spray Adjuvants Used in the United States", Thomson Pubns., 1992.

In particular, preferred formulations have the following compositions:
(%=per cent by weight)

| Emulsifiable concentrates: | |
|---|---|
| active compound mixture: | 1 to 90%, preferably 5 to 20% |
| surface-active agent: | 1 to 30%, preferably 10 to 20% |
| liquid carrier: | 5 to 94%, preferably 70 to 85% |
| Dusts: | |
| active compound mixture: | 0.1 to 10%, preferably 0.1 to 5% |
| solid carrier: | 99.9 to 90%, preferably 99.9 to 99% |
| Suspension concentrates: | |
| active compound mixture: | 5 to 75%, preferably 10 to 50% |
| water: | 94 to 24%, preferably 88 to 30% |
| surface-active agent: | 1 to 40%, preferably 2 to 30% |
| Wettable powders: | |
| active compound mixture: | 0.5 to 90%, preferably 1 to 80% |
| surface-active agent: | 0.5 to 20%, preferably 1 to 15% |
| solid carrier material: | 5 to 95%, preferably 15 to 90% |
| Granules: | |
| active compound mixture: | 0.1 to 30%, preferably 0.1 to 15% |
| solid carrier: | 99.5 to 70%, preferably 97 to 85% |

The following examples illustrate the invention in more detail, without limiting it.

Formulation Examples for Mixtures of Herbicides of the Formula I and Safeners of the Formula X, XI, XII, XIII, XIV, XV, XVI, XVII or XVIII (%= Per Cent by Weight)

| F1. Emulsion concentrates | a) | b) | c) | d) |
|---|---|---|---|---|
| Active compound mixture | 5% | 10% | 25% | 50% |
| Ca dodecylbenzenesulfonate | 6% | 8% | 6% | 8% |
| Castor oil polyglycol ether (36 mol of EO) | 4% | — | 4% | 4% |
| Octylphenol polyglycol ether (7–8 mol of EO) | — | 4% | — | 2% |
| Cyclohexanone | — | — | 10% | 20% |
| Arom. hydrocarbon mixture $C_9$–$C_{12}$ | 85% | 78% | 55% | 16% |

Emulsions of any desired concentration can be prepared from such concentrates by dilution with water.

| | a) | b) | c) | d) |
|---|---|---|---|---|
| F2. Solutions | | | | |
| Active compound mixture | 5% | 10% | 50% | 90% |
| 1-Methoxy-3-(3-methoxy-propoxy)propane | — | 20% | 20% | — |
| Polyethylene glycol MW 400 | 20% | 10% | — | — |
| N-Methyl-2-pyrrolidone | — | — | 30% | 10% |
| Arom. hydrocarbon mixture $C_9$–$C_{12}$ | 75% | 60% | — | — |

The solutions are suitable for use in the form of tiny droplets.

| F3. Wettable powders | | | | |
|---|---|---|---|---|
| Active compound mixture | 5% | 25% | 50% | 80% |
| Sodium lignosulfonate | 4% | — | 3% | — |
| Sodium laurylsulfate | 2% | 3% | — | 4% |
| Sodium diisobutylnaphthalene-sulfonate | — | 6% | 5% | 6% |
| Octylphenol polyglycol ether | — | 1% | 2% | — |

| | a) | b) | c) | d) |
|---|---|---|---|---|
| (7–8 mol of EO) | | | | |
| Finely divided silica | 1% | 3% | 5% | 10% |
| Kaolin | 88% | 62% | 35% | — |

The active compound is thoroughly mixed with the additives and ground well in a suitable mill. This gives spray powders which can be diluted with water to give suspensions of any desired concentration.

| F4. Coated granules | a) | b) | c) |
|---|---|---|---|
| Active compound mixture | 0.1% | 5% | 15% |
| Finely divided silica | 0.9% | 2% | 2% |
| Inorg. carrier material (Æ 0.1–1 mm), for example CaCO$_3$ or SiO$_2$ | 99.0% | 93% | 83% |

The active compound is dissolved in methylene chloride, the solution is sprayed onto the carrier and the solvent is subsequently evaporated off under reduced pressure.

| F5. Coated granules | a) | b) | c) |
|---|---|---|---|
| Active compound mixture | 0.1% | 5% | 15% |
| Polyethylene glycol MW 200 | 1.0% | 2% | 3% |
| Finely divided silica | 0.9% | 1% | 2% |
| Inorg. carrier material (Æ 0.1–1 mm), for example CaCO$_3$ or SiO$_2$ | 98.0% | 92% | 80% |

In a mixer, the finely ground active compound is applied evenly to the carrier material moistened with polyethylene glycol. In this manner, dust-free coated granules are obtained.

| F6. Extruder granules | a) | b) | c) | d) |
|---|---|---|---|---|
| Active compound mixture | 0.1% | 3% | 5% | 15% |
| Sodium lignosulfonate | 1.5% | 2% | 3% | 4% |
| Carboxymethylcellulose | 1.4% | 2% | 2% | 2% |
| Kaolin | 97.0% | 93% | 90% | 79% |

The active compound is mixed with the additives, ground and moistened with water. This mixture is extruded and subsequently dried in a stream of air.

| F7. Dusts | a) | b) | c) |
|---|---|---|---|
| Active compound mixture | 0.1% | 1% | 5% |
| Talc mixture | 39.9% | 49% | 35% |
| Kaolin | 60.0% | 50% | 60% |

Ready-to-use dusts are obtained by mixing the active compound with the carriers and grinding the mixture in a suitable mill.

| F8. Suspension concentrates | a) | b) | c) | d) |
|---|---|---|---|---|
| Active compound mixture | 3% | 10% | 25% | 50% |
| Ethylene glycol | 5% | 5% | 5% | 5% |
| Nonylphenol polyglycol ether (15 mol of EO) | — | 1% | 2% | — |
| Sodium lignosulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active compound is intimately mixed with the additives. This gives a suspension concentrate, from which suspensions of any desired concentration can be prepared by dilution with water.

It is often more useful to formulate the active compound of the formula I and the mixing partner of the formula X, XI, XII, XIII, XIV, XV, XVI, XVII or XVIII individually and then to mix them shortly before application in the applicator in the desired mixing ratio as "tank mix" in water.

The capability of the safeners of the formula X, XI, XII, XII, XIV, XV, XVI, XVII or XVIII to protect crop plants against the phytotoxic action of herbicides of the formula I is illustrated in the examples below.

Biological Example 1

Safening Action

Under greenhouse conditions, the test plants are grown in plastic pots until they have reached the 4-leaf-stage. In this stage, both the herbicide on its own and the mixtures of the herbicide with the test substances to be tested as safeners are applied to the test plants.

The application is carried out as an aqueous suspension of the test substances, prepared from a 25% wettable powder (Example F3, b)), using 500 l of water/ha. 3 weeks after the application, the phytotoxic effect of the herbicide on the crop plants, for example maize and cereals, is evaluated using a percentage scale. 100% means that the test plant has died, 0% means no phytotoxic effect.

The results obtained in this test show that the damage to the crop plants caused by the herbicide of the formula I can be considerably reduced using the compounds of the formula X, XI, XII, XIII, XIV, XV, XVI, XVII or XVIII.

The same results are obtained when the mixtures are formulated in accordance with Examples F1, F2 and F4 to F8.

Biological Example 2

Safening of the Compound No. 1.032

Under greenhouse conditions, the test plants are grown in plastic pots until they have reached the 4-leaf-stage. In this stage, both the herbicide on its own and the mixtures of the herbicide with the test substances to be tested as safeners are applied to the test plants. The application is carried out as an aqueous suspension of the test substances, prepared from an emulsion concentrate (EC 100; Example F1) of the herbicides and an emulsion concentrate (EC 100; Example F1) of the safeners (exceptions: the safeners no. 10.05 and 20.17, which are employed as a 25% wettable powder (Example F3, b)). 9 days after the application, the phytotoxic effect of the herbicide on summer wheat and durum wheat is evaluated using a percentage scale (100%: test plant has died; 0%: no phytotoxic effect).

TABLE S2

Safening of the compound no. 1.032

| Herbicide no. + safener no. | 1.032 | | | 1.032 + 10.01 | | | 1.032 + 9.01 | | | 1.032 + 10.05 | | |
|---|---|---|---|---|---|---|---|---|---|---|---|---|
| Application rate (g/ha) | 250 + 0 | 125 + 0 | 60 + 0 | 250 + 60 | 125 + 30 | 60 + 15 | 250 + 60 | 125 + 30 | 60 + 15 | 250 + 60 | 125 + 30 | 60 + 15 |
| Summer wheat | 30 | 20 | 10 | 0 | 0 | 0 | 5 | 0 | 0 | 0 | 0 | 0 |
| Durum wheat | 20 | 5 | 0 | 10 | 5 | 0 | 0 | 0 | 0 | 0 | 0 | 0 |

| Herbicide no. + safener no. | 1.032 | | | 1.032 + 20.17 | | | 1.032 + 9.02 | | | 1.032 + 11.03 | | |
|---|---|---|---|---|---|---|---|---|---|---|---|---|
| Application rate (g/ha) | 250 + 0 | 125 + 0 | 60 + 0 | 250 + 60 | 125 + 30 | 60 + 15 | 250 + 60 | 125 + 30 | 60 + 15 | 250 + 60 | 125 + 30 | 60 + 15 |
| Summer wheat | 30 | 20 | 10 | 10 | 5 | 0 | 0 | 0 | 0 | 0 | 0 | 0 |
| Durum wheat | 20 | 5 | 0 | 0 | 0 | 0 | 0 | 0 | 0 | 0 | 0 | 0 |

Biological Example 3

Safening of the Compound No. 1.025

Under greenhouse conditions, the test plants are grown in plastic pots until they have reached the 4-leaf-stage. In this stage, both the herbicide on its own and the mixtures of the herbicide with the test substances to be tested as safeners are applied to the test plants. The application is carried out as an aqueous suspension of the test substances, prepared from an emulsion concentrate (EC 100; Example F1) of the herbicides and an emulsion concentrate (EC 100; Example F1) of the safeners (exceptions: the safeners no. 10.05 and 20.17, which are employed as a 25% wettable powder (Example F3, b)). 11 days after the application, the phytotoxic effect of the herbicide on summer wheat and durum wheat is evaluated using a percentage scale (100%: test plant has died; 0%: no phytotoxic effect).

TABLE S3

Safening of the compound no. 1.025

| Herbicide no. + safener no. | 1.025 | | | 1.025 + 10.01 | | | 1.025 + 9.01 | | | 1.025 + 10.05 | | |
|---|---|---|---|---|---|---|---|---|---|---|---|---|
| Application rate (g/ha) | 500 + 0 | 250 + 0 | 125 + 0 | 500 + 125 | 250 + 60 | 125 + 30 | 500 + 125 | 250 + 60 | 125 + 30 | 500 + 125 | 250 + 60 | 125 + 30 |
| Summer wheat | 55 | 40 | 10 | 10 | 0 | 0 | 0 | 0 | 0 | 5 | 0 | 0 |
| Durum wheat | 40 | 5 | 0 | 10 | 0 | 0 | 0 | 0 | 0 | 0 | 0 | 0 |

| Herbicide no. + safener no. | 1.025 | | | 1.025 + 20.17 | | | 1.025 + 9.02 | | | 1.025 + 11.03 | | |
|---|---|---|---|---|---|---|---|---|---|---|---|---|
| Application rate (g/ha) | 500 + 0 | 250 + 0 | 125 + 0 | 500 + 125 | 250 + 60 | 125 + 30 | 500 + 125 | 250 + 60 | 125 + 30 | 500 + 125 | 250 + 60 | 125 + 30 |
| Summer wheat | 55 | 40 | 10 | 10 | 5 | 5 | 20 | 5 | 0 | 10 | 5 | 0 |
| Durum wheat | 40 | 5 | 0 | 0 | 0 | 0 | 5 | 0 | 0 | 0 | 0 | 0 |

Biological Example 4

Safening of the Compound No. 1.007

Under greenhouse conditions, the test plants are grown in plastic pots until they have reached the 4-leaf-stage. In this stage, both the herbicide on its own and the mixtures of the herbicide with the test substances to be tested as safeners are applied to the test plants. The application is carried out as an aqueous suspension of the test substances, prepared from an emulsion concentrate (EC 100; Example F1) of the herbicides and an emulsion concentrate (EC 100; Example F1) of the safeners (exceptions: the safeners no.10.05 and 20.17, which are employed as a 25% wettable powder (Example F3, b)). 9 days after the application, the phytotoxic effect of the herbicide on summer wheat and durum wheat is evaluated using a percentage scale (100%: test plant has died; 0%: no phytotoxic effect).

TABLE S4

Safening of the compound no. 1.007

| Herbicide no. + safener no. | 1.007 | | | 1.007 + 10.01 | | | 1.007 + 9.01 | | | 1.007 + 10.05 | | |
|---|---|---|---|---|---|---|---|---|---|---|---|---|
| Application rate(g/ha) | 250 + 0 | 125 + 0 | 60 + 0 | 250 + 60 | 125 + 30 | 60 + 15 | 250 + 60 | 125 + 30 | 60 + 15 | 250 + 60 | 125 + 30 | 60 + 15 |
| Summer wheat | 60 | 60 | 60 | 30 | 20 | 10 | 20 | 10 | 0 | 30 | 20 | 10 |
| Durum wheat | 60 | 60 | 55 | 20 | 10 | 5 | 10 | 5 | 0 | 20 | 10 | 5 |
| Herbicide no. + safener no. | 1.007 | | | 1.007 + 20.17 | | | 1.007 + 9.02 | | | 1.007 + 11.03 | | |
| Application rate (g/ha) | 250 + 0 | 125 + 0 | 60 + 0 | 250 + 60 | 125 + 30 | 60 + 15 | 250 + 60 | 125 + 30 | 60 + 15 | 250 + 60 | 125 + 30 | 60 + 15 |
| Summer wheat | 60 | 60 | 60 | 60 | 60 | 40 | 20 | 10 | 10 | 20 | 10 | 10 |
| Durum wheat | 60 | 60 | 55 | 60 | 50 | 40 | 10 | 5 | 5 | 10 | 5 | 5 |

The following examples illustrate the invention in more detail without limiting it.

PREPARATION EXAMPLES

Example H1

Preparation of (1):

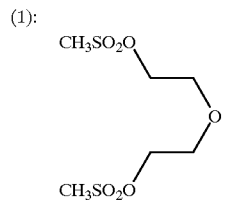

Over a period of one hour, a solution of 177.6 g of methanesulfonyl chloride and 400 ml of diethyl ether is added dropwise to a solution of 80.6 g (0.76 mol) of diethylene glycol and 159.9 g (1.58 mol) of triethylamine in 1500 ml of diethyl ether which had been cooled to −10° C., and during the addition, the temperature is kept below 5° C. The mixture is stirred at a temperature of 0° C. for 30 minutes, and cooling is then removed. After 2 hours, at a temperature of 20° C., 12 ml of triethylamine and 12 ml of methanesulfonyl chloride are added, and stirring is continued for another 4 hours. The resulting white suspension is subsequently transferred onto a suction filter, and the residue is washed twice with 300 ml of diethyl ether. The filter cake is taken up in 2000 ml of ethyl acetate, and the suspension is stirred at room temperature for 30 minutes and then filtered again. The resulting filtrate is concentrated and the residue is used for the next reaction without any further purification. 216.5 g of the desired crude product (1) are obtained in the form of white crystals.

Example H2

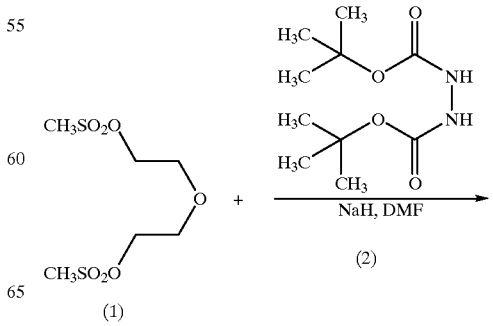

-continued

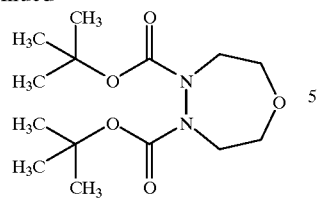

(3)

A solution of 68.78 g (0.30 mol) of (2) in 140 ml of dimethylformamide is added dropwise for a period of 30 minutes to a suspension of 23.9 g (0.60 mol) of 60% sodium hydride in 500 ml of dimethylformamide which had been cooled to 5° C. Cooling is removed and the reaction mixture is stirred until it has reached a temperature of 20° C. The mixture is subsequently briefly heated to a temperature of from 30 to 40° C. to bring the evolution of hydrogen to completion. After cooling to a temperature of from 0 to 5° C., a solution of 80 g (0.305 mol) of (1) in 160 ml of dimethylformamide is added dropwise over a period of 30 minutes, during which the temperature is kept at from 0 to 5° C. Cooling is removed and the reaction mixture is stirred at room temperature for 3 hours and at approximately 40° C. for 45 minutes and then added to a mixture of saturated ammonium chloride solution, ice and tert-butyl methyl ether. The phases are separated and the organic phase is subsequently washed with water (2×). The organic phase is dried with sodium sulfate and evaporated, and the residue is dried further at a temperature of 40° C. and under reduced pressure, giving 92.2 g of (3) in the form of a slightly yellow oil. The crude product is employed for the next reaction without any further purification.

Example H3

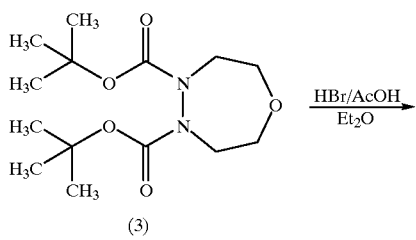

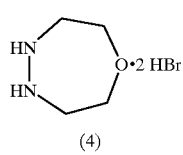

(4)

160.5 ml of a 33% solution of hydrogen bromide in glacial acetic acid are added dropwise over a period of 30 minutes to a solution of 92.2 g (0.305 mol) of (3) in 1200 ml of diethyl ether which had been cooled to 0° C. Cooling is removed and the mixture is subsequently stirred at 20° C. for 22 hours and then under reflux for 27 hours, the resulting white suspension is transferred onto a suction filter and washed with diethyl ether, and the filter residue is subsequently dried over $P_2O_5$ under reduced pressure at a temperature of from 50 to 60° C. The product (4) is obtained in a yield of 52.9 g in the form of a white solid.

Example H4

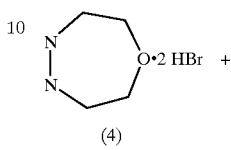

(4)

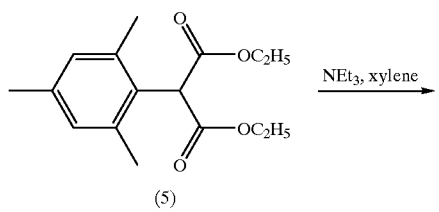

(5)

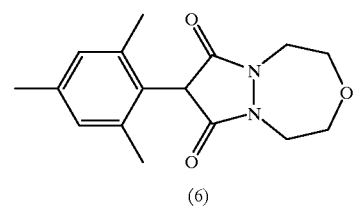

(6)

71.8 g (0.71 mol) of triethylamine are added to a suspension of 40 g (0.15 mol) of (4) in 1000 ml of xylene, and the mixture is degassed (4×vacuum/argon). The yellow suspension is subsequently heated to a temperature of 60° C. and stirred for 3 hours. 42.5 g (0.15 mol) of (5) are then added, and the mixture is heated to a bath temperature of 150° C. to distil off excess triethylamine and the ethanol which is formed. After 3 hours, the reaction mixture is cooled to a temperature of 40° C. and added to 500 ml of an ice/water mixture. Using 100 ml of aqueous 1 N sodium hydroxide solution, the reaction mixture is made alkaline and the aqueous phase (which contains the product) is washed twice with ethyl acetate. The organic phase is reextracted twice using aqueous 1 N sodium hydroxide solution, the aqueous phases are combined, the remaining xylene is distilled off and the combined aquoeus phases are adjusted to pH 2–3 using 4N HCl with cooling. The product which precipitates is transferred onto a suction filter, the filter cake is washed with water and briefly with hexane and is subsequently dried under reduced pressure at a temperature of 60° C. over $P_2O_5$. This gives 34.6 g of (6) as a slightly beige solid of melting point 242–244° C. (decomp.).

Example H5

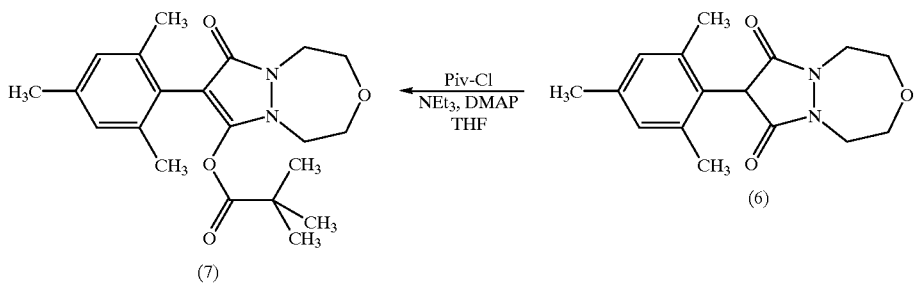

A catalytic amount of 4-dimethylaminopyridine is added to a solution of 3 g (10.4 mmol) of (6) and 1.6 g (15.8 mmol) of triethylamine in 100 ml of tetrahydrofuran which had been cooled to a temperature of 0° C. 1.57 g (13.0 mmol) of pivaloyl chloride are subsequently added dropwise. The mixture is stirred at a temperature of 0° C. for 30 minutes, cooling is removed, and the mixture is stirred for a further 60 minutes. The reaction mixture is subsequently poured into saturated aqueous sodium chloride solution, and the organic phase is separated off. The organic phase is dried over magnesium sulfate, filtered off and concentrated. Chromatographic purification and recrystallization from diethyl ether gives 2.94 g of (7) of melting point 135–136° C.

Example H6

Preparation of (8):

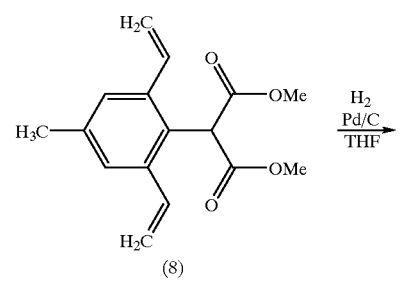

First 36.7 g (0.116 mol) of tributylvinylstannane and then 2 g of tetrakis(triphenylphosphine)palladium are added to a solution of 20 g of dimethyl 2-(2,6-dibromo-4-methyl-phenyl)malonate (52.6 mmol) in 400 ml of toluene (3×degassed, vacuum/argon). The reaction mixture is then stirred at a temperature of from 90 to 95° C. for 9 hours. Filtration through Hyflo and concentration on a rotary evaporator gives, after chromatographic purification, 15.3 g of (8) in the form of a yellow oil which is used for the next reaction without any further purification.

Example H7

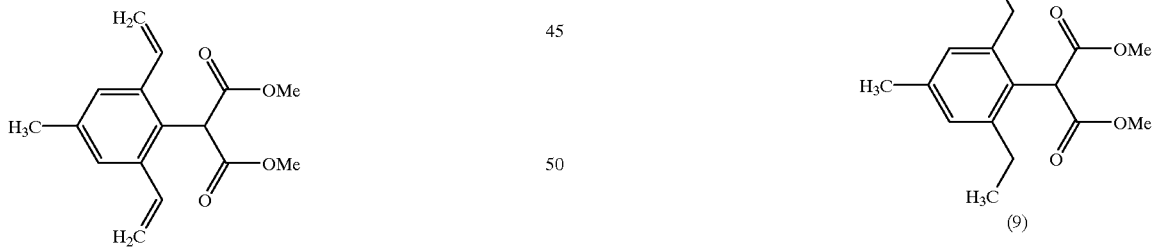

At a temperature of from 20 to 25° C., 15.2 g of the compound (8) obtained according to Example H6 are hydrogenated with hydrogen over a palladium catalyst (using carbon as carrier, 7 g of 5% Pd/C) in 160 ml of tetrahydrofuran. After the hydrogenation has ended, the product is filtered through Hyflo, and the resulting filtrate is concentrated on a rotary evaporator. This gives 13.7 g of (9) in the form of yellow crystals of melting point 47–49° C.

Example H8

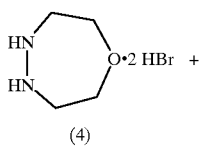

(4)

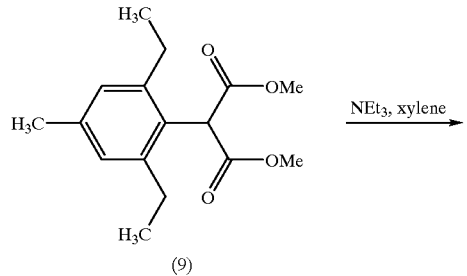

By the method of Preparation Example H4, but starting from 4.8 g (17.2 mmol) of the malonate (9), 4.56 g of the compound (10) are obtained as a solid of melting point 188–190° C.

Example H9

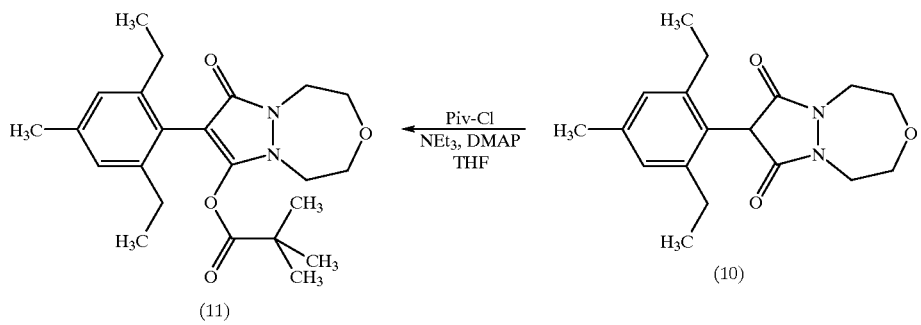

A catalytic amount of 4-dimethylaminopyridine is added to a solution of 1 g (3.2 mmol) of (10) and 0.65 g (6.4 mmol) of triethylamine in 30 ml of tetrahydrofuran which had been cooled to a temperature of 0° C. 0.49 g (4.1 mmol) of pivaloyl chloride is subsequently added dropwise. The mixture is stirred at a temperature of 0° C. for 10 minutes, cooling is removed, and stirring is then continued for a further 90 minutes. The reaction mixture is poured into saturated aqueous sodium chloride solution and diluted with tert-butyl methyl ether, and the organic phase is separated off. The organic phase is dried over magnesium sulfate, filtered off and concentrated. Chromatographic purification gives 1.07 g of (11) in the form of a white solid of melting point 122–123° C.

Example H10

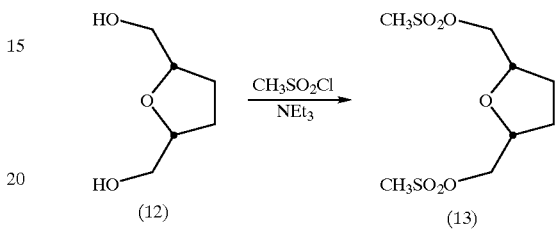

67.8 g (0.59 mol) of methanesulfonyl chloride are added dropwise to a solution of 37.1 g (0.28 mol) of cis-2,5-bis(hydroxymethyl)tetrahydrofuran (12) and 65.3 g (0.65 mol) of triethylamine in 400 ml of methylene chloride which had been cooled to 0–3° C, during which the temperature is kept below 7° C. The mixture is subsequently stirred at a temperature of 20° C. overnight. The resulting white suspension is transferred onto a suction filter, the residue is washed with methylene chloride and the filtrate is concentrated. The residue is taken up in ethyl acetate, washed with water (2×) and with saturated aqueous sodium chloride solution (1×), dried ($Na_2SO_4$) and concentrated. This gives 72.7 g of the dimesylate compound (13) as a crude oil which is employed for the next reaction without any further purification. The starting material (12) is known from the literature: see, for example, K. Naemura et al., Tetrahedron Asymmetry 1993, 4, 911–918.

Example H11

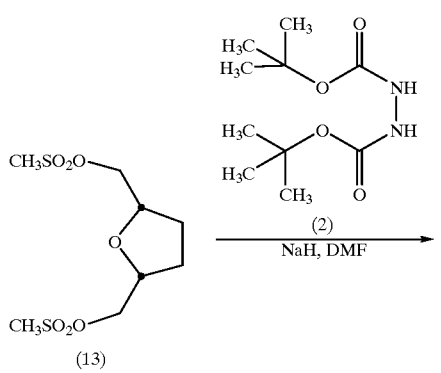

By the method of Preparation Example H2, but starting from 21.0 g (0.53 mol) of 60% NaH, 58.4 g (0.25 mol) of (2) and 72.5 g (0.25 mol) of dimesylate (13) in a total of 840 ml of dimethylformamide, (14) is obtained as a crude brown oil. Chromatographic purification gives 53.7 g of the pure compound (14) as a white solid of melting point 81–83°C.

Example H12

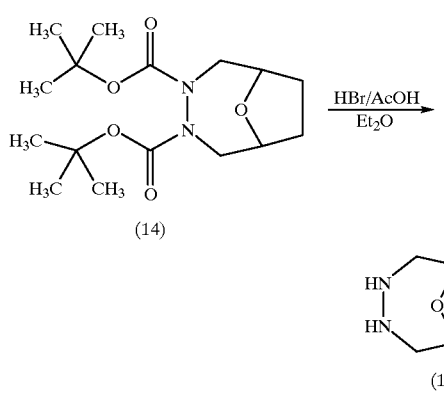

By the method of Preparation Example H3, but starting from 53.5 g (0.16 mol) of (14) in 800 ml of diethyl ether and 90 ml of a 33% solution of hydrogen bromide in conc. acetic acid, 36.5 g of the bicyclic hydrazine (15) are obtained as a solid of melting point 262–264° C.

Example H13

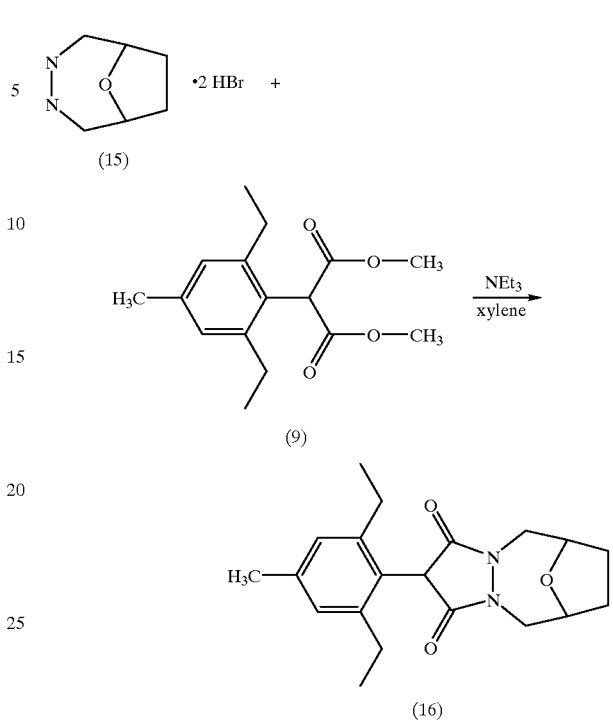

By the method of Preparation Example H4, but starting from 0.105 mol of the malonate (9) and 30.4 g (0.105 mol) of the hydrazine (15), 29.7 g of the compound (16) are obtained as a solid of melting point 287° C.

Example H14

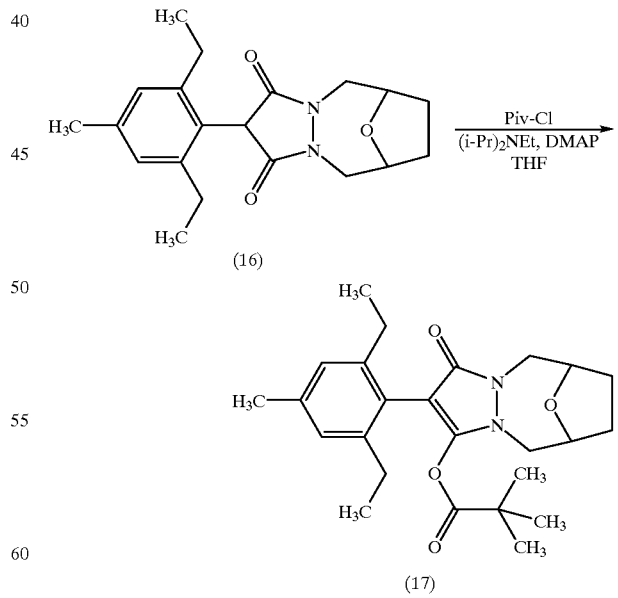

By the method of Preparation Example H9, but starting from 1.1 g (3.2 mmol) of (16), 0.83 g of the pivaloyl ester (17) is obtained as a solid of melting point 141–143° C.

TABLE 1

Compounds of the formula Ie:

(Ie)

| Comp. No. | R$_1$ | R$_2$ | R3 | G | Phys. data |
|---|---|---|---|---|---|
| 1.001 | CH$_3$ | CH$_3$ | CH$_3$ | H | m.p. 245° C. |
| 1.002 | CH$_3$ | CH$_3$ | CH$_3$ | C(O)C(CH$_3$)$_3$ | m.p. 135–136° C. |
| 1.003 | CH$_3$ | CH$_3$ | CH$_3$ | C(O)OCH$_2$CH$_3$ | |
| 1.004 | CH$_2$CH$_3$ | CH$_3$ | CH$_3$ | H | m.p. 182–185° C. |
| 1.005 | CH$_2$CH$_3$ | CH$_3$ | CH$_3$ | C(O)C(CH$_3$)$_3$ | m.p. 110–113° C. |
| 1.006 | CH$_2$CH$_3$ | CH$_3$ | CH$_3$ | C(O)OCH$_2$CH$_3$ | |
| 1.007 | CH$_2$CH$_3$ | CH$_3$ | CH$_2$CH$_3$ | H | m.p. 189–191° C. |
| 1.008 | CH$_2$CH$_3$ | CH$_3$ | CH$_2$CH$_3$ | C(O)C(CH$_3$)$_3$ | m.p. 122–124° C. |
| 1.009 | CH$_2$CH$_3$ | CH$_3$ | CH$_2$CH$_3$ | C(O)OCH$_2$CH$_3$ | m.p. 114–116° C. |
| 1.010 | CH=CH$_2$ | CH$_3$ | CH$_3$ | H | m.p. 165–170° C. |
| 1.011 | CH=CH$_2$ | CH$_3$ | CH$_3$ | C(O)C(CH$_3$)$_3$ | m.p. 111–113° C. |
| 1.012 | CH=CH$_2$ | CH$_3$ | CH$_2$CH$_3$ | H | |
| 1.013 | CH=CH$_2$ | CH$_3$ | CH=CH$_2$ | H | |
| 1.014 | CH=CH$_2$ | CH$_3$ | CH=CH$_2$ | C(O)C(CH$_3$)$_3$ | |
| 1.015 | C≡CH | CH$_3$ | CH$_3$ | H | m.p. 179–184° C. |
| 1.016 | C≡CH | CH$_3$ | CH$_3$ | C(O)C(CH$_3$)$_3$ | m.p. 109–111° C. |
| 1.017 | C≡CH | CH$_3$ | CH$_3$ | C(O)OCH$_2$CH$_3$ | |
| 1.018 | C≡CH | CH$_3$ | CH$_2$CH$_3$ | H | m.p. 189–193° C. |
| 1.019 | C≡CH | CH$_3$ | CH$_2$CH$_3$ | C(O)C(CH$_3$)$_3$ | |
| 1.020 | C≡CH | CH$_3$ | CH$_2$CH$_3$ | C(O)OCH$_2$CH$_3$ | |
| 1.021 | C≡H | CH$_3$ | C≡CH | H | m.p. 300° C. |
| 1.022 | C≡CH | CH$_3$ | CCH | C(O)C(CH$_3$)$_3$ | m.p. 183–185° C. |
| 1.023 | C≡CH | CH$_3$ | C≡CH | C(O)OCH$_2$CH$_3$ | |
| 1.024 | C≡CH | CH$_3$ | CH=CH$_2$ | H | |
| 1.025 | C≡CCH$_3$ | CH$_3$ | CH$_3$ | H | m.p. 179–181° C. |
| 1.026 | C≡CCH$_3$ | CH$_3$ | CH$_3$ | C(O)C(CH$_3$)$_3$ | m.p. 128–129° C. |
| 1.027 | C≡CCH$_3$ | CH$_3$ | CH$_3$ | C(O)OCH$_2$CH$_3$ | |
| 1.028 | C≡CCH$_3$ | CH$_3$ | CH$_2$CH$_3$ | H | |
| 1.029 | C≡CCH$_3$ | CH$_3$ | CH$_2$CH$_3$ | C(O)C(CH$_3$)$_3$ | |
| 1.030 | C≡CCH$_3$ | CH$_3$ | C≡CCH$_3$ | H | |
| 1.031 | C≡CCH$_3$ | CH$_3$ | C≡CCH$_3$ | C(O)C(CH$_3$)$_3$ | |
| 1.032 | CH$_2$CH$_2$CH$_3$ | CH$_3$ | CH$_3$ | H | m.p. 136–138° C. |
| 1.033 | CH$_2$CH$_2$CH$_3$ | CH$_3$ | CH$_3$ | C(O)C(CH$_3$)$_3$ | m.p. 65–67° C. |
| 1.034 | CH$_2$CH$_2$CH$_3$ | CH$_3$ | CH$_3$ | C(O)OCH$_2$CH$_3$ | |
| 1.035 | CH$_2$CH$_2$CH$_3$ | CH$_3$ | CH$_2$CH$_3$ | H | |
| 1.036 | CH$_2$CH$_2$CH$_3$ | CH$_3$ | CH$_2$CH$_2$CH$_3$ | H | |
| 1.037 | CH$_2$CH$_2$CH$_3$ | CH$_3$ | CH$_2$CH$_2$CH$_3$ | C(O)C(CH$_3$)$_3$ | |
| 1.038 | CH$_2$CH$_2$CH$_3$ | CH$_3$ | CH$_2$CH$_2$CH$_3$ | C(O)OCH$_2$CH$_3$ | |
| 1.039 | CH$_2$CH$_2$CH$_3$ | CH$_3$ | C≡CH | H | |
| 1.040 | CH(CH$_3$)$_2$ | CH$_3$ | CH$_3$ | H | m.p. 214–216° C. |
| 1.041 | CH(CH$_3$)$_2$ | CH$_3$ | CH$_3$ | C(O)C(CH$_3$)$_3$ | m.p. 148–151° C. |
| 1.042 | CH(CH$_3$)$_2$ | CH$_3$ | CH$_2$CH$_3$ | H | |
| 1.043 | CH(CH$_3$)$_2$ | CH$_3$ | C≡CH | H | |

TABLE 1-continued

Compounds of the formula Ie:

(Ie)

| Comp. No. | R₁ | R₂ | R3 | G | Phys. data |
|---|---|---|---|---|---|
| 1.044 | cyclopropyl | CH₃ | CH₃ | H | |
| 1.045 | cyclopropyl | CH₃ | CH₂CH₃ | H | |
| 1.046 | cyclopropyl | CH₃ | C≡CH | H | |
| 1.047 | CH₂CH=CH₂ | CH₃ | CH₃ | H | |
| 1.048 | CH₂CH=CH₂ | CH₃ | CH₂CH₃ | H | |
| 1.049 | CH₂CH=CH₂ | CH₃ | C≡CH | H | |
| 1.050 | CH₂CH₂CH₂CH₃ | CH₃ | CH₃ | H | |
| 1.051 | CH₂CH₂CH₂CH₃ | CH₃ | CH₂CH₃ | H | |
| 1.052 | N(CH₂CH₃)₂ | CH₃ | CH₃ | H | |
| 1.053 | N(CH₂CH₃)₂ | CH₃ | CH₂CH₃ | H | |
| 1.054 | CH₂OH | CH₃ | CH₃ | H | |
| 1.055 | CH₂OCH₃ | CH₃ | CH₃ | H | |
| 1.056 | CH₂OC(CH₃)₃ | CH₃ | CH₃ | H | |
| 1.057 | CH₃ | CH₂CH₃ | CH₃ | H | |
| 1.058 | CH₂CH₃ | CH₂CH₃ | CH₃ | H | |
| 1.059 | CH₂CH₃ | CH₂CH₃ | CH₂CH₃ | H | m.p. 185–187° C. |
| 1.060 | CH₂CH₃ | CH₂CH₃ | CH₂CH₃ | C(O)C(CH₃)₃ | m.p. 126–128° C. |
| 1.061 | CH₂CH₃ | CH₂CH₃ | CH₂CH₃ | C(O)OCH₂CH₃ | m.p. 105–107° C. |
| 1.062 | CH=CH₂ | CH₂CH₃ | CH=CH₂ | H | |
| 1.063 | C≡CH | CH₂CH₃ | C≡CH | H | |
| 1.064 | CH₃ | CH=CH₂ | CH₃ | H | |
| 1.065 | CH₂CH₃ | CH=CH₂ | CH₂CH₃ | H | |
| 1.066 | CH₂CH₃ | CH=CH₂ | CH₃ | H | |
| 1.067 | CH₂CH₃ | CH=CH₂ | CH₃ | C(O)C(CH₃)₃ | m.p. 108–110° C. |
| 1.068 | C≡CH | CH=CH₂ | C≡CH | H | |
| 1.069 | CH₃ | C≡CH | CH₃ | H | |
| 1.070 | CH₂CH₃ | C≡CH | CH₃ | H | m.p. 240–243° C. |
| 1.071 | CH₂CH₃ | C≡CH | CH₃ | C(O)C(CH₃)₃ | m.p. 138–140° C. |
| 1.072 | CH₂CH₃ | C≡CH | CH₃ | C(O)OCH₂CH₃ | |
| 1.073 | CH₂CH₃ | C≡CH | CH₂CH₃ | H | |
| 1.074 | CH₂CH₃ | C≡CH | C≡CH | H | |
| 1.075 | C≡CH | C≡CH | C≡CH | H | |
| 1.076 | CH₃ | CH₂CH=CH₂ | CH₃ | H | |
| 1.077 | CH₃ | CH₂CH=CH₂ | CH₂CH₃ | H | |
| 1.078 | CH₃ | CH₃ | Br | H | m.p. 234–237° C. |

TABLE 1-continued

Compounds of the formula Ie:

(Ie)

| Comp. No. | $R_1$ | $R_2$ | R3 | G | Phys. data |
|---|---|---|---|---|---|
| 1.079 | $CH_3$ | $CH_3$ | Br | $C(O)C(CH_3)_3$ | m.p. 76–78° C. |
| 1.080 | $CH_3$ | $CH_3$ | Br | $C(O)OCH_2CH_3$ | |
| 1.081 | $CH_2CH_3$ | $CH_3$ | Br | H | |
| 1.082 | $C\equiv CH$ | $CH_3$ | Br | H | |
| 1.083 | $CH_3$ | Br | $CH_3$ | H | m.p. 298–299° C. |
| 1.084 | $CH_2CH_3$ | Br | $CH_3$ | H | mp. 261–263° C. |
| 1.085 | $CH_2CH_3$ | Br | $CH_3$ | $C(O)C(CH_3)_3$ | m.p. 127–130° C. |
| 1.086 | $CH_2CH_3$ | Br | $CH_3$ | $C(O)OCH_2CH_3$ | |
| 1.087 | $CH_2CH_3$ | Br | $CH_2CH_3$ | H | |
| 1.088 | Br | $CH_3$ | Br | H | m.p. 238–241° C. |
| 1.089 | Br | $CH_3$ | Br | $C(O)C(CH_3)_3$ | soiid |
| 1.090 | Br | $CH_3$ | Br | $C(O)OCH_2CH_3$ | |
| 1.091 | $CH_3$ | Br | Br | H | |
| 1.092 | $CH_2CH_3$ | Br | Br | H | |
| 1.093 | $CH_3$ | $CH_3$ | Cl | H | |
| 1.094 | $CH_2CH_3$ | $CH_3$ | Cl | H | |
| 1.095 | $CH_3$ | Cl | $CH_3$ | H | |
| 1.096 | $CH_2CH_3$ | Cl | $CH_3$ | H | |
| 1.097 | $CH_2CH_3$ | Cl | $CH_2CH_3$ | H | |
| 1.098 | $CH_2CH_3$ | F | $CH_2CH_3$ | H | |
| 1.099 | $CH_2CH_3$ | F | $C\equiv CH$ | H | |
| 1.100 | $CH_2CH_3$ | F | $OCH_3$ | H | |
| 1.101 | Cl | $CH_3$ | Cl | H | |
| 1.102 | $CH_3$ | Cl | Cl | H | |
| 1.103 | $CH_2CH_3$ | Cl | Cl | H | |
| 1.104 | Br | $CH_3$ | Cl | H | |
| 1.105 | $CH_3$ | Br | Cl | H | |
| 1.106 | $CH_3$ | Cl | Br | H | |
| 1.107 | $CH_2CH_3$ | Br | Cl | H | |
| 1.108 | $CH_2CH_3$ | Cl | Br | H | |
| 1.109 | $OCH_3$ | $CH_3$ | $CH_3$ | H | |
| 1.110 | $OCH_3$ | $CH_3$ | $CH_2CH_3$ | H | m.p. 178–179° C. |
| 1.111 | $OCH_3$ | $CH_3$ | $CH_2CH_3$ | $C(O)C(CH_3)_3$ | m.p. 146–147° C. |
| 1.112 | $OCH_3$ | $CH_3$ | $CH_2CH_3$ | $C(O)OCH_2CH_3$ | |
| 1.113 | $OCH_3$ | $CH_3$ | $CH_2CH_2CH_3$ | H | |
| 1.114 | $OCH_3$ | $CH_3$ | $C\equiv CH$ | H | |
| 1.115 | $OCH_3$ | $CH_3$ | Br | H | |
| 1.116 | $OCH_3$ | $CH_3$ | $OCH_3$ | H | |
| 1.117 | $C(O)CH_3$ | $CH_3$ | $CH_3$ | H | solid |
| 1.118 | $C(O)CH_3$ | $CH_3$ | $CH_2CH_3$ | H | |
| 1.119 | $CH_3$ | $C(O)CH_3$ | $CH_2CH_3$ | $C(O)C(CH_3)_3$ | m.p. 163–165° C. |
| 1.120 | $CH_3$ | $CH_2OH$ | $CH_2CH_3$ | H | |
| 1.121 | $CH_3$ | $CH_3$ | $CH_3$ | $SO_2CH_2CHCH_2$ | |
| 1.122 | $CH_3$ | $CH_3$ | $CH_3$ | $SO_2CH_2CHCHCl$ | |
| 1.123 | $CH_3$ | $CH_3$ | $CH_3$ | $SO_2CH_2CHCHCH_3$ | |
| 1.124 | $CH_2CH_3$ | $CH_3$ | $CH_2CH_3$ | $SO_2CH_2CHCH_2$ | |
| 1.125 | $CH_2CH_3$ | $CH_3$ | $CH_2CH_3$ | $SO_2CH_2CHCHCl$ | |
| 1.126 | $CH_2CH_3$ | $CH_3$ | $CH_2CH_3$ | $SO_2CH_2CHCHCH_3$ | |

TABLE 2

Compounds of the formula If:

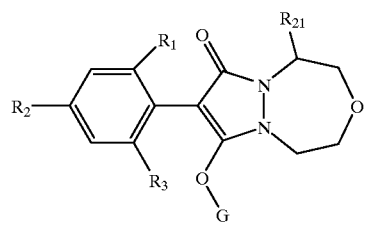

(If)

| Comp. No. | R₁ | R₂ | R₃ | G | R₂₁ | Phys. data |
|---|---|---|---|---|---|---|
| 2.001 | CH₃ | CH₃ | CH₃ | H | CH₃ | |
| 2.002 | CH₃ | CH₃ | CH₃ | C(O)C(CH₃)₃ | CH₃ | |
| 2.003 | CH₃ | CH₃ | CH₃ | C(O)OCH₂CH₃ | CH₃ | |
| 2.004 | CH₂CH₃ | CH₃ | CH₃ | H | CH₃ | |
| 2.005 | CH₂CH₃ | CH₃ | CH₂CH₃ | H | CH₃ | |
| 2.006 | CH₂CH₃ | CH₃ | CH₂CH₃ | C(O)C(CH₃)₃ | CH₃ | |
| 2.007 | CH₂CH₃ | CH₃ | CH₂CH₃ | C(O)OCH₂CH₃ | CH₃ | |
| 2.008 | CH₂CH₃ | CH₃ | Br | H | CH₃ | |
| 2.009 | CH₂CH₃ | CH₃ | Br | C(O)C(CH₃)₃ | CH₃ | |
| 2.010 | CH₂CH₃ | CH₃ | Br | C(O)OCH₂CH₃ | CH₃ | |
| 2.011 | CH₂CH₃ | CH₂CH₃ | CH₂CH₃ | H | CH₃ | |
| 2.012 | CH₂CH₃ | CH₂CH₃ | CH₂CH₃ | C(O)C(CH₃)₃ | CH₃ | |
| 2.013 | CH₂CH₃ | CH₂CH₃ | CH₂CH₃ | C(O)OCH₂CH₃ | CH₃ | |
| 2.014 | C≡CH | CH₃ | CH₃ | H | CH₃ | |
| 2.015 | C≡CH | CH₃ | CH₃ | C(O)C(CH₃)₃ | CH₃ | |
| 2.016 | C≡CH | CH₃ | CH₃ | C(O)OCH₂CH₃ | CH₃ | |
| 2.017 | C≡CH | CH₃ | CH₂CH₃ | H | CH₃ | |
| 2.018 | C≡CH | CH₃ | CH₂CH₃ | C(O)C(CH₃)₃ | CH₃ | |
| 2.019 | C≡CH | CH₃ | CH₂CH₃ | C(O)OCH₂CH₃ | CH₃ | |
| 2.020 | CH=CH₂ | CH₃ | CH=CH₂ | H | CH₃ | |
| 2.021 | C≡CH | CH₃ | C≡CH | H | CH₃ | |
| 2.022 | OCH₃ | CH₃ | CH₂CH₃ | H | CH₃ | |
| 2.023 | OCH₃ | CH₃ | CH₂CH₃ | C(O)C(CH₃)₃ | CH₃ | |
| 2.024 | OCH₃ | CH₃ | CH₂CH₃ | C(O)OCH₂CH₃ | CH₃ | |
| 2.025 | OCH₃ | CH₃ | Br | H | CH₃ | |
| 2.026 | OCH₃ | CH₃ | Br | C(O)C(CH₃)₃ | CH₃ | |
| 2.027 | OCH₃ | CH₃ | Br | C(O)OCH₂CH₃ | CH₃ | |
| 2.028 | OCH₃ | CH₃ | C≡CH | H | CH₃ | |
| 2.029 | OCH₃ | CH₃ | C≡CH | C(O)C(CH₃)₃ | CH₃ | |
| 2.030 | OCH₃ | CH₃ | C≡CH | C(O)OCH₂CH₃ | CH₃ | |
| 2.031 | CH₃ | C≡CH | CH₃ | H | CH₃ | |
| 2.032 | CH₂CH₃ | C≡CH | CH₃ | H | CH₃ | |

TABLE 3

Compounds of the formula Ig:

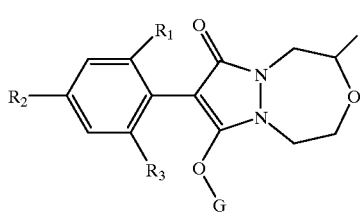

(Ig)

| Comp. No. | R₁ | R₂ | R₃ | G | R₁₉ | Phys. data |
|---|---|---|---|---|---|---|
| 3.001 | CH₃ | CH₃ | CH₃ | H | CH₃ | |
| 3.002 | CH₃ | CH₃ | CH₃ | C(O)C(CH₃)₃ | CH₃ | |
| 3.003 | CH₃ | CH₃ | CH₃ | C(O)OCH₂CH₃ | CH₃ | |
| 3.004 | CH₂CH₃ | CH₃ | CH₃ | H | CH₃ | |
| 3.005 | CH₂CH₃ | CH₃ | CH₂CH₃ | H | CH₃ | |
| 3.006 | CH₂CH₃ | CH₃ | CH₂CH₃ | C(O)C(CH₃)₃ | CH₃ | |
| 3.007 | CH₂CH₃ | CH₃ | CH₂CH₃ | C(O)OCH₂CH₃ | CH₃ | |

TABLE 3-continued

Compounds of the formula Ig:

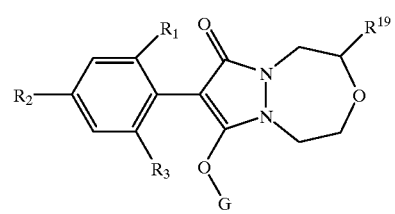

(Ig)

| Comp. No. | R₁ | R₂ | R₃ | G | R₁₉ | Phys. data |
|---|---|---|---|---|---|---|
| 3.008 | CH₂CH₃ | CH₃ | Br | H | CH₃ | |
| 3.009 | CH₂CH₃ | CH₃ | Br | C(O)C(CH₃)₃ | CH₃ | |
| 3.010 | CH₂CH₃ | CH₃ | Br | C(O)OCH₂CH₃ | CH₃ | |
| 3.011 | CH₂CH₃ | CH₂CH₃ | CH₂CH₃ | H | CH₃ | |
| 3.012 | CH₂CH₃ | CH₂CH₃ | CH₂CH₃ | C(O)C(CH₃)₃ | CH₃ | |
| 3.013 | CH₂CH₃ | CH₂CH₃ | CH₂CH₃ | C(O)OCH₂CH₃ | CH₃ | |
| 3.014 | C≡CH | CH₃ | CH₃ | H | CH₃ | |
| 3.015 | C≡CH | CH₃ | CH₃ | C(O)C(CH₃)₃ | CH₃ | |
| 3.016 | C≡CH | CH₃ | CH₃ | C(O)OCH₂CH₃ | CH₃ | |
| 3.017 | C≡CH | CH₃ | CH₂CH₃ | H | CH₃ | |
| 3.018 | C≡CH | CH₃ | CH₂CH₃ | C(O)C(CH₃)₃ | CH₃ | |
| 3.019 | C≡CH | CH₃ | CH₂CH₃ | C(O)OCH₂CH₃ | CH₃ | |
| 3.020 | CH=CH₂ | CH₃ | CH=CH₂ | H | CH₃ | |
| 3.021 | C≡CH | CH₃ | C≡CH | H | CH₃ | |
| 3.022 | OCH₃ | CH₃ | CH₂CH₃ | H | CH₃ | |
| 3.023 | OCH₃ | CH₃ | CH₂CH₃ | C(O)C(CH₃)₃ | CH₃ | |
| 3.024 | OCH₃ | CH₃ | CH₂CH₃ | C(O)OCH₂CH₃ | CH₃ | |
| 3.025 | OCH₃ | CH₃ | Br | H | CH₃ | |
| 3.026 | OCH₃ | CH₃ | Br | C(O)C(CH₃)₃ | CH₃ | |
| 3.027 | OCH₃ | CH₃ | Br | C(O)OCH₂CH₃ | CH₃ | |
| 3.028 | OCH₃ | CH₃ | C≡CH | H | CH₃ | |
| 3.029 | OCH₃ | CH₃ | C≡CH | C(O)C(CH₃)₃ | CH₃ | |
| 3.030 | OCH₃ | CH₃ | C≡CH | C(O)OCH₂CH₃ | CH₃ | |
| 3.031 | CH₃ | C≡CH | CH₃ | H | CH₃ | |
| 3.032 | CH₂CH₃ | C≡CH | CH₃ | H | CH₃ | |
| 3.033 | CH₂CH₃ | CH₃ | CH₂CH₃ | H | F | |
| 3.034 | CH₂CH₃ | CH₃ | CH₂CH₃ | H | Br | |
| 3.035 | CH₃ | CH₃ | CH₃ | H | Cl | |
| 3.036 | CH₃ | CH₃ | CH₃ | C(O)C(CH₃)₃ | Cl | |
| 3.037 | CH₃ | CH₃ | CH₃ | C(O)OCH₂CH₃ | Cl | |
| 3.038 | CH₂CH₃ | CH₃ | CH₂CH₃ | H | Cl | |
| 3.039 | CH₂CH₃ | CH₃ | CH₂CH₃ | C(O)C(CH₃)₃ | Cl | |
| 3.040 | CH₂CH₃ | CH₃ | CH₂CH₃ | C(O)OCH₂CH₃ | Cl | |
| 3.041 | CH₂CH₃ | CH₂CH₃ | CH₂CH₃ | H | Cl | |
| 3.042 | C≡CH | CH₃ | CH₃ | H | Cl | |
| 3.043 | C≡CH | CH₃ | C≡CH | H | Cl | |
| 3.044 | CH₃ | C≡CH | CH₃ | H | Cl | |

TABLE 4

Compounds of the formula Ih:

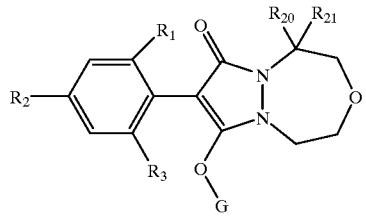

(Ih)

| Comp. No. | R$_1$ | R$_2$ | R$_3$ | G | R$_{20}$ | R$_{21}$ | Phys. data |
|---|---|---|---|---|---|---|---|
| 4.001 | CH$_3$ | CH$_3$ | CH$_3$ | H | CH$_3$ | CH$_3$ | |
| 4.002 | CH$_3$ | CH$_3$ | CH$_3$ | C(O)C(CH$_3$)$_3$ | CH$_3$ | CH$_3$ | |
| 4.003 | CH$_3$ | CH$_3$ | CH$_3$ | C(O)OCH$_2$CH$_3$ | CH$_3$ | CH$_3$ | |
| 4.004 | CH$_2$CH$_3$ | CH$_3$ | CH$_2$CH$_3$ | H | CH$_3$ | CH$_3$ | |
| 4.005 | CH$_2$CH$_3$ | CH$_3$ | CH$_2$CH$_3$ | C(O)C(CH$_3$)$_3$ | CH$_3$ | CH$_3$ | |
| 4.006 | CH$_2$CH$_3$ | CH$_3$ | CH$_2$CH$_3$ | C(O)OCH$_2$CH$_3$ | CH$_3$ | CH$_3$ | |
| 4.007 | CH$_2$CH$_3$ | CH$_2$CH$_3$ | CH$_2$CH$_3$ | H | CH$_3$ | CH$_3$ | |
| 4.008 | CH$_2$CH$_3$ | CH$_2$CH$_3$ | CH$_2$CH$_3$ | C(O)C(CH$_3$)$_3$ | CH$_3$ | CH$_3$ | |
| 4.009 | CH$_2$CH$_3$ | CH$_2$CH$_3$ | CH$_2$CH$_3$ | C(O)OCH$_2$CH$_3$ | CH$_3$ | CH$_3$ | |
| 4.010 | C≡CH | CH$_3$ | CH$_3$ | H | CH$_3$ | CH$_3$ | |
| 4.011 | C≡CH | CH$_3$ | CH$_3$ | C(O)C(CH$_3$)$_3$ | CH$_3$ | CH$_3$ | |
| 4.012 | C≡CH | CH$_3$ | CH$_3$ | C(O)OCH$_2$CH$_3$ | CH$_3$ | CH$_3$ | |
| 4.013 | C≡CH | CH$_3$ | C≡CH | H | CH$_3$ | CH$_3$ | |
| 4.014 | CH$_3$ | C≡CH | CH$_3$ | H | CH$_3$ | CH$_3$ | |
| 4.015 | CH$_3$ | CH$_3$ | CH$_3$ | H | CH$_2$CH$_2$ | | |
| 4.016 | CH$_2$CH$_3$ | CH$_3$ | CH$_2$CH$_3$ | H | CH$_2$CH$_2$ | | |
| 4.017 | CH$_2$CH$_3$ | CH$_2$CH$_3$ | CH$_2$CH$_3$ | H | CH$_2$CH$_2$ | | |
| 4.018 | CH$_2$CH$_3$ | CH$_3$ | CH$_2$CH$_3$ | H | CH$_2$CH$_2$CH$_2$ | | |
| 4.019 | CH$_3$ | CH$_3$ | CH$_3$ | H | CH$_2$CH$_2$CH$_2$CH$_2$ | | |
| 4.020 | CH$_2$CH$_3$ | CH$_3$ | CH$_2$CH$_3$ | H | CH$_2$CH$_2$CH$_2$CH$_2$ | | |
| 4.021 | CH$_2$CH$_3$ | CH$_2$CH$_3$ | CH$_2$CH$_3$ | H | CH$_2$CH$_2$CH$_2$CH$_2$ | | |
| 4.022 | C≡CH | CH$_3$ | CH$_3$ | H | CH$_2$CH$_2$CH$_2$CH$_2$ | | |
| 4.023 | C≡CH | CH$_3$ | C≡CH | H | CH$_2$CH$_2$CH$_2$CH$_2$ | | |
| 4.024 | CH$_3$ | C≡CH | CH$_3$ | H | CH$_2$CH$_2$CH$_2$CH$_2$ | | |
| 4.025 | CH$_3$ | CH$_3$ | CH$_3$ | H | CH$_2$CH$_2$CH$_2$CH$_2$CH$_2$ | | |
| 4.026 | CH$_2$CH$_3$ | CH$_3$ | CH$_2$CH$_3$ | H | CH$_2$CH$_2$CH$_2$CH$_2$CH$_2$ | | |
| 4.027 | CH$_2$CH$_3$ | CH$_2$CH$_3$ | CH$_2$CH$_3$ | H | CH$_2$CH$_2$CH$_2$CH$_2$CH$_2$ | | |
| 4.028 | C≡CH | CH$_3$ | CH$_3$ | H | CH$_2$CH$_2$CH$_2$CH$_2$CH$_2$ | | |
| 4.029 | C≡CH | CH$_3$ | C≡CH | H | CH$_2$CH$_2$CH$_2$CH$_2$CH$_2$ | | |
| 4.030 | CH$_3$ | C≡CH | CH$_3$ | H | CH$_2$CH$_2$CH$_2$CH$_2$CH$_2$ | | |
| 4.031 | CH$_2$CH$_3$ | CH$_3$ | CH$_2$CH$_3$ | H | CH$_2$CH$_2$OCH$_2$CH$_2$ | | |

TABLE 5

Compounds of the formula Ik:

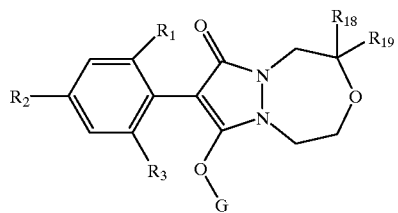

(Ik)

| Comp. No. | R$_1$ | R$_2$ | R$_3$ | G | R$_{18}$ | R$_{19}$ | Phys. data |
|---|---|---|---|---|---|---|---|
| 5.001 | CH$_3$ | CH$_3$ | CH$_3$ | H | CH$_3$ | CH$_3$ | |
| 5.002 | CH$_3$ | CH$_3$ | CH$_3$ | C(O)C(CH$_3$)$_3$ | CH$_3$ | CH$_3$ | |
| 5.003 | CH$_3$ | CH$_3$ | CH$_3$ | C(O)OCH$_2$CH$_3$ | CH$_3$ | CH$_3$ | |
| 5.004 | CH$_2$CH$_3$ | CH$_3$ | CH$_2$CH$_3$ | H | CH$_3$ | CH$_3$ | |
| 5.005 | CH$_2$CH$_3$ | CH$_3$ | CH$_2$CH$_3$ | C(O)C(CH$_3$)$_3$ | CH$_3$ | CH$_3$ | |
| 5.006 | CH$_2$CH$_3$ | CH$_3$ | CH$_2$CH$_3$ | C(O)OCH$_2$CH$_3$ | CH$_3$ | CH$_3$ | |
| 5.007 | CH$_2$CH$_3$ | CH$_2$CH$_3$ | CH$_2$CH$_3$ | H | CH$_3$ | CH$_3$ | |
| 5.008 | CH$_2$CH$_3$ | CH$_2$CH$_3$ | CH$_2$CH$_3$ | C(O)C(CH$_3$)$_3$ | CH$_3$ | CH$_3$ | |
| 5.009 | CH$_2$CH$_3$ | CH$_2$CH$_3$ | CH$_2$CH$_3$ | C(O)OCH$_2$CH$_3$ | CH$_3$ | CH$_3$ | |
| 5.010 | C≡CH | CH$_3$ | CH$_3$ | H | CH$_3$ | CH$_3$ | |
| 5.011 | C≡CH | CH$_3$ | CH$_3$ | C(O)C(CH$_3$)$_3$ | CH$_3$ | CH$_3$ | |
| 5.012 | C≡CH | CH$_3$ | CH$_3$ | C(O)OCH$_2$CH$_3$ | CH$_3$ | CH$_3$ | |

TABLE 5-continued

Compounds of the formula Ik:

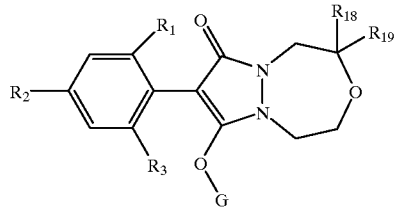

(Ik)

| Comp. No. | R₁ | R₂ | R₃ | G | R₁₈ | R₁₉ | Phys. data |
|---|---|---|---|---|---|---|---|
| 5.013 | C≡CH | CH₃ | C≡CH | H | CH₃ | CH₃ | |
| 5.014 | C≡CH | CH₃ | C≡CH | C(O)C(CH₃)₃ | CH₃ | CH₃ | |
| 5.015 | C≡CH | CH₃ | C≡CH | C(O)OCH₂CH₃ | CH₃ | CH₃ | |
| 5.016 | CH₃ | C≡CH | CH₃ | H | CH₃ | CH₃ | |
| 5.017 | CH₃ | CH₃ | CH₃ | H | CH₂CH₂ | | |
| 5.018 | CH₂CH₃ | CH₃ | CH₂CH₃ | H | CH₂CH₂ | | |
| 5.019 | CH₂CH₃ | CH₂CH₃ | CH₂CH₃ | H | CH₂CH₂ | | |
| 5.020 | CH₂CH₃ | CH₃ | CH₂CH₃ | H | CH₂CH₂CH₂ | | |
| 5.021 | CH₃ | CH₃ | CH₃ | H | CH₂CH₂CH₂CH₂ | | |
| 5.022 | CH₂CH₃ | CH₃ | CH₂CH₃ | H | CH₂CH₂CH₂CH₂ | | |
| 5.023 | CH₂CH₃ | CH₂CH₃ | CH₂CH₃ | H | CH₂CH₂CH₂CH₂ | | |
| 5.024 | C≡CH | CH₃ | CH₃ | H | CH₂CH₂CH₂CH₂ | | |
| 5.025 | C≡CH | CH₃ | C≡CH | H | CH₂CH₂CH₂CH₂ | | |
| 5.026 | CH₃ | C≡CH | CH₃ | H | CH₂CH₂CH₂CH₂ | | |
| 5.027 | CH₃ | CH₃ | CH₃ | H | CH₂CH₂CH₂CH₂CH₂ | | |
| 5.028 | CH₂CH₃ | CH₃ | CH₂CH₃ | H | CH₂CH₂CH₂CH₂CH₂ | | |
| 5.029 | CH₂CH₃ | CH₂CH₃ | CH₂CH₃ | H | CH₂CH₂CH₂CH₂CH₂ | | |
| 5.030 | C≡CH | CH₃ | CH₃ | H | CH₂CH₂CH₂CH₂CH₂ | | |
| 5.031 | C≡CH | CH₃ | C≡CH | H | CH₂CH₂CH₂CH₂CH₂ | | |
| 5.032 | CH₃ | C≡CH | CH₃ | H | CH₂CH₂CH₂CH₂CH₂ | | |
| 5.033 | CH₂CH₃ | CH₃ | CH₂CH₃ | H | CH₂CH₂OCH₂CH₂ | | |

TABLE 6

Compounds of the formula Im:

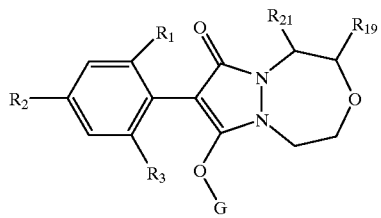

(Im)

| Comp. No. | R₁ | R₂ | R₃ | G | R₂₁ | R₁₉ | Phys. data |
|---|---|---|---|---|---|---|---|
| 6.001 | CH₃ | CH₃ | CH₃ | H | CH₃ | CH₃ | |
| 6.002 | CH₃ | CH₃ | CH₃ | C(O)C(CH₃)₃ | CH₃ | CH₃ | |
| 6.003 | CH₃ | CH₃ | CH₃ | C(O)OCH₂CH₃ | CH₃ | CH₃ | |
| 6.004 | CH₂CH₃ | CH₃ | CH₂CH₃ | H | CH₃ | CH₃ | |
| 6.005 | CH₂CH₃ | CH₃ | CH₂CH₃ | C(O)C(CH₃)₃ | CH₃ | CH₃ | |
| 6.006 | CH₂CH₃ | CH₃ | CH₂CH₃ | C(O)OCH₂CH₃ | CH₃ | CH₃ | |
| 6.007 | CH₂CH₃ | CH₂CH₃ | CH₂CH₃ | H | CH₃ | CH₃ | |
| 6.008 | CH₂CH₃ | CH₂CH₃ | CH₂CH₃ | C(O)C(CH₃)₃ | CH₃ | CH₃ | |
| 6.009 | CH₂CH₃ | CH₂CH₃ | CH₂CH₃ | C(O)OCH₂CH₃ | CH₃ | CH₃ | |
| 6.010 | C≡CH | CH₃ | CH₃ | H | CH₃ | CH₃ | |
| 6.011 | C≡CH | CH₃ | CH₃ | C(O)C(CH₃)₃ | CH₃ | CH₃ | |
| 6.012 | C≡CH | CH₃ | CH₃ | C(O)OCH₂CH₃ | CH₃ | CH₃ | |
| 6.013 | C≡CH | CH₃ | C≡CH | H | CH₃ | CH₃ | |
| 6.014 | C≡CH | CH₃ | C≡CH | C(O)C(CH₃)₃ | CH₃ | CH₃ | |
| 6.015 | C≡CH | CH₃ | C≡CH | C(O)OCH₂CH₃ | CH₃ | CH₃ | |
| 6.016 | CH₃ | C≡CH | CH₃ | H | CH₃ | CH₃ | |
| 6.017 | CH₂CH₃ | CH₃ | CH₂CH₃ | H | CH₂CH₂CH₂ | | |
| 6.018 | CH₂CH₃ | CH₃ | CH₂CH₃ | H | CH₂OCH₂ | | |
| 6.019 | CH₂CH₃ | CH₃ | CH₂CH₃ | H | CH₂CH₂CH₂CH₂ | | |

TABLE 7

Compounds of the formula In:

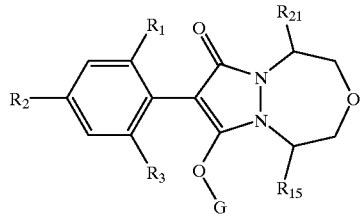

(In)

| Comp. No. | R₁ | R₂ | R₃ | G | R₂₁ | R₁₅ | Phys. data |
|---|---|---|---|---|---|---|---|
| 7.001 | $CH_3$ | $CH_3$ | $CH_3$ | H | $CH_3$ | $CH_3$ | |
| 7.002 | $CH_3$ | $CH_3$ | $CH_3$ | $C(O)C(CH_3)_3$ | $CH_3$ | $CH_3$ | |
| 7.003 | $CH_3$ | $CH_3$ | $CH_3$ | $C(O)OCH_2CH_3$ | $CH_3$ | $CH_3$ | |
| 7.004 | $CH_2CH_3$ | $CH_3$ | $CH_3$ | H | $CH_3$ | $CH_3$ | |
| 7.005 | $CH_2CH_3$ | $CH_3$ | $CH_3$ | $C(O)C(CH_3)_3$ | $CH_3$ | $CH_3$ | |
| 7.006 | $CH_2CH_3$ | $CH_3$ | $CH_3$ | $C(O)OCH_2CH_3$ | $CH_3$ | $CH_3$ | |
| 7.007 | $CH_2CH_3$ | $CH_3$ | $CH_2CH_3$ | H | $CH_3$ | $CH_3$ | solid |
| 7.008 | $CH_2CH_3$ | $CH_3$ | $CH_2CH_3$ | $C(O)C(CH_3)_3$ | $CH_3$ | $CH_3$ | solid |
| 7.009 | $CH_2CH_3$ | $CH_3$ | $CH_2CH_3$ | $C(O)OCH_2CH_3$ | $CH_3$ | $CH_3$ | |
| 7.010 | $CH_2CH_3$ | $CH_3$ | Br | H | $CH_3$ | $CH_3$ | |
| 7.011 | $CH_2CH_3$ | $CH_3$ | Br | $C(O)C(CH_3)_3$ | $CH_3$ | $CH_3$ | |
| 7.012 | $CH_2CH_3$ | $CH_3$ | Br | $C(O)OCH_2CH_3$ | $CH_3$ | $CH_3$ | |
| 7.013 | $CH_2CH_3$ | $CH_2CH_3$ | $CH_2CH_3$ | H | $CH_3$ | $CH_3$ | |
| 7.014 | $CH_2CH_3$ | $CH_2CH_3$ | $CH_2CH_3$ | $C(O)C(CH_3)_3$ | $CH_3$ | $CH_3$ | |
| 7.015 | $CH_2CH_3$ | $CH_2CH_3$ | $CH_2CH_3$ | $C(O)OCH_2CH_3$ | $CH_3$ | $CH_3$ | |
| 7.016 | C≡CH | $CH_3$ | $CH_3$ | H | $CH_3$ | $CH_3$ | |
| 7.017 | C≡CH | $CH_3$ | $CH_3$ | $C(O)C(CH_3)_3$ | $CH_3$ | $CH_3$ | |
| 7.018 | C≡CH | $CH_3$ | $CH_3$ | $C(O)OCH_2CH_3$ | $CH_3$ | $CH_3$ | |
| 7.019 | C≡CH | $CH_3$ | $CH_2CH_3$ | H | $CH_3$ | $CH_3$ | |
| 7.020 | C≡CH | $CH_3$ | $CH_2CH_3$ | $C(O)C(CH_3)_3$ | $CH_3$ | $CH_3$ | |
| 7.021 | C≡CH | $CH_3$ | $CH_2CH_3$ | $C(O)OCH_2CH_3$ | $CH_3$ | $CH_3$ | |
| 7.022 | $CH=CH_2$ | $CH_3$ | $CH=CH_2$ | H | $CH_3$ | $CH_3$ | |
| 7.023 | C≡CH | $CH_3$ | C≡CH | H | $CH_3$ | $CH_3$ | |
| 7.024 | C≡CH | $CH_3$ | C≡CH | $C(O)C(CH_3)_3$ | $CH_3$ | $CH_3$ | |
| 7.025 | C≡CH | $CH_3$ | C≡CH | $C(O)OCH_2CH_3$ | $CH_3$ | $CH_3$ | |
| 7.026 | $OCH_3$ | $CH_3$ | $CH_2CH_3$ | H | $CH_3$ | $CH_3$ | |
| 7.027 | $OCH_3$ | $CH_3$ | $CH_2CH_3$ | $C(O)C(CH_3)_3$ | $CH_3$ | $CH_3$ | |
| 7.028 | $OCH_3$ | $CH_3$ | $CH_2CH_3$ | $C(O)OCH_2CH_3$ | $CH_3$ | $CH_3$ | |
| 7.029 | $OCH_3$ | $CH_3$ | Br | H | $CH_3$ | $CH_3$ | |
| 7.030 | $OCH_3$ | $CH_3$ | Br | $C(O)C(CH_3)_3$ | $CH_3$ | $CH_3$ | |
| 7.031 | $OCH_3$ | $CH_3$ | Br | $C(O)OCH_2CH_3$ | $CH_3$ | $CH_3$ | |
| 7.032 | $OCH_3$ | $CH_3$ | C≡CH | H | $CH_3$ | $CH_3$ | |
| 7.033 | $OCH_3$ | $CH_3$ | C≡CH | $C(O)C(CH_3)_3$ | $CH_3$ | $CH_3$ | |
| 7.034 | $OCH_3$ | $CH_3$ | C≡CH | $C(O)OCH_2CH_3$ | $CH_3$ | $CH_3$ | |
| 7.035 | $CH_3$ | C≡CH | $CH_3$ | H | $CH_3$ | $CH_3$ | |
| 7.036 | $CH_2CH_3$ | C≡CH | $CH_3$ | H | $CH_3$ | $CH_3$ | |
| 7.037 | $CH_3$ | $CH_3$ | $CH_3$ | H | $CH_2$ | | |
| 7.038 | $CH_3$ | $CH_3$ | $CH_3$ | $C(O)C(CH_3)_3$ | $CH_2$ | | |
| 7.039 | $CH_3$ | $CH_3$ | $CH_3$ | $C(O)OCH_2CH_3$ | $CH_2$ | | |
| 7.040 | $CH_2CH_3$ | $CH_3$ | $CH_2CH_3$ | H | $CH_2$ | | |
| 7.041 | $CH_2CH_3$ | $CH_3$ | $CH_2CH_3$ | $C(O)C(CH_3)_3$ | $CH_2$ | | |
| 7.042 | $CH_2CH_3$ | $CH_3$ | $CH_2CH_3$ | $C(O)OCH_2CH_3$ | $CH_2$ | | |
| 7.043 | $CH_2CH_3$ | $CH_3$ | Br | H | $CH_2$ | | |
| 7.044 | $CH_2CH_3$ | $CH_3$ | Br | $C(O)C(CH_3)_3$ | $CH_2$ | | |
| 7.045 | $CH_2CH_3$ | $CH_3$ | Br | $C(O)OCH_2CH_3$ | $CH_2$ | | |
| 7.046 | C≡CH | $CH_3$ | $CH_3$ | H | $CH_2$ | | |
| 7.047 | C≡CH | $CH_3$ | $CH_3$ | $C(O)C(CH_3)_3$ | $CH_2$ | | |
| 7.048 | C≡CH | $CH_3$ | $CH_3$ | $C(O)OCH_2CH_3$ | $CH_2$ | | |
| 7.049 | C≡CH | $CH_3$ | $CH_2CH_3$ | H | $CH_2$ | | |
| 7.050 | C≡CH | $CH_3$ | $CH_2CH_3$ | $C(O)C(CH_3)_3$ | $CH_2$ | | |
| 7.051 | C≡CH | $CH_3$ | $CH_2CH_3$ | $C(O)OCH_2CH_3$ | $CH_2$ | | |
| 7.052 | C≡CH | $CH_3$ | C≡CH | H | $CH_2$ | | |
| 7.053 | C≡CH | $CH_3$ | C≡CH | $C(O)C(CH_3)_3$ | $CH_2$ | | |
| 7.054 | C≡CH | $CH_3$ | C≡CH | $C(O)OCH_2CH_3$ | $CH_2$ | | |
| 7.055 | $OCH_3$ | $CH_3$ | $CH_2CH_3$ | H | $CH_2$ | | |
| 7.056 | $OCH_3$ | $CH_3$ | $CH_2CH_3$ | $C(O)C(CH_3)_3$ | $CH_2$ | | |
| 7.057 | $OCH_3$ | $CH_3$ | $CH_2CH_3$ | $C(O)OCH_2CH_3$ | $CH_2$ | | |
| 7.058 | $OCH_3$ | $CH_3$ | Br | H | $CH_2$ | | |
| 7.059 | $OCH_3$ | $CH_3$ | Br | $C(O)C(CH_3)_3$ | $CH_2$ | | |
| 7.060 | $OCH_3$ | $CH_3$ | Br | $C(O)OCH_2CH_3$ | $CH_2$ | | |
| 7.061 | $OCH_3$ | $CH_3$ | C≡CH | H | $CH_2$ | | |
| 7.062 | $OCH_3$ | $CH_3$ | C≡CH | $C(O)C(CH_3)_3$ | $CH_2$ | | |
| 7.063 | $OCH_3$ | $CH_3$ | C≡CH | $C(O)OCH_2CH_3$ | $CH_2$ | | |

TABLE 7-continued

Compounds of the formula In:

(In)

| Comp. No. | $R_1$ | $R_2$ | $R_3$ | G | $R_{21}$ | $R_{15}$ | Phys. data |
|---|---|---|---|---|---|---|---|
| 7.064 | $CH_3$ | $CH_3$ | $CH_3$ | H | | $CH_2CH_2$ | |
| 7.065 | $CH_3$ | $CH_3$ | $CH_3$ | $C(O)C(CH_3)_3$ | | $CH_2CH_2$ | |
| 7.066 | $CH_3$ | $CH_3$ | $CH_3$ | $C(O)OCH_2CH_3$ | | $CH_2CH_2$ | |
| 7.067 | $CH_2CH_3$ | $CH_3$ | $CH_2CH_3$ | H | | $CH_2CH_2$ | |
| 7.068 | $CH_2CH_3$ | $CH_3$ | $CH_2CH_3$ | $C(O)C(CH_3)_3$ | | $CH_2CH_2$ | |
| 7.069 | $CH_2CH_3$ | $CH_3$ | $CH_2CH_3$ | $C(O)OCH_2CH_3$ | | $CH_2CH_2$ | |
| 7.070 | $CH_2CH_3$ | $CH_3$ | Br | H | | $CH_2CH_2$ | |
| 7.071 | $CH_2CH_3$ | $CH_3$ | Br | $C(O)C(CH_3)_3$ | | $CH_2CH_2$ | |
| 7.072 | $CH_2CH_3$ | $CH_3$ | Br | $C(O)OCH_2CH_3$ | | $CH_2CH_2$ | |
| 7.073 | C≡CH | $CH_3$ | $CH_3$ | H | | $CH_2CH_2$ | |
| 7.074 | C≡CH | $CH_3$ | $CH_3$ | $C(O)C(CH_3)_3$ | | $CH_2CH_2$ | |
| 7.075 | C≡CH | $CH_3$ | $CH_3$ | $C(O)OCH_2CH_3$ | | $CH_2CH_2$ | |
| 7.076 | C≡CH | $CH_3$ | $CH_2CH_3$ | H | | $CH_2CH_2$ | |
| 7.077 | C≡CH | $CH_3$ | $CH_2CH_3$ | $C(O)C(CH_3)_3$ | | $CH_2CH_2$ | |
| 7.078 | C≡CH | $CH_3$ | $CH_2CH_3$ | $C(O)OCH_2CH_3$ | | $CH_2CH_2$ | |
| 7.079 | C≡CH | $CH_3$ | C≡CH | H | | $CH_2CH_2$ | |
| 7.080 | C≡CH | $CH_3$ | C≡CH | $C(O)C(CH_3)_3$ | | $CH_2CH_2$ | |
| 7.081 | C≡CH | $CH_3$ | C≡CH | $C(O)OCH_2CH_3$ | | $CH_2CH_2$ | |
| 7.082 | $OCH_3$ | $CH_3$ | $CH_2CH_3$ | H | | $CH_2CH_2$ | |
| 7.083 | $OCH_3$ | $CH_3$ | $CH_2CH_3$ | $C(O)C(CH_3)_3$ | | $CH_2CH_2$ | |
| 7.084 | $OCH_3$ | $CH_3$ | $CH_2CH_3$ | $C(O)OCH_2CH_3$ | | $CH_2CH_2$ | |
| 7.085 | $OCH_3$ | $CH_3$ | Br | H | | $CH_2CH_2$ | |
| 7.086 | $OCH_3$ | $CH_3$ | Br | $C(O)C(CH_3)_3$ | | $CH_2CH_2$ | |
| 7.087 | $OCH_3$ | $CH_3$ | Br | $C(O)OCH_2CH_3$ | | $CH_2CH_2$ | |
| 7.088 | $OCH_3$ | $CH_3$ | C≡CH | H | | $CH_2CH_2$ | |
| 7.089 | $OCH_3$ | $CH_3$ | C≡CH | $C(O)C(CH_3)_3$ | | $CH_2CH_2$ | |
| 7.090 | $OCH_3$ | $CH_3$ | C≡CH | $C(O)OCH_2CH_3$ | | $CH_2CH_2$ | |

TABLE 8

Compounds of the formula Io:

(Io)

| Comp. No. | $R_1$ | $R_2$ | $R_3$ | G | $R_{19}$ | $R_{17}$ | Phys. data |
|---|---|---|---|---|---|---|---|
| 8.001 | $CH_3$ | $CH_3$ | $CH_3$ | H | $CH_3$ | $CH_3$ | |
| 8.002 | $CH_3$ | $CH_3$ | $CH_3$ | $C(O)C(CH_3)_3$ | $CH_3$ | $CH_3$ | |
| 8.003 | $CH_3$ | $CH_3$ | $CH_3$ | $C(O)OCH_2CH_3$ | $CH_3$ | $CH_3$ | |
| 8.004 | $CH_2CH_3$ | $CH_3$ | $CH_3$ | H | $CH_3$ | $CH_3$ | |
| 8.005 | $CH_2CH_3$ | $CH_3$ | $CH_3$ | $C(O)C(CH_3)_3$ | $CH_3$ | $CH_3$ | |
| 8.006 | $CH_2CH_3$ | $CH_3$ | $CH_3$ | $C(O)OCH_2CH_3$ | $CH_3$ | $CH_3$ | |
| 8.007 | $CH_2CH_3$ | $CH_3$ | $CH_2CH_3$ | H | $CH_3$ | $CH_3$ | |
| 8.008 | $CH_2CH_3$ | $CH_3$ | $CH_2CH_3$ | $C(O)C(CH_3)_3$ | $CH_3$ | $CH_3$ | |
| 8.009 | $CH_2CH_3$ | $CH_3$ | $CH_2CH_3$ | $C(O)OCH_2CH_3$ | $CH_3$ | $CH_3$ | |
| 8.010 | $CH_2CH_3$ | $CH_3$ | Br | H | $CH_3$ | $CH_3$ | |
| 8.011 | $CH_2CH_3$ | $CH_3$ | Br | $C(O)C(CH_3)_3$ | $CH_3$ | $CH_3$ | |
| 8.012 | $CH_2CH_3$ | $CH_3$ | Br | $C(O)OCH_2CH_3$ | $CH_3$ | $CH_3$ | |
| 8.013 | $CH_2CH_3$ | $CH_2CH_3$ | $CH_2CH_3$ | H | $CH_3$ | $CH_3$ | |
| 8.014 | $CH_2CH_3$ | $CH_2CH_3$ | $CH_2CH_3$ | $C(O)C(CH_3)_3$ | $CH_3$ | $CH_3$ | |
| 8.015 | $CH_2CH_3$ | $CH_2CH_3$ | $CH_2CH_3$ | $C(O)OCH_2CH_3$ | $CH_3$ | $CH_3$ | |
| 8.016 | C≡CH | $CH_3$ | $CH_3$ | H | $CH_3$ | $CH_3$ | |

TABLE 8-continued

Compounds of the formula Io:

(Io)

| Comp. No. | $R_1$ | $R_2$ | $R_3$ | G | $R_{19}$ | $R_{17}$ | Phys. data |
|---|---|---|---|---|---|---|---|
| 8.017 | C≡CH | CH3 | $CH_3$ | $C(O)C(CH_3)_3$ | $CH_3$ | $CH_3$ | |
| 8.018 | C≡CH | $CH_3$ | $CH_3$ | $C(O)OCH_2CH_3$ | $CH_3$ | $CH_3$ | |
| 8.019 | C≡CH | $CH_3$ | $CH_2CH_3$ | H | $CH_3$ | $CH_3$ | |
| 8.020 | C≡CH | $CH_3$ | $CH_2CH_3$ | $C(O)C(CH_3)_3$ | $CH_3$ | $CH_3$ | |
| 8.021 | C≡CH | $CH_3$ | $CH_2CH_3$ | $C(O)OCH_2CH_3$ | $CH_3$ | $CH_3$ | |
| 8.022 | CH=$CH_2$ | $CH_3$ | CH=$CH_2$ | H | $CH_3$ | $CH_3$ | |
| 8.023 | O=CH | $CH_3$ | C≡CH | H | $CH_3$ | $CH_3$ | |
| 8.024 | C≡CH | $CH_3$ | C≡CH | $C(O)C(CH_3)_3$ | $CH_3$ | $CH_3$ | |
| 8.025 | C≡CH | $CH_3$ | C≡CH | $C(O)OCH_2CH_3$ | $CH_3$ | $CH_3$ | |
| 8.026 | $OCH_3$ | $CH_3$ | $CH_2CH_3$ | H | $CH_3$ | $CH_3$ | |
| 8.027 | $CCH_3$ | $CH_3$ | $CH_2CH_3$ | $C(O)C(CH_3)_3$ | $CH_3$ | $CH_3$ | |
| 8.028 | $OCH_3$ | $CH_3$ | $CH_2CH_3$ | $C(O)OCH_2CH_3$ | $CH_3$ | $CH_3$ | |
| 8.029 | $OCH_3$ | $CH_3$ | Br | H | $CH_3$ | $CH_3$ | |
| 8.030 | $OCH_3$ | $CH_3$ | Br | $C(O)C(CH_3)_3$ | $CH_3$ | $CH_3$ | |
| 8.031 | $OCH_3$ | $CH_3$ | Br | $C(O)OCH_2CH_3$ | $CH_3$ | CH3 | |
| 8.032 | $OCH_3$ | $CH_3$ | C≡CH | H | $CH_3$ | $CH_3$ | |
| 8.033 | $OCH_3$ | $CH_3$ | C≡CH | $C(O)C(CH_3)_3$ | $CH_3$ | $CH_3$ | |
| 8.034 | $OCH_3$ | $CH_3$ | C≡CH | $C(O)OCH_2CH_3$ | $CH_3$ | $CH_3$ | |
| 8.035 | $CH_3$ | C≡CH | $CH_3$ | H | $CH_3$ | $CH_3$ | |
| 8.036 | $CH_2CH_3$ | C≡CH | $CH_3$ | H | $CH_3$ | $CH_3$ | |
| 8.037 | $CH_2CH_3$ | $CH_3$ | $CH_2CH_3$ | H | F | F | |
| 8.038 | $CH_3$ | $CH_3$ | $CH_3$ | H | Cl | Cl | |
| 8.039 | $CH_2CH_3$ | $CH_3$ | $CH_2CH_3$ | H | Cl | Cl | |
| 8.040 | $CH_3$ | $CH_3$ | $CH_3$ | H | $CH_2CH_2$ | | m.p. 295° C. |
| 8.041 | $CH_3$ | $CH_3$ | $CH_3$ | $C(O)C(CH_3)_3$ | $CH_2CH_2$ | | m.p. 198–199° C. |
| 8.042 | $CH_3$ | $CH_3$ | $CH_3$ | $C(O)OCH_2CH_3$ | $CH_2CH_2$ | | |
| 8.043 | $CH_2CH_3$ | $CH_3$ | $CH_2CH_3$ | H | $CH_2CH_2$ | | m.p. 287° C. |
| 8.044 | $CH_2CH_3$ | $CH_3$ | $CH_2CH_3$ | $C(O)C(CH_3)_3$ | $CH_2CH_2$ | | m.p. 141–143° C. |
| 8.045 | $CH_2CH_3$ | $CH_3$ | $CH_2CH_3$ | $C(O)OCH_2CH_3$ | $CH_2CH_2$ | | |
| 8.046 | $CH_2CH_3$ | $CH_3$ | Br | H | $CH_2CH_2$ | | |
| 8.047 | $CH_2CH_3$ | $CH_3$ | Br | $C(O)C(CH_3)_3$ | $CH_2CH_2$ | | |
| 8.048 | $CH_2CH_3$ | $CH_3$ | Br | $C(O)OCH_2CH_3$ | $CH_2CH_2$ | | |
| 8.049 | C≡CH | $CH_3$ | $CH_3$ | H | $CH_2CH_2$ | | |
| 8.050 | C≡CH | $CH_3$ | $CH_3$ | $C(O)C(CH_3)_3$ | $CH_2CH_2$ | | |
| 8.051 | C≡CH | $CH_3$ | $CH_3$ | $C(O)OCH_2CH_3$ | $CH_2CH_2$ | | |
| 8.052 | C≡CH | $CH_3$ | $CH_2CH_3$ | H | $CH_2CH_2$ | | |
| 8.053 | C≡CH | $CH_3$ | $CH_2CH_3$ | $C(O)C(CH_3)_3$ | $CH_2CH_2$ | | |
| 8.054 | C≡CH | $CH_3$ | $CH_2CH_3$ | $C(O)OCH_2CH_3$ | $CH_2CH_2$ | | |
| 8.055 | C≡CH | $CH_3$ | C≡CH | H | $CH_2CH_2$ | | |
| 8.056 | #CH | $CH_3$ | C≡CH | $C(O)C(CH_3)_3$ | $CH_2CH_2$ | | |
| 8.057 | C≡CH | $CH_3$ | C≡CH | $C(O)OCH_2CH_3$ | $CH_2CH_2$ | | |
| 8.058 | $OCH_3$ | $CH_3$ | $CH_2CH_3$ | H | $CH_2CH_2$ | | |
| 8.059 | $OCH_3$ | $CH_3$ | $CH_2CH_3$ | $C(O)C(CH_3)_3$ | $CH_2CH_2$ | | |
| 8.060 | $OCH_3$ | $CH_3$ | $CH_2CH_3$ | $C(O)OCH_2CH_3$ | $CH_2CH_2$ | | |
| 8.061 | $OCH_3$ | $CH_3$ | Br | H | $CH_2CH_2$ | | |
| 8.062 | $OCH_3$ | $CH_3$ | Br | $C(O)C(CH_3)_3$ | $CH_2CH_2$ | | |
| 8.063 | $OCH_3$ | $CH_3$ | Br | $C(O)OCH_2CH_3$ | $CH_2CH_2$ | | |
| 8.064 | $OCH_3$ | $CH_3$ | C≡CH | H | $CH_2CH_2$ | | |
| 8.065 | $OCH_3$ | $CH_3$ | C≡CH | $C(O)C(CH_3)_3$ | $CH_2CH_2$ | | |
| 8.066 | $OCH_3$ | $CH_3$ | C≡CH | $C(O)OCH_2CH_3$ | $CH_2CH_2$ | | |
| 8.067 | $CH_3$ | $CH_3$ | $CH_3$ | H | $CH_2CH_2CH_2$ | | |
| 8.068 | $CH_3$ | $CH_3$ | $CH_3$ | $C(O)C(CH_3)_3$ | $CH_2CH_2CH_2$ | | |
| 8.069 | $CH_3$ | $CH_3$ | $CH_3$ | $C(O)OCH_2CH_3$ | $CH_2CH_2CH_2$ | | |
| 8.070 | $CH_2CH_3$ | $CH_3$ | $CH_2CH_3$ | H | $CH_2CH_2CH_2$ | | |
| 8.071 | $CH_2CH_3$ | $CH_3$ | $CH_2CH_3$ | $C(O)C(CH_3)_3$ | $CH_2CH_2CH_2$ | | |
| 8.072 | $CH_2CH_3$ | $CH_3$ | $CH_2CH_3$ | $C(O)OCH_2CH_3$ | $CH_2CH_2CH_2$ | | |
| 8.073 | $CH_2CH_3$ | $CH_3$ | Br | H | $CH_2CH_2CH_2$ | | |
| 8.074 | $CH_2CH_3$ | $CH_3$ | Br | $C(O)C(CH_3)_3$ | $CH_2CH_2CH_2$ | | |
| 8.075 | $CH_2CH_3$ | $CH_3$ | Br | $C(O)OCH_2CH_3$ | $CH_2CH_2CH_2$ | | |
| 8.076 | C≡CH | $CH_3$ | $CH_3$ | H | $CH_2CH_2CH_2$ | | |

TABLE 8-continued

Compounds of the formula Io:

(Io)

| Comp. No. | $R_1$ | $R_2$ | $R_3$ | G | $R_{19}$ | $R_{17}$ | Phys. data |
|---|---|---|---|---|---|---|---|
| 8.077 | C≡CH | $CH_3$ | $CH_3$ | $C(O)C(CH_3)_3$ | | $CH_2CH_2CH_2$ | |
| 8.078 | C≡CH | $CH_3$ | $CH_3$ | $C(O)OCH_2CH_3$ | | $CH_2CH_2CH_2$ | |
| 8.079 | C≡CH | $CH_3$ | $CH_2CH_3$ | H | | $CH_2CH_2CH_2$ | |
| 8.080 | C≡CH | $CH_3$ | $CH_2CH_3$ | $C(O)C(CH_3)_3$ | | $CH_2CH_2CH_2$ | |
| 8.081 | C≡CH | $CH_3$ | $CH_2CH_3$ | $C(O)OCH_2CH_3$ | | $CH_2CH_2CH_2$ | |
| 8.082 | C≡CH | $CH_3$ | C≡CH | H | | $CH_2CH_2CH_2$ | |
| 8.083 | C≡CH | $CH_3$ | C≡CH | $C(O)C(CH_3)_3$ | | $CH_2CH_2CH_2$ | |
| 8.084 | C≡CH | $CH_3$ | C≡CH | $C(O)OCH_2CH_3$ | | $CH_2CH_2CH_2$ | |
| 8.085 | $OCH_3$ | $CH_3$ | $CH_2CH_3$ | H | | $CH_2CH_2CH_2$ | |
| 8.086 | $OCH_3$ | $CH_3$ | $CH_2CH_3$ | $C(O)C(CH_3)_3$ | | $CH_2CH_2CH_2$ | |
| 8.087 | $OCH_3$ | $CH_3$ | $CH_2CH_3$ | $C(O)OCH_2CH_3$ | | $CH_2CH_2CH_2$ | |
| 8.088 | $OCH_3$ | $CH_3$ | Br | H | | $CH_2CH_2CH_2$ | |
| 8.089 | $OCH_3$ | $CH_3$ | Br | $C(O)C(CH_3)_3$ | | $CH_2CH_2CH_2$ | |
| 8.090 | $OCH_3$ | $CH_3$ | Br | $C(O)OCH_2CH_3$ | | $CH_2CH_2CH_2$ | |
| 8.091 | $OCH_3$ | $CH_3$ | C≡CH | H | | $CH_2CH_2CH_2$ | |
| 8.092 | $OCH_3$ | $CH_3$ | C≡CH | $C(O)C(CH_3)_3$ | | $CH_2CH_2CH_2$ | |
| 8.093 | $OCH_3$ | $CH_3$ | C≡CH | $C(O)OCH_2CH_3$ | | $CH_2CH_2CH_2$ | |
| 8.094 | $CH_3$ | $CH_3$ | $CH_3$ | H | | $CH_2OCH_2$ | |
| 8.095 | $CH_3$ | $CH_3$ | $CH_3$ | $C(O)C(CH_3)_3$ | | $CH_2OCH_2$ | |
| 8.096 | $CH_3$ | $CH_3$ | $CH_3$ | $C(O)OCH_2CH_3$ | | $CH_2OCH_2$ | |
| 8.097 | $CH_2CH_3$ | $CH_3$ | $CH_2CH_3$ | H | | $CH_2OCH_2$ | |
| 8.098 | $CH_2CH_3$ | $CH_3$ | $CH_2CH_3$ | $C(O)C(CH_3)_3$ | | $CH_2OCH_2$ | |
| 8.099 | $CH_2CH_3$ | $CH_3$ | $CH_2CH_3$ | $C(O)OCH_2CH_3$ | | $CH_2OCH_2$ | |
| 8.100 | $CH_2CH_3$ | $CH_3$ | Br | H | | $CH_2OCH_2$ | |
| 8.101 | $CH_2CH_3$ | $CH_3$ | Br | $C(O)C(CH_3)_3$ | | $CH_2OCH_2$ | |
| 8.102 | $CH_2CH_3$ | $CH_3$ | Br | $C(O)OCH_2CH_3$ | | $CH_2OCH_2$ | |
| 8.103 | C≡CH | $CH_3$ | $CH_3$ | H | | $CH_2OCH_2$ | |
| 8.104 | C≡CH | $CH_3$ | $CH_3$ | $C(O)C(CH_3)_3$ | | $CH_2OCH_2$ | |
| 8.105 | C≡CH | $CH_3$ | $CH_3$ | $C(O)OCH_2CH_3$ | | $CH_2OCH_2$ | |
| 8.106 | C≡CH | $CH_3$ | $CH_2CH_3$ | H | | $CH_2OCH_2$ | |
| 8.107 | C≡CH | $CH_3$ | $CH_2CH_3$ | $C(O)C(CH_3)_3$ | | $CH_2OCH_2$ | |
| 8.108 | C≡CH | $CH_3$ | $CH_2CH_3$ | $C(O)OCH_2CH_3$ | | $CH_2OCH_2$ | |
| 8.109 | C≡CH | $CH_3$ | C≡CH | H | | $CH_2OCH_2$ | |
| 8.110 | C≡CH | $CH_3$ | C≡CH | $C(O)C(CH_3)_3$ | | $CH_2OCH_2$ | |
| 8.111 | C≡CH | $CH_3$ | C≡CH | $C(O)OCH_2CH_3$ | | $CH_2OCH_2$ | |
| 8.112 | $OCH_3$ | $CH_3$ | $CH_2CH_3$ | H | | $CH_2OCH_2$ | |
| 8.113 | $OCH_3$ | $CH_3$ | $CH_2CH_3$ | $C(O)C(CH_3)_3$ | | $CH_2OCH_2$ | |
| 8.114 | $OCH_3$ | $CH_3$ | $CH_2CH_3$ | $C(O)OCH_2CH_3$ | | $CH_2OCH_2$ | |
| 8.115 | $OCH_3$ | $CH_3$ | Br | H | | $CH_2OCH_2$ | |
| 8.116 | $OCH_3$ | $CH_3$ | Br | $C(O)C(CH_3)_3$ | | $CH_2OCH_2$ | |
| 8.117 | $OCH_3$ | $CH_3$ | Br | $C(O)OCH_2CH_3$ | | $CH_2OCH_2$ | |
| 8.118 | $OCH_3$ | $CH_3$ | C≡CH | H | | $CH_2OCH_2$ | |
| 8.119 | $OCH_3$ | $CH_3$ | C≡CH | $C(O)C(CH_3)_3$ | | $CH_2OCH_2$ | |
| 8.120 | $OCH_3$ | $CH_3$ | C≡CH | $C(O)OCH_2CH_3$ | | $CH_2OCH_2$ | |

Formulation examples for herbicidally active compounds of the formula I (%=per cent by weight)

| F1. Emulsion concentrates | a) | b) | c) | d) |
|---|---|---|---|---|
| Active compound according to Tables 1–8 | 5% | 10% | 25% | 50% |
| Ca dodecylbenzenesultonate | 6% | 8% | 6% | 8% |
| Castor oil polyglycol ether (36 mol of EO) | 4% | — | 4% | 4% |
| Octylphenol polyglycol ether (7–8 mol of EO) | — | 4% | — | 2% |
| Cyclohexanone | — | — | 10% | 20% |
| Arom. hydrocarbon mixture $C_9$–$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| Active compound according to Tables 1–8 | 5% | 10% | 50% | 90% |
| 1-Methoxy-3-(3-methoxy-propoxy)propane | — | 20% | 20% | — |
| Polyethylene glycol MW 400 | 20% | 10% | — | — |
| N-Methyl-2-pyrrolidone | — | — | 30% | 10% |
| Arom. hydrocarbon mixture $C_9$–$C_{12}$ | 75% | 60% | — | — |

The solutions are suitable for use in the form of tiny droplets.

| F3. Wettable powders | a) | b) | c) | d) |
|---|---|---|---|---|
| Active compound according to Tables 1–8 | 5% | 25% | 50% | 80% |
| Sodium lignosulfonate | 4% | — | 3% | — |
| Sodium laurylsulfate | 2% | 3% | — | 4% |
| Sodium diisobutylnaphthalene-sulfonate | — | 6% | 5% | 6% |
| Octylphenol polyglycol ethe (7–8 mol of EO) | — | 1% | 2% | — |
| Finely divided silica | 1% | 3% | 5% | 10% |
| Kaolin | 88% | 62% | 35% | — |

The active compound is thoroughly mixed with the additives and ground well in a suitable mill. This gives spray powders which can be diluted with water to give suspensions of any desired concentration.

| F4. Coated granules | a) | b) | c) |
|---|---|---|---|
| Active compound according to Tables 1–8 | 0.1% | 5% | 15% |
| Finely divided silica | 0.9% | 2% | 2% |
| Inorg. carrier material (Æ 0.1–1 mm), for example $CaCO_3$ or $SiO_2$ | 99.0% | 93% | 83% |

The active compound is dissolved in methylene chloride, the solution is sprayed onto the carrier and the solvent is subsequently evaporated off under reduced pressure.

| F5. Coated granules | a) | b) | c) |
|---|---|---|---|
| Active compound according to Tables 1–8 | 0.1% | 5% | 15% |
| Polyethylene glycol MW 200 | 1.0% | 2% | 3% |
| Finely divided silica | 0.9% | 1% | 2% |
| Inorg. carrier material (Æ 0.1–1 mm), for example $CaCO_3$ or $SiO_2$ | 98.0% | 92% | 80% |

In a mixer, the finely ground active compound is applied evenly to the carrier material moistened with polyethylene glycol. In this manner, dust-free coated granules are obtained.

| F6. Extruder granules | a) | b) | c) | d) |
|---|---|---|---|---|
| Active compound according to Tables 1–8 | 0.1% | 3% | 5% | 15% |
| Sodium lignosulfonate | 1.5% | 2% | 3% | 4% |
| Carboxymethylcellulose | 1.4% | 2% | 2% | 2% |
| Kaolin | 97.0% | 93% | 90% | 79% |

The active compound is mixed with the additives, ground and moistened with water. This mixture is extruded and subsequently dried in a stream of air.

| F7. Dusts | a) | b) | c) |
|---|---|---|---|
| Active compound according to Tables 1–8 | 0.1% | 1% | 5% |
| Talc mixture | 39.9% | 49% | 35% |
| Kaolin | 60.0% | 50% | 60% |

Ready-to-use dusts are obtained by mixing the active compound with the carriers and grinding the mixture in a suitable mill.

| F8. Suspension concentrates | a) | b) | c) | d) |
|---|---|---|---|---|
| Active compound according to Tables 1–8 | 3% | 10% | 25% | 50% |
| Ethylene glycol | 5% | 5% | 5% | 5% |
| Nonylphenol polyglycol ether (15 mol of EO) | — | 1% | 2% | — |
| Sodium lignosulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active compound is intimately mixed with the additives. This gives a suspension concentrate, from which suspensions of any desired concentration can be prepared by dilution with water.

BIOLOGICAL EXAMPLES

Experimental Comparison with the Prior Art

The following compounds were examined for their herbicidal activity:

Compound No. 1.01

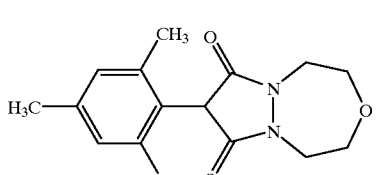

(1.01)

according to the present invention, and compound A

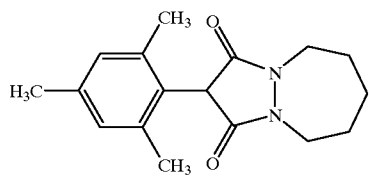

(compound A)

from the prior art (EP-A-0 508 126, compound no. 46 of Table 1).

Example B1

Herbicidal Action Before Emergence of the Plants (Pre-emergence Action)

Monocotyledonous and dicotyledonous weeds are sown in standard soil in plastic pots. Immediately after sowing, the test substances are applied (500 l of water/ha) as an aqueous suspension (prepared using a 25% wettable powder (Example F3, b)) or as an emulsion (prepared using a 25% emulsion concentrate (Example F1, c)). The application rate is 500 g of active substance/ha. The test plants are subsequently grown under optimum conditions in a greenhouse. 3 weeks after the application, evaluation is carried out using a nine-level scale of ratings (1=complete damage, 9=no effect). Ratings of 1 to 4 (in particular 1 to 3) mean a good to very good herbicidal action.

Test plants: Alopecurus (Alo), Avena (Ave), Lolium (Lot), Setaria (Set), Panicum (Pan), Sorghum (Sor), Digitaria (Dig), Echinocloa (Ech) and Brachiaria (Bra).

TABLE B1

| | Pre-emergence action: Pre-emergence action at 500 g of ai/ha | | | | | | | | |
|---|---|---|---|---|---|---|---|---|---|
| Comp. No. | Alo | Ave | Lol | Set | Pan | Sor | Dig | Ech | Bra |
| Compound A | 5 | 7 | 4 | 3 | 7 | 6 | 7 | 5 | 3 |
| 1.001 | 3 | 4 | 1 | 1 | 1 | 1 | 2 | 1 | 2 |

Example B2

Herbicidal Action After Emergence of the Plants (Post-emergence Action)

Monocotyledonous and dicotyledonous weeds are grown in standard soil in plastic pots under greenhouse conditions. The test substances are applied at the 3- to 6-leaf stage of the test plants. The test substances are applied (500 l of water/ha) as an aqueous suspension (prepared using a 25% wettable powder (Example F3, b)) or as an emulsion (prepared using a 25% emulsion concentrate (Example F1, c)) at an application rate of 500 g of active substance/ha. 3 weeks after the application, evaluation is carried out using a nine-level scale of ratings (1=complete damage, 9=no effect). Ratings of 1 to 4 (in particular 1 to 3) mean a good to very good herbicidal action.

Test plants: Alopecurus (Alo), Avena (Ave), Lolium (Lol), Setaria (Set), Panicum (Pan), Sorghum (Sor), Digitaria (Dig), Echinocloa (Ech) and Brachiaria (Bra).

TABLE B2

| | Post-emergence action: Post-emergence action at 500 g of ai/ha | | | | | | | | |
|---|---|---|---|---|---|---|---|---|---|
| Comp. No. | Alo | Ave | Lol | Set | Pan | Sor | Dig | Ech | Bra |
| Compound A | 5 | 2 | 5 | 4 | 2 | 3 | 5 | 1 | 2 |
| 1.001 | 2 | 1 | 1 | 1 | 1 | 1 | 1 | 1 | 1 |

Comparing the herbicidal action of the compound A of the prior art with the compound no. 1.01 of the present invention, it can be seen that the compound no. 1.01 surprisingly exhibits considerably better herbicidal action against all of the weeds tested, although this compound differs from the compound A only in that an alkylene group in the ring has been replaced by oxygen.

Example B3

Herbicidal Action of Compounds of the Present Invention Before Emergence of the Plants (Pre-emergence Action)

Monocotyledonous and dicotyledonous weeds are grown in standard soil in plastic pots. Directly after sowing, the test substances are applied (500 l of water/ha) as an aqueous suspension (prepared using a 25% wettable powder (Example F3, b)) or as an emulsion (prepared using a 25% emulsion concentrate (Example F1, c)). The application rate is 500 g of active substance/ha. The test plants are subsequently grown under optimum conditions in a greenhouse 3 weeks after the application, evaluation is carried out using a nine-level scale of ratings (1=complete damage, 9=no effect). Ratings of 1 to 4 (in particular 1 to 3) mean a good to very good herbicidal action.

Test plants: Avena (Ave), Lolium (Lol), Setaria (Set).

TABLE B3

| | Pre-emergence action: | | |
|---|---|---|---|
| | Test plant: | | |
| Comp. No. | Ave | Lol | Set |
| 1.001 | 4 | 1 | 1 |
| 1.008 | 1 | 1 | 1 |
| 1.004 | 1 | 1 | 2 |

The same results are obtained when the compounds of the formula I are formulated according to Examples F2 and F4 to F8.

Example B4

Herbicidal Action of Compounds of the Present Invention After Emergence of the Plants (Post-emergence Action)

Monocotyledonous and dicotyledonous weeds are grown in standard soil in plastic pots under greenhouse conditions. The test substances are applied at the 3- to 6-leaf stage of the test plants. The test substances are applied (500 l of water/ha) as an aqueous suspension (prepared using a 25% wettable powder (Example F3, b)) or as an emulsion (prepared using a 25% emulsion concentrate (Example F1, c)) at an application rate of 250 g of active substance/ha. 3 weeks after the application, evaluation is carried out using a nine-level scale of ratings (1=complete damage, 9=no effect). Ratings of 1 to 4 (in particular 1 to 3) mean a good to very good herbicidal action.

Test plants: Avena (Ave), Lolium (Lol), Setaria (Set).

TABLE B4

Post-emergence action:

| Comp. No. | Test plant: | | |
|---|---|---|---|
| | Ave | Lol | Set |
| 1.001 | 1 | 1 | 2 |
| 1.088 | 4 | 4 | 3 |
| 1.078 | 1 | 1 | 4 |
| 1.007 | 1 | 1 | 1 |
| 1.005 | 1 | 2 | 2 |
| 1.085 | 1 | 2 | 2 |
| 1.016 | 3 | 2 | 2 |

The same results are obtained when the compounds of the formula I are formulated according to Examples F2 and F4 to F8.

What is claimed is:

1. A compound of the formula I

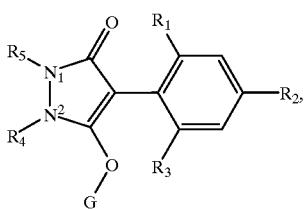

in which $R_1$, $R_2$ and $R_3$ independently of one another are halogen, nitro, cyano, $C_1$–$C_4$alkyl, $C_2$–$C_4$alkenyl, $C_2$–$C_4$alkynyl, $C_1$–$C_4$haloalkyl, $C_2$–$C_6$haloalkenyl, $C_3$–$C_6$cycloalkyl, halogen-substituted $C_3$–$C_6$cycloalkyl, $C_1$–$C_6$alkoxyalkyl, $C_1$–$C_6$alkylthioalkyl, hydroxyl, mercapto, $C_1$–$C_6$alkoxy, $C_3$–$C_6$alkenyloxy, $C_3$–$C_6$alkynyloxy, $C_1$–$C_4$alkylcarbonyl, $C_1$–$C_4$alkoxycarbonyl, $C_1$–$C_4$alkylthio, $C_1$–$C_4$alkylsulfinyl, $C_1$–$C_4$alkylsulfonyl, amino, $C_1$–$C_4$alkylamino or di($C_1$–$C_4$alkyl)amino;

$R_4$ and $R_5$ together are a group

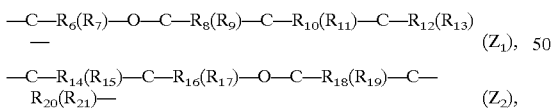

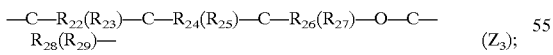

or

—C—$R_{22}$($R_{23}$)—C—$R_{24}$($R_{25}$)—C—$R_{26}$($R_{27}$)—O—C—
$R_{28}$($R_{29}$)—   ($Z_3$);

in which $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{29}$ independently of one another are hydrogen, halogen, $C_1$–$C_4$alkyl or $C_1$–$C_4$haloalkyl where an alkylene ring, which together with the carbon atoms of the groups $Z_1$, $Z_2$ or $Z_3$ contains 2 to 6 carbon atoms and may be interrupted by oxygen, may either be fused or spiro-linked to the carbon atoms of the groups $Z_1$, $Z_2$ or $Z_3$, or where this alkylene ring bridges at least one ring atom of the groups $Z_1$, $Z_2$ or $Z_3$;

G is hydrogen, —C($X_1$)—$R_{30}$, —C($X_2$)—$X_3$—$R_{31}$, —C($X_4$)—N($R_{32}$)—$R_{33}$, —SO$_2$—$R_{34}$, an alkali metal, alkaline earth metal, sulfonium or ammonium cation or —P($X_5$)($R_{35}$)—$R_{36}$;

$X_1$, $X_2$, $X_3$, $X_4$ and $X_5$ independently of one another are oxygen or sulfur; and $R_{30}$, $R_{31}$, $R_{32}$, $R_{33}$, $R_{34}$, $R_{35}$ and $R_{36}$ independently of one another are hydrogen, $C_1$–$C_5$alkyl, $C_1$–$C_5$haloalkyl, $C_2$–$C_5$alkenyl, $C_1$–$C_5$alkoxyalkyl, $C_3$–$C_6$cycloalkyl or phenyl, and $R_{34}$ is additionally $C_2$–$C_{20}$alkenyl, $C_2$–$C_{20}$alkenyl substituted by halogen, alkylcarbonyl, alkoxycarbonyl, alkylcarbonyloxy, alkoxy, thioalkyl, alkylthiocarbonyl, alkylcarbonylthio, alkylsulfonyl, alkylsulfoxyl, alkylaminosulfonyl, dialkylaminosulfonyl, alkylsulfonyloxy, alkylsulfonylamino, alkylamino, dialkylamino, alkylcarbonylamino, dialkylcarbonylamino, alkyl-alkylcarbonylamino, cyano, ($C_3$–$C_7$)cycloalkyl, ($C_3$–$C_7$)heterocyclyl, trialkylsilyl, trialkylsilyloxy, phenyl, substituted phenyl, heteroaryl or substituted heteroaryl, $C_2$–$C_{20}$alkynyl, $C_2$–$C_{20}$alkynyl substituted by halogen, alkylcarbonyl, alkoxycarbonyl, alkylcarbonyloxy, alkoxy, thioalkyl, alkylthiocarbonyl, alkylcarbonylthio, alkylsulfonyl, alkylsulfoxyl, alkylaminosulfonyl, dialkylaminosulfonyl, alkylsulfonyloxy, alkylsulfonylamino, alkylamino, dialkylamino, alkylcarbonylamino, dialkylcarbonylamino, alkyl-alkylcarbonylamino, cyano, ($C_3$–$C_7$)cycloalkyl, ($C_3$–$C_7$)heterocyclyl, trialkylsilyl, trialkylsilyloxy, phenyl, substituted phenyl, heteroaryl or substituted heteroaryl, ($C_1$–$C_7$)cycloalkyl, ($C_1$–$C_7$)cycloalkyl substituted by halogen, haloalkyl, ($C_1$–$C_6$)alkyl, alkoxy, alkylcarbonyloxy, thioalkyl, alkylcarbonylthio, alkylamino, alkylcarbonylamino, trialkylsilyl or trialkylsilyloxy, heteroaryl, heteroaryl substituted by halogen, haloalkyl, nitro, cyano, ($C_1$–$C_6$)alkyl, alkoxy, alkylcarbonyloxy, thioalkyl, alkylcarbonylthio, alkylamino, alkylcarbonylamino, trialkylsilyl or trialkylsilyloxy, heteroaryloxy, substituted heteroaryloxy, heteroarylthio, substituted heteroarylthio, heteroarylamino, substituted heteroarylamino, diheteroarylamino, substituted diheteroarylamino, phenylamino, substituted phenylamino, diphenylamino, substituted diphenylamino, cycloalkylamino, substituted cycloalkylamino, dicycloalkylamino, substituted dicycloalkylamino, cycloalkoxy or substituted cycloalkoxy, and salts and diastereomers of the compounds of the formula I.

2. A compound according to claim 1, wherein $R_4$ and $R_5$ together are a group

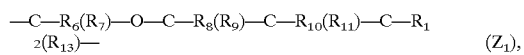

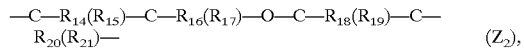

or

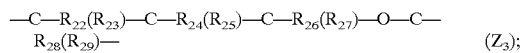

in which $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$ and $R_{29}$ independently of one another are hydrogen, halogen, $C_1$–$C_4$alkyl or $C_1$–$C_4$haloalkyl, where an alkylene ring which, together with the carbon atoms of the groups $Z_1$, $Z_2$ and $Z_3$, contains 3 to 6 carbon atoms may be fused or spiro-linked to the groups $Z_1$, $Z_2$ and $Z_3$.

3. A compound according to claim 1, wherein G is hydrogen.

4. A compound according to claim 1, wherein $R_4$ and $R_5$ together are a group $Z_2$.

5. A compound according to claim 1, wherein at least one ring atom of the groups $Z_1$, $Z_2$ or $Z_3$ is bridged by an alkylene ring which, together with the carbon atoms of the groups $Z_1$, $Z_2$ or $Z_3$, contains 2 to 6 carbon atoms and may be interrupted by oxygen.

6. A compound according to claim 1, wherein $R_1$, $R_2$ and $R_3$ independently of one another are halogen, $C_1$–$C_4$alkyl, $C_2$–$C_4$alkenyl, $C_2$–$C_4$alkynyl or $C_1$–$C_6$alkoxy.

7. A compound according to claim 1, wherein $R_2$ is halogen, methyl, ethyl or ethinyl.

8. A compound according to claim 1, wherein G is the group $—C(X_1)—R_{30}$ or $C(X_2)—(X_3)—R_{31}$ in which $X_1$, $X_2$ and $X_3$ are oxygen and $R_{30}$ and $R_{31}$ independently of one another are $C_1$–$C_5$alkyl.

9. A compound according to claim 1, wherein $R_1$ and $R_3$ independently of one another are methyl, ethyl, isopropyl, vinyl, allyl, ethinyl, methoxy, ethoxy, bromine or chlorine.

10. A compound according to claim 1, wherein $R_{30}$, $R_{31}$, $R_{32}$, $R_{33}$, $R_{34}$, $R_{35}$ and $R_{36}$ independently of one another are hydrogen, $C_1$–$C_5$alkyl or $C_1$–$C_5$haloalkyl.

11. A herbicidal and plant-growth-inhibiting composition, which contains a herbicidally effective amount of a compound of the formula I on an inert carrier.

12. A method for controlling undesirable plant growth, wherein a herbicidally effective amount of an active compound of the formula I or a composition which contains this active compound is applied to the plants or their habitat.

13. A method for inhibiting plant growth, wherein a herbididally effective amount of an active compound of the formula I or a composition which contains this active compound is applied to the plants or their habitat.

14. A selective-herbicidal composition which comprises as active compound, in addition to customary inert formulation auxiliaries, a mixture of
a) a herbicidally effective amount of a compound of the formula I according to claim 1 and
b) a herbicide-antagonistically effective amount of either a compound of the formula X (X)

in which
$R_{37}$ is hydrogen, $C_1$–$C_8$alkyl or $C_1$–$C_6$alkoxy- or $C_3$–$C_6$alkenyloxy-substituted $C_1$–$C_8$alkyl; and $X_6$ is hydrogen or chlorine; or a compound of the formula XI (XI)

in which
E is nitrogen or methine; $R_{38}$ is $—CCl_3$, phenyl or halogen-substituted phenyl;
$R_{39}$ and $R_{40}$ independently of one another are hydrogen or halogen; and
$R_{41}$ is $C_1$–$C_4$alkyl; or a compound of the formula XII (XII)

in which
$R_{44}$ and $R_{45}$ independently of one another are hydrogen or halogen and $R_{46}$, $R_{47}$ and $R_{48}$ independently of one another are $C_1$–$C_4$alkyl, or a compound of the formula XIII (XIII)

in which
$A_2$ is a group

-continued

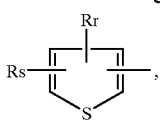

$R_{51}$ and $R_{52}$ independently of one another are hydrogen, $C_1$–$C_8$alkyl, $C_3$–$C_8$cycloalkyl, $C_3$–$C_6$alkenyl, $C_3$–$C_6$alkynyl,

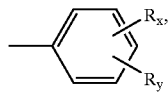

or $C_1$–$C_4$alkoxy- or

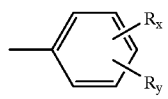

substituted $C_1$–$C_4$alkyl; or $R_{51}$ and $R_{52}$ together form a $C_4$–$C_6$alkylene bridge which may be interrupted by oxygen, sulfur, SO, $SO_2$, NH or —N($C_1$–$C_4$alkyl)—, $R_{53}$ is hydrogen or $C_1$–$C_4$alkyl;

$R_{49}$ is hydrogen, halogen, cyano, trifluoromethyl, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$, —$CONR_kR_m$, —$COR_n$; —$SO_2NR_kR_m$ or —$OSO_2$—$C_1$–$C_4$alkyl;

$R_g$ is hydrogen, halogen, cyano, nitro, $C_1$–$C_4$alkyl, $C_1$–$C_4$haloalkyl, $C_1$–$C_4$alkylthio, $C_1$–$C_4$alkylsulfinyl, $C_1$–$C_4$alkylsulfonyl, —$COOR_j$, $CONR_kR_m$, —$COR_n$, —$SO_2NR_kR_m$, —$OSO_2$—$C_1$–$C_4$alkyl, $C_1$–$C_6$alkoxy, or $C_1$–$C_6$alkoxy which is substituted by $C_1$–$C_4$alkoxy or halogen, $C_3$–$C_6$alkenyloxy, or $C_3$–$C_6$alkenyloxy which is substituted by halogen, or $C_3$–$C_6$alkynyloxy, or $R_{49}$ and $R_{50}$ together form a $C_3$–$C_4$alkylene bridge which may be substituted by halogen or $C_1$–$C_4$alkyl, or they form a $C_3$–$C_4$alkenylene bridge which may be substituted by halogen or $C_1$–$C_4$alkyl, or they form a $C_4$alkadienylene bridge which may be substituted by halogen or $C_1$–$C_4$alkyl;

$R_{50}$ and $R_h$ independently of one another are hydrogen, halogen, $C_1$–$C_4$alkyl, trifluoromethyl, $C_1$–$C_6$alkoxy, $C_1$–$C_6$alkylthio or —$COOR_j$;

$R_c$ is hydrogen, halogen, nitro, $C_1$–$C_4$alkyl or methoxy;

$R_d$ is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$ or $CONR_kR_m$;

$R_e$ is hydrogen, halogen, $C_1$–$C_4$alkyl, —$COOR_j$, trifluoromethyl or methoxy, or $R_d$ and $R_e$ together form a $C_3$–$C_4$alkylene bridge;

Rp is hydrogen, halogen, $C_1$–$C_4$alkyl, —$COOR_j$, trifluoromethyl or methoxy; Rq is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$ or $CONR_kR_m$, or Rp and Rq together form a $C_3$–$C_4$alkylene bridge;

Rr is hydrogen, halogen, $C_1$–$C_4$alkyl, —$COOR_j$, trifluoromethyl or methoxy; Rs is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$ or $CONR_kR_m$, or Rr and Rs together form a $C_3$–$C_4$alkylene bridge;

Rt is hydrogen, halogen, $C_1$–$C_4$alkyl, —$COOR_j$, trifluoromethyl or methoxy; Ru is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$ or $CONR_kR_m$, or Rv and Ru together form a $C_3$–$C_4$alkylene bridge;

$R_f$ and Rv are hydrogen, halogen or $C_1$–$C_4$alkyl;

$R_x$ and $R_y$ independently of one another are hydrogen, halogen, $C_1$–$C_4$alkyl, $C_1$–$C_4$alkoxy, $C_1$–$C_4$alkylthio, —$COOR_{54}$, trifluoromethyl, nitro or cyano;

$R_j$, $R_k$ and $R_m$ independently of one another are hydrogen or $C_1$–$C_4$alkyl; or $R_k$ and $R_m$ together form a $C_4$–$C_6$alkylene bridge which may be interrupted by oxygen, NH or —N($C_1$–$C_4$alkyl)—;

$R_n$ is $C_1$–$C_4$alkyl, phenyl, or halogen-, $C_1$–$C_4$alkyl-, methoxy-, nitro- or trifluoromethyl-substituted phenyl;

$R_{54}$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl which is unsubstituted or substituted up to three times on the phenyl ring by identical or different substituents selected from the group consisting of halogen, $C_1$–$C_4$alkyl, halo-$C_1$–$C_4$alkyl, halo-$C_1$–$C_4$alkoxy or $C_1$–$C_4$alkoxy; or furoyl, thienyl; or $C_1$–$C_4$alkyl which is substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl, di-$C_1$–$C_4$alkylaminocarbonyl; or phenylaminocarbonyl which is unsubstituted or substituted up to three times on the phenyl by identical or different substituents selected from the group consisting of halogen, $C_1$–$C_4$alkyl, halo-$C_1$–$C_4$alkyl, halo-$C_1$–$C_4$alkoxy and $C_1$–$C_4$alkoxy, or is monosubstituted by cyano or nitro, or dioxolan-2-yl which is unsubstituted or substituted by one or two $C_1$–$C_4$alkyl radicals, or dioxan-2-yl which is unsubstituted or substituted by one or two $C_1$–$C_4$alkyl radicals, or $C_1$–$C_4$alkyl which is substituted by cyano, nitro, carboxyl or $C_1$–$C_8$alkylthio-$C_1$–$C_8$alkoxycarbonyl;

or a compound of the formula XIV (XIV)

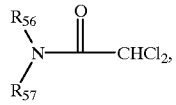

in which $R_{56}$ and $R_{57}$ independently of one another are $C_1$–$C_6$alkyl or $C_2$–$C_6$alkenyl; or $R_{56}$ and $R_{57}$ together are

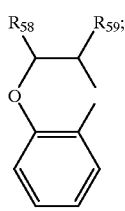

$R_{58}$ and $R_{59}$ independently of one another are hydrogen or $C_1$–$C_6$alkyl; or $R_{56}$ and $R_{57}$ together are

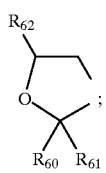

$R_{60}$ and $R_{61}$ independently of one another are $C_1$–$C_4$alkyl, or $R_{60}$ and $R_{61}$ together are —(CH$_2$)$_5$—;
$R_{62}$ is hydrogen, $C_1$–$C_4$alkyl or

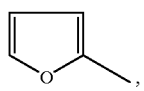

or $R_{56}$ and $R_{57}$ together are

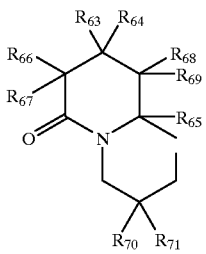 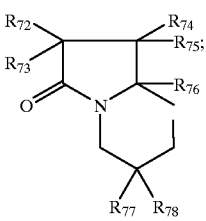

$R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$, $R_{76}$, $R_{77}$ and $R_{78}$ independently of one another are hydrogen or $C_1$–$C_4$alkyl;
or a compound of the formula XV (XV)

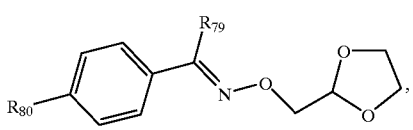

in which
$R_{80}$ is hydrogen or chlorine and $R_{79}$ is cyano or trifluoromethyl, or a compound of the formula XVI (XVI)

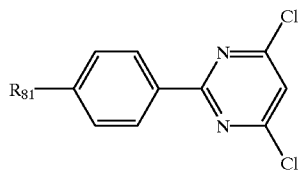

in which
$R_{81}$ is hydrogen or methyl,
or of the formula XVII (XVII)

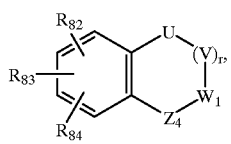

in which
$R_{82}$ is hydrogen, $C_1$–$C_4$alkyl, $C_1$–$C_4$alkyl which is substituted by $C_1$–$C_4$alkyl-$X_2$— or $C_1$–$C_4$haloalkyl-$X_2$—, $C_1$–$C_4$haloalkyl nitro, cyano, —COOR$_{85}$, —NR$_{86}$R$_{87}$, —SO$_2$NR$_{88}$R$_{89}$ or —CONR$_{90}$R$_{91}$;
$R_{83}$ is hydrogen, halogen, $C_1$–$C_4$alkyl, trifluoromethyl, $C_1$–$C_4$alkoxy or $C_1$–$C_4$haloalkoxy;
$R_{84}$ is hydrogen, halogen or $C_1$–$C_4$alkyl;
U, V, W$_1$ and Z$_4$ independently of one another are oxygen, sulfur, C(R$_{92}$)R$_{93}$, carbonyl, NR$_{94}$, a group

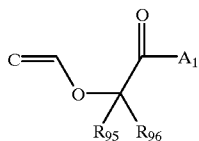 or 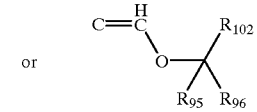

in which $R_{102}$ is $C_2$–$C_4$alkenyl or $C_2$–$C_4$alkynyl;
with the proviso that
a) at least one of the ring members U, V, W$_1$ or Z$_4$ is carbonyl, and a ring member which is adjacent to this or these ring members is the group

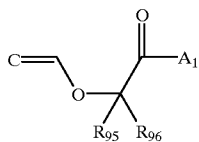 or 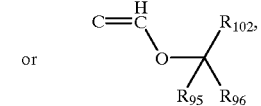

this group being present only once; and
b) two adjacent ring members U and V, V and W$_1$ and W$_1$ and Z$_4$ may not simultaneously be oxygen;
$R_{95}$ and $R_{96}$ independently of one another are hydrogen or $C_1$–$C_8$alkyl; or
$R_{95}$ and $R_{96}$ together form a $C_2$–$C_6$alkylene group;
$A_1$ is $R_{99}$—$Y_1$— or —NR$_{97}$R$_{98}$;
$X_2$ is oxygen or —S(O)$_s$;
$Y_1$ is oxygen or sulfur;
$R_{99}$ is hydrogen, $C_1$–$C_8$alkyl, $C_1$–$C_8$haloalkyl, $C_1$–$C_4$alkoxy-$C_1$–$C_8$alkyl, $C_3$–$C_6$alkenyloxy- $C_1$–$C_8$alkyl or phenyl-$C_1$–$C_8$alkyl, where the phenyl ring may be substituted by halogen, $C_1$–$C_4$alkyl, trifluoromethyl, methoxy or methyl-S(O)$_5$—, $C_3$–$C_6$alkenyl, $C_3$–$C_6$haloalkenyl, phenyl-$C_3$–$C_6$alkenyl, $C_3$–$C_6$alkynyl, phenyl-$C_3$–$C_6$alkynyl, oxetanyl, furyl or tetrahydrofuryl;

$R_{85}$ is hydrogen or $C_1$–$C_4$alkyl;

$R_{86}$ is hydrogen, $C_1$–$C_4$alkyl or $C_1$–$C_4$alkylcarbonyl;

$R_{87}$ is hydrogen or $C_1$–$C_4$alkyl; or $R_{86}$ and $R_{87}$ together form a $C_4$— or $C_5$alkylene group;

$R_{88}$, $R_{89}$, $R_{90}$ and $R_{91}$ independently of one another are hydrogen or $C_1$–$C_4$alkyl; or $R_{88}$ together with $R_{89}$ or $R_{90}$ together with $R_{91}$ independently of one another are $C_4$- or $C_5$-alkylene, where a carbon atom may be replaced by oxygen or sulfur, or one or two carbon atoms may be replaced by —$NR_{100}$—;

$R_{92}$, $R_{100}$ and $R_{93}$ independently of one another are hydrogen or $C_1$–$C_8$alkyl; or $R_{92}$ and $R_{93}$ together are $C_2$–$C_6$alkylene;

$R_{94}$ is hydrogen or $C_1$–$C_8$alkyl;

$R_{97}$ is hydrogen, $C_1$–$C_8$alkyl, phenyl, phenyl-$C_1$–$C_8$alkyl, where the phenyl rings may be substituted by fluorine, chlorine, bromine, nitro, cyano, —$OCH_3$, $C_1$–$C_4$alkyl or $CH_3SO_2$—, $C_1$–$C_4$alkoxy-$C_1$–$C_8$alkyl, $C_3$–$C_6$alkenyl or $C_3$–$C_6$alkynyl;

$R_{98}$ is hydrogen, $C_1$–$C_8$alkyl, $C_3$–$C_6$alkenyl or $C_3$–$C_6$alkynyl; or $R_{97}$ and $R_{98}$ together are $C_4$- or $C_5$-alkylene, where a carbon atom may be replaced by oxygen or sulfur, or one or two carbon atoms may be replaced by —$NR_{101}$—;

$R_{101}$ is hydrogen or $C_1$–$C_4$alkyl;

r is 0 or 1; and s is 0, 1 or 2, or a compound of the formula XVIII

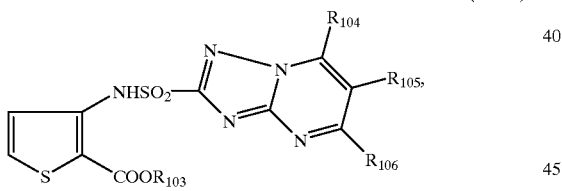

(XVIII)

in which $R_{103}$ is hydrogen, $C_1$–$C_6$alkyl, $C_3$–$C_6$cycloalkyl, $C_3$–$C_6$alkenyl or $C_3$–$C_6$alkynyl; and $R_{104}$, $R_{105}$ and $R_{106}$ independently of one another are hydrogen, $C_1$–$C_6$alkyl, $C_3$–$C_6$cycloalkyl or $C_1$–$C_6$alkoxy, with the proviso that one of the substituents $R_{104}$, $R_{105}$ and $R_{106}$ is different from hydrogen;

a compound of the formula XIX

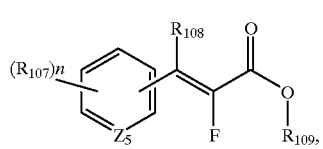

(XIX)

in which $Z_5$ is N or CH, n, in the case where $Z_5$ is N, is 0, 1, 2, or 3 and, in the case where $Z_5$ is CH, is 0, 1, 2, 3 or 4, $R_{107}$ is halogen, $C_1$–$C_4$alkyl, $C_1$–$C_4$haloalkyl, $C_1$–$C_4$alkoxy, $C_1$–$C_4$haloalkoxy, nitro, $C_1$–$C_4$alkylthio, $C_1$–$C_4$alkylsulfonyl, $C_1$–$C_4$alkoxycarbonyl or unsubstituted or substituted phenyl or phenoxy, $R_{108}$ is hydrogen or $C_1$–$C_4$alkyl, $R_{109}$ is hydrogen, $C_1$–$C_4$alkyl, $C_3$–$C_6$cycloalkyl, $C_2$–$C_6$alkenyl, $C_2$–$C_6$alkynyl, $C_1$–$C_4$haloalkyl, $C_2$–$C_6$haloalkenyl, $C_2$–$C_6$haloalkynyl, $C_1$–$C_4$alkylthio-$C_1$–$C_4$alkyl, $C_1$–$C_4$alkylsuffonyl-$C_1$–$C_4$alkyl, $C_1$–$C_4$alkoxy-$C_1$–$C_4$alkyl, $C_1$–$C_4$alkenyloxy-$C_1$–$C_4$alkyl or $C_1$–$C_4$alkynyloxy-$C_1$–$C_4$alkyl;

a compound of the formula XX

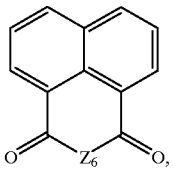

(XX)

in which $Z_6$ is O or N—$R_{110}$ and $R_{110}$ is a group of the formula

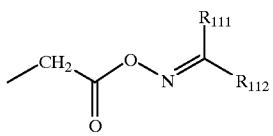

in which $R_{111}$ and $R_{112}$ independently of one another are cyano, hydrogen, $C_1$–$C_4$alkyl, $C_3$–$C_6$cycloalkyl, $C_2$–$C_6$alkenyl, unsubstituted or substituted phenyl or heteroaryl;

a compound of the formula XXI

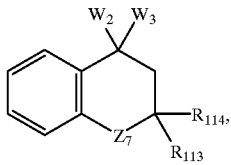

(XXI)

in which $Z_7$ is O, S, S=O, SO$_2$ or CH$_2$, $R_{113}$ and $R_{114}$ independently of one another are hydrogen, halogen or $C_1$–$C_4$alkyl, $W_2$ and $W_3$ independently of one another are $CH_2COOR_{115}$, $COOR_{115}$ or together are a group of the formula —(CH$_2$)C(O)—O—C(O)—(CH$_2$)—, and $R_{115}$ is hydrogen, $C_1$–$C_4$alkyl, $C_2$–$C_4$alkenyl, $C_2$–$C_6$alkynyl, $C_3$–$C_6$cycloalkyl, $C_1$–$C_4$haloalkyl, a metal cation or an ammonium cation;

a compound of the formula XXII

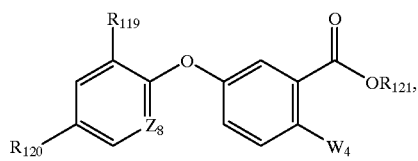

(XXII)

in which
R$_{119}$ and R$_{120}$ independently of one another are hydrogen, halogen or C$_1$–C$_4$haloalkyl, R$_{121}$ is hydrogen, C$_1$–C$_4$alkyl, C$_3$–C$_4$alkenyl, C$_3$–C$_4$alkynyl, C$_1$–C$_4$haloalkyl, C$_3$–C$_6$cycloalkyl, a metal cation or an ammonium cation, Z$_8$ is N, CH, C—F or C—Cl and
W$_4$ is a group of the formula

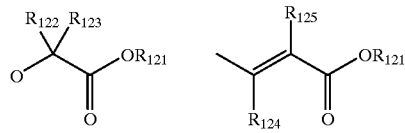

in which
R$_{122}$ and R$_{123}$ independently of one another are hydrogen or C$_1$–C$_4$alkyl and R$_{124}$ and R$_{125}$ independently of one another are hydrogen or C$_1$–C$_4$alkyl;
a compound of the formula XXIII

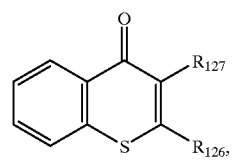

(XXIII)

in which
R$_{126}$ is hydrogen, cyano, halogen, C$_1$–C$_4$alkyl, C$_3$–C$_6$cycloalkyl, C$_1$–C$_4$alkoxy, C$_1$–C$_4$alkoxycarbonyl, C$_1$–C$_4$alkylthiocarbonyl, —NH—R$_{128}$, —C(O)NH—R$_{128}$, unsubstituted or substituted aryl or heteroaryl,
R$_{127}$ is hydrogen, cyano, nitro, halogen, C$_1$–C$_4$alkyl, C$_1$–C$_4$haloalkyl, C$_1$–C$_4$alkoxy, C$_1$–C$_4$thioalkyl, C$_1$–C$_4$haloalkyl, —NH—R$_{128}$, —C(O)NH—R$_{128}$, unsubstituted or substituted aryl, heteroaryl, and
R$_{128}$ is C$_1$–C$_4$alkyl, C$_1$–C$_4$haloalkyl, C$_3$–C$_4$alkenyl, C$_3$–C$_4$alkynyl, C$_3$–C$_4$cycloalkyl, unsubstituted or substituted aryl or heteroaryl, formyl, C$_1$–C$_4$-alkylcarbonyl, C$_1$–C$_4$-alkylsulfonyl;
a compound of the formula XXIV

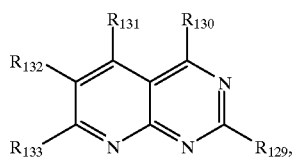

(XXIV)

in which
R$_{129}$ and R$_{130}$ independently of one another are hydrogen, C$_1$–C$_4$alkyl, C$_1$–C$_4$haloalkyl, C$_1$–C$_4$alkoxy, mono-C$_1$–C$_8$— or di-C$_1$–C$_8$alkylamino, C$_3$–C$_6$cycloalkyl, C$_1$–C$_4$thioalkyl, phenyl or heteroaryl, R$_{131}$ has the meaning of R$_{129}$ and is additionally OH, NH$_2$, halogen, di-C$_1$–C$_4$aminoalkyl, C$_1$–C$_4$alkylthio, C$_1$–C$_4$alkylsulfonyl or C$_1$–C$_4$alkoxycarbonyl, R$_{132}$ has the meaning of R$_{129}$ and is additionally cyano, nitro, carboxyl, C$_1$–C$_4$alkoxycarbonyl, di-C$_1$–C$_4$aminoalkyl, C$_1$–C$_4$alkylthio, C$_1$–C$_4$alkylsulfonyl, SO$_2$—OH, iso-C$_1$–C$_4$aminoalkylsulfonyl or C$_1$–C$_4$alkoxysulfonyl, R$_{133}$ has the meaning of R$_{129}$ and is additionally OH, NH$_2$, halogen, di-C$_1$–C$_4$aminoalkyl, pyrrolidin-1-yl, piperidin-1-yl, morpholin-1-yl, C$_1$–C$_4$alkylthio, C$_1$–C$_4$alkylsulfonyl, C$_1$–C$_4$alkoxycarbonyl, phenoxy, naphtoxy, phenylamino, benzoyloxy or phenylsulfonyloxy;
or a compound of the formula XXV

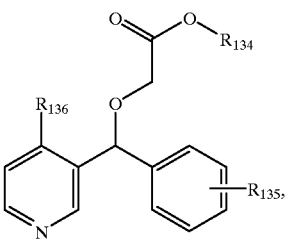

(XXV)

in which

R$_{134}$ is hydrogen, C$_4$alkyl, C$_1$–C$_4$haloalkyl, C$_2$–C$_4$alkenyl, C$_2$–C$_4$alkynyl or C$_1$–C$_4$alkoxy-C$_1$–C$_4$alkyl, R$_{135}$ is hydrogen, halogen, C$_1$–C$_4$alkyl, C$_1$–C$_4$haloalkyl or C$_1$–C$_4$alkoxy and R$_{136}$ is hydrogen, halogen, C$_1$–C$_4$alkyl, C$_1$–C$_4$haloalkyl or C$_1$–C$_4$alkoxy, with the proviso that R$_{135}$ and R$_{136}$ are not simultaneously hydrogen.

15. A composition according to claim 14, wherein it comprises, as herbicide-antagonistically effective amount, either a compound of the formula X

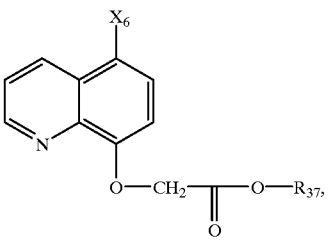

(X)

in which $R_{37}$ is hydrogen, $C_1$–$C_8$alkyl or $C_1$–$C_6$alkoxy- or $C_3$–$C_6$alkenyloxy-substituted $C_1$–$C_8$alkyl; and $X_6$ is hydrogen or chlorine; or a compound of the formula XI (XI)

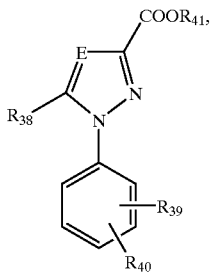

in which

E is nitrogen or methine; $R_{38}$ is —$CCl_3$, phenyl or halogen-substituted phenyl;

$R_{39}$ and $R_{40}$ independently of one another are hydrogen or halogen; and $R_{41}$ is $C_1$–$C_4$alkyl; or a compound of the formula XII (XII)

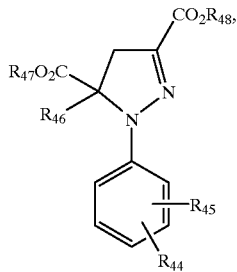

in which $R_{44}$ and $R_{45}$ independently of one another are hydrogen or halogen and $R_{46}$, $R_{47}$ and $R_{48}$ independently of one another are $C_1$–$C_4$alkyl.

16. A method for the selective control of weeds and grasses in crops of useful plants, wherein the useful plants, their seeds or seedlings or the area on which they are cultivated are treated with a herbicidally effective amount of a herbicide of the formula I and a herbicide-antagonistically effective amount of a safener of the formula X, XI, XII, XIII, XIV, XV, XVI, XVII, XVIII, XIX, XX, XXI, XXII, XXIII, XXIV or XXV as defined in claim 15.

17. A composition according to claim 11, which contains spray tank adjuvants.

18. A composition according to claim 14, which contains spray tank adjuvants.

* * * * *